United States Patent
Estes et al.

(10) Patent No.: US 10,787,646 B2
(45) Date of Patent: Sep. 29, 2020

(54) CULTIVATION OF HUMAN NOROVIRUSES

(71) Applicant: Baylor College of Medicine, Houston, TX (US)

(72) Inventors: Mary K. Estes, Houston, TX (US); David Graham, Houston, TX (US); Robert Legare Atmar, Houston, TX (US); Sue Ellen Crawford, Conroe, TX (US); Khalil Ettayebi, Pearland, TX (US); Kosuke Murakami, Houston, TX (US)

( * ) Notice: Subject to any disclaimer, the term of this patent is extended or adjusted under 35 U.S.C. 154(b) by 0 days.

(21) Appl. No.: 15/763,695

(22) PCT Filed: Oct. 3, 2016

(86) PCT No.: PCT/US2016/055204
§ 371 (c)(1),
(2) Date: Mar. 27, 2018

(87) PCT Pub. No.: WO2017/059449
PCT Pub. Date: Apr. 6, 2017

(65) Prior Publication Data
US 2018/0282704 A1 Oct. 4, 2018

Related U.S. Application Data

(60) Provisional application No. 62/378,896, filed on Aug. 24, 2016, provisional application No. 62/236,294, filed on Oct. 2, 2015.

(51) Int. Cl.
| | | |
|---|---|---|
| *C07K 14/435* | (2006.01) |
| *A61K 38/00* | (2006.01) |
| *A61K 39/02* | (2006.01) |
| *C07H 21/04* | (2006.01) |
| *C07K 14/47* | (2006.01) |
| *C12N 7/02* | (2006.01) |
| *C12N 7/00* | (2006.01) |
| *A61K 31/575* | (2006.01) |
| *C12N 5/00* | (2006.01) |
| *C12N 5/071* | (2010.01) |
| *G01N 33/569* | (2006.01) |

(52) U.S. Cl.
CPC .............. *C12N 7/02* (2013.01); *A61K 31/575* (2013.01); *C12N 5/0018* (2013.01); *C12N 5/0679* (2013.01); *C12N 7/00* (2013.01); *G01N 33/569* (2013.01); *C12N 2770/16051* (2013.01)

(58) Field of Classification Search
CPC .............. A61K 38/00; A61K 2039/522; A61K 2039/523; A61K 39/0011; C07K 14/47
See application file for complete search history.

(56) References Cited

U.S. PATENT DOCUMENTS 8,753,646 B2    6/2014  Abe et al.

FOREIGN PATENT DOCUMENTS

| WO | 88/01292 A1 | 2/1988 |
| WO | 2012/168930 A2 | 12/2012 |

OTHER PUBLICATIONS

Foulke-Abel et al. "Human enteroids as an ex-vivo model of host pathogen interactions in the gastrointestinal tract", Exp Biol Med, 2014, 239(9):pdf pp. 1-23.*
Straub et al., "Defining cell culture conditions to improve human norovirus infectivity assays", Water Science & Technology, 2013: 863-868.*
Straub et al., "Defining cell culture conditions to improve human norovirus infectivity assays", 2013, Water Science & Technology, 67.4:863-868.*
Faulk et al., "Human enteroids as an ex-vivo model of host-pathogen interactions in the gastrointestinal tract", 2014, 239(9):1124-1134.*
Shivanna et al., "The Crucial Role of Bile Acids in the Entry of Porcine Enteric Calicivirus", Virology, 2014:268-278.*
Arias et al., "Development of a reverse-genetics system for murine norovirus 3: long-term persistence occurs in the caecum and colon", Journal of General Virology, 2012, 93:1432-1441.*
Davies et al., "The viral mimetic polyinosinic: Polycytidylic acid alters the growth characterisitics of small intestinal and colonic crypt cultures", PLOS One, 2015:pdf pp. 1-19.*
Shivanna et al., "Ceramide formation mediated by acid sphingomyelinase facilitates endosomal escape of caliciviruses", Virology, 2015, 483:218-228.*
Mondal et al., "Novel bisegmented virus (picobirnavirus) of animals, birds and humans", Asian Pac J Trop Dis, 2014, 4(2):154-158.*

(Continued)

*Primary Examiner* — Barry A Chestnut
(74) *Attorney, Agent, or Firm* — Norton Rose Fulbright US LLP

(57) ABSTRACT

Embodiments of the disclosure concern systems, methods, and/or compositions for cultivation of mammalian viruses, including at least human noroviruses and sapoviruses within the Caliciviridae family of viruses. The ex vivo culture systems include intestinal enteroids in combination with bile or a functionally active fraction or component thereof. In specific embodiments, the culture system is utilized to test inactivation compounds for therapeutic or environmental efficacy and to test contaminated comestibles and/or environmental entities for determination of the presence of infectious virus. Furthermore, antiviral compositions may be tested using systems of the disclosure, including drugs, small molecule inhibitors, and biologies such as neutralizing monoclonal antibodies.

21 Claims, 44 Drawing Sheets

(56) References Cited

OTHER PUBLICATIONS

Arias et al. "Development of a Reverse-genetics System for Murine Norovirus 3: Long-term Persistence Occurs in the Caecum and Colon" Journal of General Virology. 2012. vol. 93; abstract; p. 1434, col. 2, paragraph 3; p. 1435, col. 2, paragraph 2; p. 1436, col. 2, paragraph 3.

Davies et al. "The Viral Mimetic Polyinosinic:Polycytidylic Acid Alters the Growth Characteristics of Small Intestinal and Colonic Crypt Cultures" PLoS ONE. Sep. 28, 2015, vol. 10, No. 9; abstract; p. 2, paragraph 4.

Straub et al. "Defining Cell Culture Conditions to Improve Human Norovirus Infectivity" Assays, Water Science & Technology. 2013. vol. 64, No. 4.

Foulke-Abel et al. "Human Enteroids as an Ex-vivo Model of Host-pathogen Interactions in the Gastrointestinal Tract" Experimental Biology and Medicine. Sep. 2014. vol. 239, No. 9; abstract; p. 6, paragraph 3.

Shivanna et al. "The Crucial Role of Bile Acids in the Entry of Porcine Enteric Calicivirus" Virology. May 2014. vol. 0; abstract; p. 2, paragraph 2.

Shivanna et al. "Ceramide Formation Mediated by Acid Sphingomyelinase Facilitates Endosomal Escape of Caliciviruses" Virology. Sep. 2015. vol. 483; abstract; p. 2, paragraph 3.

Mondal et al. "Novel Bisegmented Virus (Picobirnavirus) of Animals, Birds and Humans" Asian Pacific Journal of Tropical Disease. vol. 4, No. 2; abstract; p. 157, col. 2, paragraph 2.

Timothy M. Straub, et al; "Human Norovirus Infection of Caco-2 Cells Grown as a 3-Dimensional Tissue Structure"; J. Water Health, Jun. 2011: 9(2): 225-240.

Sayaka Takanashi, et al; "Failure of Propagation of Human Norovirus in Intestinal Epithelial Cells with Microvilli Grown in Three-Dimensional Cultures"; Arch Virol, Feb. 2014: 159(2): 257-266.

Efstathia Papafragkou, et al; "Challenges of Culturing Human Norovirus in Three-Dimensional Organiod Intestinal Cell Culture Models": PLOS One; Jun. 2013, vol. 8, Issue 6.

Melissa M. Herbst-Kralovetz, et al; "Lack of Norovirus Replication and Histo-Blood Group Antigen Expression in 3-Dimensional Intestinal Epithelial Cells"; Emerging Infectious Diseases; Mar. 2013, vol. 19, No. 3.

Khalil Ettayebi, et al; "Replication of Human Noroviruses in Stem Cell-Derived Human Enteroids"; Sciencemag.org; Sep. 23, 2016; vol. 353, Issue 6306.

Sarah Zhang, et al; "The Secret to a Breakthrough in Fighting Norovirus? Human Bile"; www.wired.com, Sep. 2, 2016.

Sato et al., "Long-term Expansion of Epithelial Organoids From Human Colon, Adenoma, Adenocarcinoma, and Barrett's Epithelium", Gastroenterology, vol. 141, No. 5, Jul. 27, 2011 (Jul. 27, 2011), pp. 1762-1772, W.B. Saunders Co, US.

Ahmad et al., "0ptimization of 3-D organotypic primary colonic cultures for organ-on-chip applications", Journal of Biological Engineering, vol. 8, No. I, Apr. 1, 2014 (Apr. 1, 2014), p. 9, Biomed Central Ltd, LO.

Sato et al., "Growing Self-Organizing Mini-Guts from a Single Intestinal Stem Cell: Mechanism and Applications", Science, vol. 340, No. 6137, Jun. 7, 2013 (Jun. 7, 2013), pp. 1190-1194.

Papafragkou et al., "Challenges of Culturing Human Norovirus in Three-Dimensional Organoid Intestinal Cell Culture Models", PLOS ONE, vol. 8, No. 6, Jun. 3, 2013 (Jun. 3, 2013), p. e63485.

Wobus et al., "Replication of Norovirus in Cell Culture Reveals a Tropism for Dendritic Cells and Macrophages", The EMBO Journal, vol . 14, No. 12, Jan. 1, 2004 (Jan. 1, 2004), p. 6095.

Duizer et al., "Laboratory efforts to cultivate noroviruses", Journal of General Virology., vol . 85, No. I, Jan. 1, 2004 (Jan. 1, 2004), pp. 79-87.

Boyer, James L., "Bile Formation and Secretion", Comprehensive Physiology, Jul. 1, 2013 (Jul. 1, 2013), John Wiley & Sons, Inc., Hoboken, NJ, USA.

Ettayebi et al., "Replication of human noroviruses in stem cell-derived human enteroids", Science, vol. 353, No. 6306, Aug. 25, 2016 (Aug. 25, 2016), pp. 1387-1393.

* cited by examiner

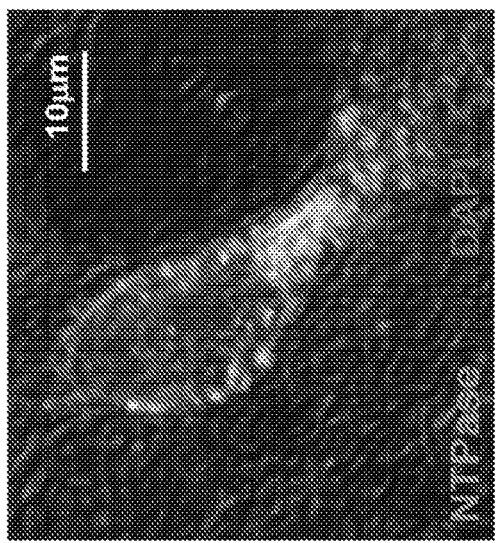
FIG. 4A
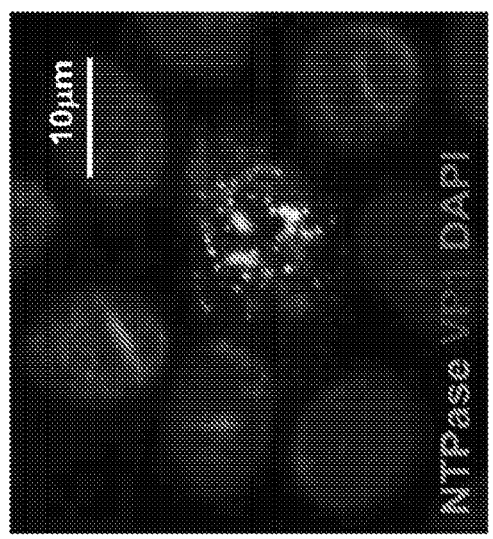
FIG. 4B

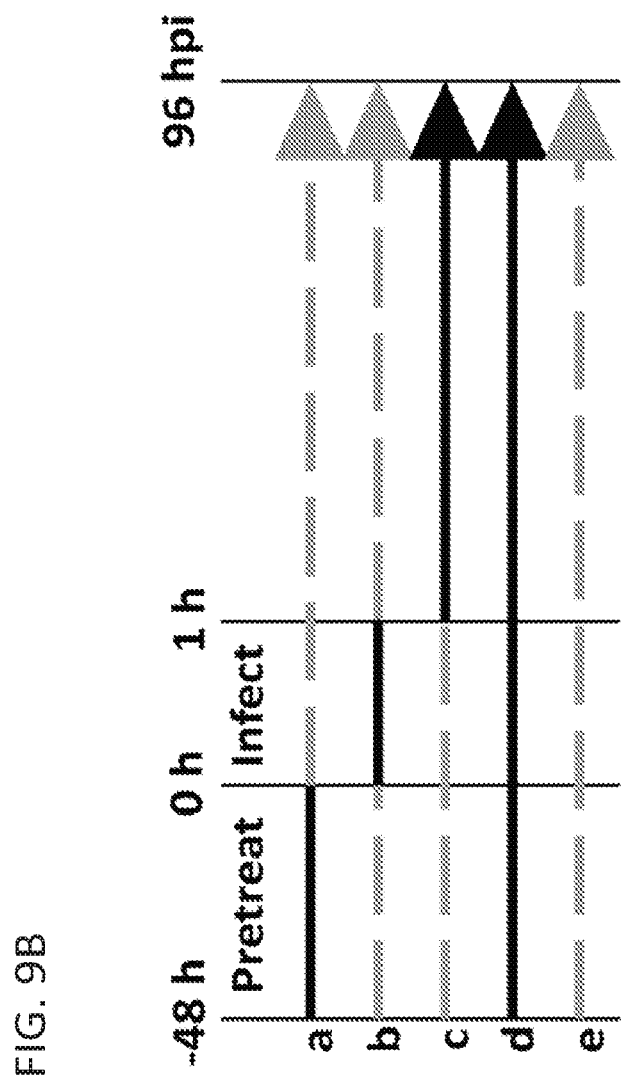

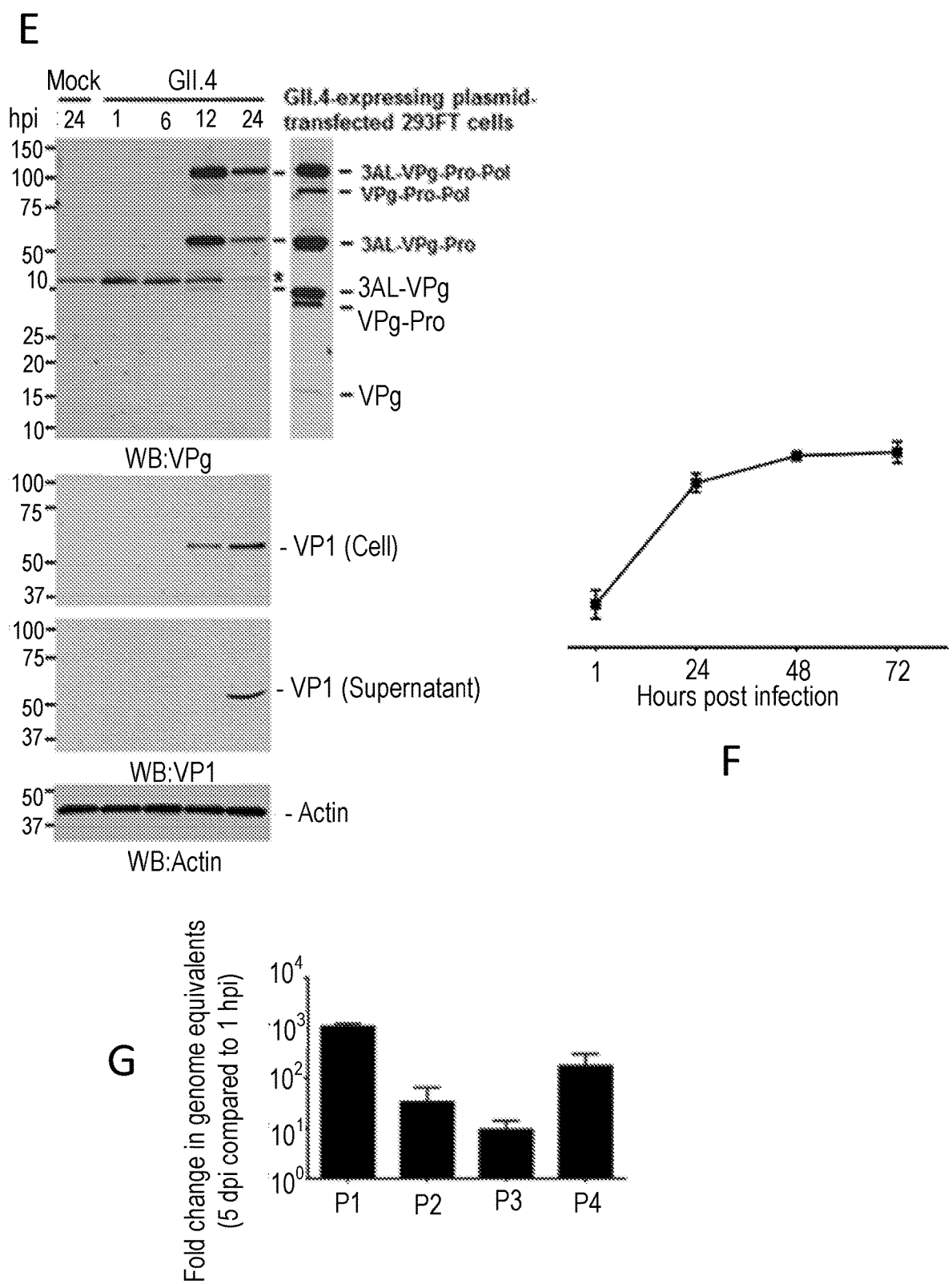
FIG. 15 - continued

FIG. 37

CULTIVATION OF HUMAN NOROVIRUSES

This application is a national phase application under 35 U.S.C. § 371 that claims priority to International Application No. PCT/US2016/055204 filed Oct. 3, 2016, which claims priority to U.S. Provisional Patent Application Ser. No. 62/236,294, filed Oct. 2, 2015, and to U.S. Provisional Patent Application Ser. No. 62/378,896, filed Aug. 24, 2016, all of which applications are incorporated by reference herein in their entirety.

STATEMENT REGARDING FEDERALLY SPONSORED RESEARCH OR DEVELOPMENT

This invention was made with government support under 2011-68003-30395 awarded by the U.S. Department of Agriculture and under PO1 AI057788 awarded by National Institutes of Health. The government has certain rights in the invention.

BACKGROUND

In 1972, the first virus that causes acute gastroenteritis was discovered by Al Kapikian who used immune electron microscopy to visualize Norwalk virus in an infectious stool filtrate derived from an outbreak of gastroenteritis in an elementary school in Norwalk, Ohio (9). This virus became the prototype strain for a group of noncultivatable viruses that are important etiologic agents of epidemic gastroenteritis in adults and children. Cloning of the Norwalk virus genome in 1990 led to its characterization as a member of the Norovirus genus in the Caliciviridae family (6, 7) and opened a molecular era of norovirus studies with new diagnostics that led to a better understanding of the epidemiology of human norovirus (HuNoV) disease. Now, in 2015, HuNoVs are recognized as the most common cause of epidemic and sporadic cases of acute gastroenteritis worldwide, as well as the leading cause of food-borne gastroenteritis, and they have replaced rotavirus as the predominant gastrointestinal pathogen in pediatric populations in developed countries following introduction of rotavirus vaccines [reviewed in (12)]. In spite of these advances, HuNoVs have resisted in vitro cultivation for more than 40 years, despite extensive attempts (3). Several reports of possible cultivation systems (16-18) have not been reproduced (5, 11, 19) or remained unconfirmed (8, 20). The lack of a robust, reproducible culture system for HuNoVs has been the major barrier to studying these viruses (4, 10). Such a system is critical to understand HuNoV-host interactions that underlie the high virus infectivity and explosive illness they cause and to understand how to prevent transmission and treat infections and illness.

The present disclosure provides solutions to the long-felt need in the art to provide suitable systems to cultivate viruses in the Caliciviridae family, including at least norovirus and sapovirus.

BRIEF SUMMARY

Embodiments of the disclosure concern methods, systems, and/or compositions related to the culturing of viruses in an environment that mimics their natural environment upon infection in a host. In specific embodiments, the viruses are previously considered to be non-cultivatable. In particular embodiments, there are methods, systems, and/or compositions related to the culturing of viruses in the Caliciviridae family or human sapoviruses. In specific embodiments, the disclosure is applicable to any member of the Caliciviridae family, although in particular embodiments the virus is Norovirus. In specific embodiments, any serotype or strain of viruses in the Caliciviridae family is cultivatable by methods of the disclosure.

Cultivation systems of the disclosure include enteroids (and/or cells and/or tissues therein) that are useful for cultivation of viruses in the Caliciviridae family, and in particular embodiments the systems include one or more other reagents, such as bile or functionally active fraction(s) or component(s) thereof. In some cases, the system utilizes bile acids, for example.

In particular embodiments, the Caliciviridae virus cultivation system encompasses at least the use of enteroids that mimic the mammalian intestinal environment, such as the human intestinal environment. The system encompasses enteroids that include cells of the intestinal epithelium that mimic the natural intestinal environment to facilitate cultivation of viruses in the Caliciviridae family Herein, in particular embodiments the disclosure describes the cultivation of human noroviruses (HuNoVs) in ex vivo nontransformed human small intestinal enteroid cultures. In specific embodiments, these are multicellular cultures that contain all or substantially all of the cells of the intestinal epithelium that are present in the small intestine. Embodiments of the disclosure provide an established cultivation system for Caliciviridae family viruses that mimics their replicative niche. In specific embodiments, provided herein is a HuNoV-cell culture system where filtered stool virus is inoculated onto novel ex vivo nontransformed human small intestinal enteroid cultures in a media comprising one or more additional supplements that would be present in the small intestine under normal conditions.

Systems of the disclosure allow for the manipulation of compositions to be tested for inactivation of caliciviruses (such as disinfectants and/or sanitizers, for example); for testing contaminated or potentially contaminated comestibles and/or beverages and/or surfaces and/or objects; for testing of compositions (such as vaccines, antivirals, immunologic compositions, and/or other therapeutics) for protection from calicivirus infection or disease; for development of therapeutics or diagnostics; for research applications, and so forth.

In some embodiments, methods of the disclosure are utilized for Astroviridae or Breda virus. Particular aspects of the disclosure concern methods related to noncultivatable human enteric viruses, such as viruses from the families Toroviridae, Picobirnaviridae, Reoviridae, Adenoviridae, Coronaviridae or Picornaviridae, for example. In specific embodiments, the viruses are astrovirus, Breda virus, human rotavirus, enteric adenovirus, human enteric coronavirus, or human enterovirus. The virus may be GII.4 variant human norovirus. The virus may be GII.3, GI.1, GII.4, GII.17, GII.6, GII.8, GII.12, or GII.14 strain human norovirus.

In one embodiment, there is a system for culturing a virus of the Caliciviridae family, comprising: a) mammalian small intestinal enteroid cultures; and b) bile or a functionally active fraction or component thereof. In some cases the system further comprises the virus. The cultures may be derived from human small intestines. The source of bile may be primate, human, pig, bovine, or a combination thereof, and in some cases the concentration of bile is in a range of 0.2-10% for human bile, 0.01-0.1% for bovine bile, or 1-2% for sow bile. In specific embodiments, the functionally active fraction or component thereof is not in a lipid micelle, is not a protein, is not a lipid or fatty acid, and/or is not cholesterol, whereas in some cases the functionally active fraction or component thereof comprises one or more lipids, one or more fatty acids, one or more sterols, or a combination thereof. The functionally active fraction or component thereof may comprise one or more bile acids, such as one or more selected from the group consisting of glycochenodeoxycholic acid, taurochenodeoxycholic acid, taurodeoxycholic acid, glycocholic acid, taurocholic acid, tauroursodeoxycholic acid, cholic acid, deoxycholic acid, lithocholic acid, chenodeoxycholic acid, glycodeoxycholic acid, taurolithocholic acid, ursodeoxycholic acid, glycolithocholic acid, or a combination thereof.

In some embodiments, there is a method of culturing a virus of the Caliciviridae family, comprising the step of subjecting the virus to any system encompassed by the disclosure under suitable conditions. In specific cases, when the virus is GII.3 type human Norovirus, the functionally active component thereof has a molecular weight that is greater than 100,000 molecular weight, and/or when the virus is GII.4 type human Norovirus, the functionally active component thereof has a molecular weight that is less than 100,000 molecular weight.

In certain embodiments, the enteroid cultures are plated as a monolayer of differentiated cells prior to exposure to the virus. In certain aspects, the bile is combined with the enteroid culture prior to, during, and/or after exposure of the system to the virus. In some cases, media for the culture comprises one or more growth factors, such as those that are selected from the group consisting of Wnt3A, nicotinamide, R-spondin-1, noggin, epidermal growth factor, gastrin, laminin-$\alpha$1, laminin-$\alpha$2, an inhibitor of Alk, an inhibitor of p38, fibroblast growth factor 10, and a combination thereof. In some cases, infection of the culture cells by the virus is monitored by assaying viral nucleic acid(s) levels and/or their identity, viral protein(s) levels and/or their identity, and/or cytopathic changes in the enteroids plated in a monolayer. The nucleic acid(s) levels and/or their identity may be assayed by quantitative reverse transcription-polymerase chain reaction, hybridization, and/or sequencing. Infection of the cultured cells by the virus may be monitored by assaying viral protein(s) levels and/or their identity. In some embodiments, the protein(s) levels and/or their identity are assayed by antibody, which may be labeled. In other embodiments, the protein(s) levels and/or their identity may be assayed by electron microscopy, ELISA, western blot, or a combination thereof. The viral protein(s) may be a structural protein, non-structural protein, or a combination thereof.

In some embodiments, the virus is obtained from a sample from human clinical samples, a sample from non-human mammals, environmental surfaces, comestibles, and/or liquids.

The genomic sequence of the virus from the sample may be compared to the genomic sequence of a virus cultivated by the method. In some cases the methods further comprise the step of obtaining a sample that comprises the virus. The enteroid cultures may be derived from tissue from an individual that has a functional fucosyltransferase 2 (FUT2), fucosyltransferase 3 (FUT3), and/or ABH glycans.

In one embodiment, there is a method of analyzing a composition for inactivation of a virus of the Caliciviridae family, comprising the step of subjecting an effective amount of the composition to any system encompassed by the disclosure. In specific embodiments, the method is further defined as: providing the system; and exposing the system to an effective amount of a composition being tested for the ability to inactivate the virus. In particular cases, the composition being tested for the ability to inactivate the virus is measured by the amount of culturable virus in the culture after exposing the virus to the composition. The amount of virus may be measured by genomic copy numbers of the virus, such as wherein the genomic copy numbers are measured by quantitative reverse transcription-polymerase chain reaction. In some embodiments, the composition is an antibody, an immunologic composition, a vaccine, a disinfectant or a sanitizer, a diagnostic for the virus, or an antiviral composition (such as a drug, small molecule inhibitor, biologic, neutralizing monoclonal antibody, or a combination thereof).

In one embodiment, there is a system for culturing a noncultivatable human enteric virus, comprising: a) mammalian small intestinal enteroid cultures; and b) bile or a functionally active fraction or component thereof. The system may further comprise the virus. In specific embodiments, the virus is from the family Toroviridae, Picobirnaviridae, Picornaviridae, or Coronaviridae. When the virus is from the family Picobirnaviridae, the virus may be picobirnavirus. When the virus is from the family Picornaviridae, the virus may be poliovirus or coxsackie B virus. When the virus is from the family Coronaviridae, the virus may be from the genus Coronavirinae, the genus Torovirus, or the order Nidovirales. A genus Coronavirinae virus may be human enteric coronavirus. In specific embodiments, the noncultivatable human enteric virus is an astrovirus, Breda virus, human rotavirus, enteric adenovirus, human enteric coronavirus, or human enterovirus.

In one embodiment, there is a method of culturing a noncultivatable human enteric virus, comprising the step of subjecting the virus to a system encompassed by the disclosure under suitable conditions.

The foregoing has outlined the features and technical advantages of the present disclosure in order that the detailed description of the disclosure that follows may be better understood. Additional features and advantages of the disclosure will be described hereinafter, which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features, which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

FIGS. 4A-4B. Detection of norovirus structural and non-structural proteins in GII.4-infected human intestinal enteroids. Monolayers of J2 human jejunal enteroids were mock-treated (4A) or GII.4_2006b (MDA) virus-infected (4B) for 1 hour at 37° C., and then the monolayers were washed twice. Monolayers were fixed at 72 hpi with methanol. Expression of the capsid protein (VP1) and the non-structural protein (NTPase) was detected using antibodies raised against GII.4_2012 (Sydney) virus-like particles (VLPs) in guinea pigs (red, anti-VP1, 1:100) or raised against GII.3 HuNoV NTPase in rabbits (green, NTPase, 1:100). Nuclei are detected with DAPI (blue). The left and right panel in 4B represent two different cells expressing both VP1 and NTPase; colocalization of these two HuNoV proteins is seen in some areas of the cell on the right (yellow).

FIGS. 9A-9C. Bile is required for GII.3 HuNoV replication and affects the cells and not the virus. (9A) Virus or cells were pretreated or not with bile prior to infection. The bile-virus mixture was diluted to decrease the bile concentration to 0.05% prior to infection of enteroid monolayers. Cells were treated with bile as diagramed before and during infection as in 9B, line d, or not treated and infected. (9B) Schematic of treatment of cells with bile at different times related to infection with results shown in 9C. (9C) Fold increases from 0 to 96 hpi are indicated above the 96 hpi bars.

FIG. 37. Neutralization of GII.4/2012 HuNoV infection. GII.4/2012 HuNoV was incubated with the indicated antibody for 1 hour. The virus-antibody mixture was then inoculated onto jejunal enteroids in triplicate and incubated for 1 hour; the enteroids were rinsed, and the virus yield at 24 hpi was determined by RT-qPCR. The control represents virus mixed with PBS. Serum1 (S 1) is a polyclonal human post-infection serum, and dilutions 1, 2 and 3 represent 1:1000, 1:5000, and 1:25000 dilutions, respectively. NV23, NS22, NS14, NV37, NV3, NS46, NV57 and F120 are murine monoclonal antibodies, and dilutions 1, 2, and 3 represent 1:10, 1:100, and 1:1000 dilutions, respectively. Syd is a guinea pig polyclonal antiserum generated against GII.4/2012 HuNoV, and dilutions 1, 2, and 3 represent 1:10, 1:100, and 1:1000 dilutions, respectively. The yield is expressed in genome equivalents per run, with each run representing 5% of the copy number is a culture well. The blue horizontal line shows 50% reduction in the GII.4/2012 HuNoV yield compared to the control yield. The monoclonal antibodies tested do not exhibit histoblood group blocking activity and have been previously characterized to belong to two separate epitope groups that map to the C-terminal P1 domain (Crawford et al., 2015: Clinical and Vaccine Immunology 22 (2): 168-177).

DETAILED DESCRIPTION

Figure 1:
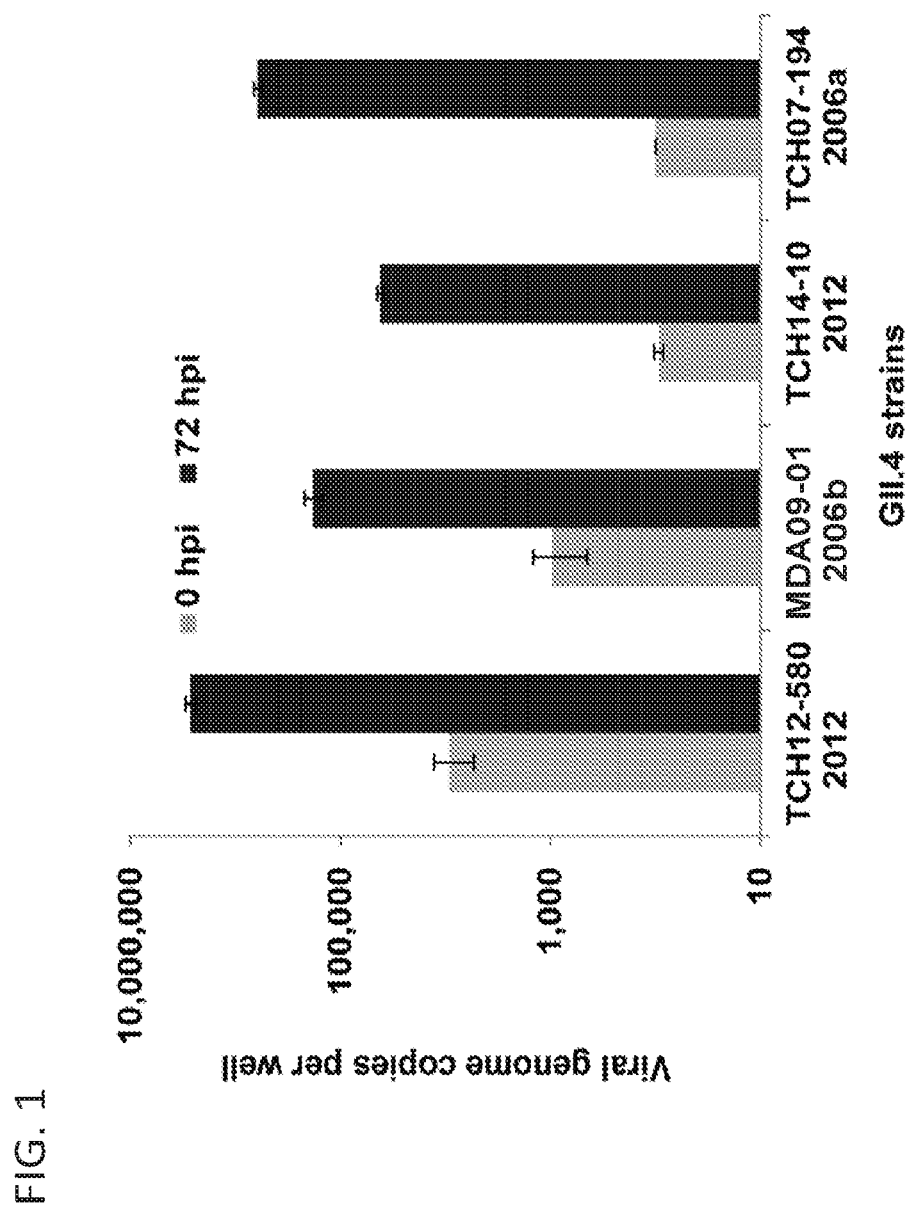
FIG. 1. GII.4 strains replicate in intestinal cells. Monolayers of (jejunal line 2) J2 human intestinal enteroids were exposed to the indicated HuNoV GII.4 virus-containing stool filtrates (9×105 genome copies of GII.4_2012 (Sydney), TCH12-580; 0.55×$10^5$ genome copies of GII.4_2006b (MDA), MDA09-01; 0.15×$10^5$ genome copies GII.4_2012 (Sydney), TCH14-10; 3.5×$10^5$ genome copies GII.4_2006a, TCH07-194) for 1 hour at 37° C. The treated monolayers were washed twice with CMGF(−) media (complete media without growth factors) and cultured for 72 hours in differentiation medium. At 72 hours post infection, the cells and media were harvested, RNA was extracted and viral genomic copies quantified by qRT-PCR. Data represent the mean of three wells quantified by qRT-PCR in duplicate, and the error bars denote standard deviation.

The words "a" and "an" when used in the present specification in concert with the word comprising, including the claims, denote "one or more." Some embodiments of the disclosure may consist of or consist essentially of one or more elements, method steps, and/or methods of the disclosure. It is contemplated that any method or composition described herein can be implemented with respect to any other method or composition described herein embodiments which are disclosed and still obtain a like or similar result without departing from the spirit and scope of the disclosure.

As used herein, the term "enteroid" is defined as a three-dimensional culture system propagated from stem cells from intestinal crypts isolated from human surgical specimens, endoscopic biopsies, autopsy specimens, or a combination thereof.

Embodiments of the disclosure concern methods, systems, and/or compositions for culturing any virus that infects the gastrointestinal tract of a mammal, including a human, primate, bovine, pig, dog or cat, for example. In specific embodiments, the virus is a member of the Caliciviridae family, including at least norovirus and sapovirus. In some embodiments the virus is rotavirus. In alternative cases the virus is from the family Toroviridae, Picobirnaviridae, Picornaviridae, Coronaviridae, Astroviridae, Reoviridae or Adenoviridae.

Human noroviruses (HuNoVs) are the most common cause of acute gastroenteritis worldwide as well as the leading cause of foodborne gastroenteritis. This disclosure concerns cultivating HuNoVs in ex vivo nontransformed human small intestinal enteroid cultures, in specific embodiments. These are multicellular cultures that contain all of the cells of the intestinal epithelium, which are present in the small intestine. This achievement ends the extensive attempts by many investigators over 40 years who have tried to culture these important human pathogens.

I. Embodiments of Gastrointestinal Virus Cultivation Systems

The present disclosure provides embodiments of cultivation systems useful for cultivation of viruses that invade the tissues of the stomach, intestine, and/or colon. In certain embodiments, the methods and compositions concern cultivation of gastrointestinal viruses or enteric viruses. In particular embodiments, the viruses that are cultivated are from the family of Caliciviridae. The viruses cultivated in the present systems may cause viral gastroenteritis, in at least some embodiments. The systems are useful for enteric viruses that cause infection of any mammal, including primates or including at least human, primate, bovine, pig, dog, and cat, for example.

A. Enteroids or Other Cultures

Embodiments of Caliciviridae viral cultivation systems of the disclosure utilize environments that replicate the natural and normal human intestine.

In particular embodiments, the cultivation system employs human intestinal enteroids. As referred to herein, an enteroid is a three-dimensional culture system originating from stem cells from intestinal crypts obtained from human surgical specimens, autopsy specimens, and/or endoscopic biopsies. The skilled artisan recognizes that the term "organoid" may be used interchangeably in the art with the term "enteroid" in some publications. As used herein, enteroids are made from human biopsy, autopsy specimens, or surgical specimens and are not made from approved stem cell lines or induced pluripotent stem cells. In certain embodiments, the cells of the enteroid culture are nontransformed cells (not derived from tumor specimens and not cancer cells).

In specific embodiments, multicellular cultures that comprise all or substantially all of the cells of the intestinal epithelium that are present in the small intestine (including stem cells, enterocytes, Goblet cells, enteroendocrine cells and/or Paneth cells) are utilized. In particular cases, the culture system comprises enteroids that are jejunal, duodenal, ileal, or a combination thereof. In specific embodiments, the enteroids are crypt-derived enteroids. In at least some cases, the starting material for the enteroids is one or more biopsies from a mammal. In particular embodiments, the tissue comprises stem cells that have the capacity for regenerating and differentiating into the specific cell types that make up the intestinal epithelium. In specific embodiments, the stem cells are isolated from intestinal crypts. In certain embodiments, the source of tissue for the generation of the enteroids is small intestine, colon, stomach, or a combination thereof. The tissue may come from surgically resected intestinal tissues, endoscopic biopsies, autopsy specimens, and so forth.

In embodiments wherein the tissue is obtained from a human individual, the individual may have a functional fucosyltransferase 2 (FUT2), functional fucosyltransferase 3, ABH glycans, or a combination thereof so that the cells of the enteroids allow, or are more likely to allow, efficient Caliciviridae (particularly HuNoV or sapovirus) infection.

In specific embodiments, the enteroids are plated on monolayers for infection with HuNoV. Examples of monolayer generation are known in the art. (22) In at least some cases, the cultures are generated upon exposure of intestinal cells of isolated crypts that contain stem cells or a combination of stem cells and Paneth cells to one or more growth factors. Specific examples of growth factors include Wnt3A, nicotinamide, R-spondin-1, noggin, epidermal growth factor (EGF), gastrin, laminin-α1, laminin-α2, an inhibitor of Alk (such as A-83-01), an inhibitor of p38 (such as SB202190), fibroblast growth factor 10, or a combination thereof. The media for the generation and maintenance of the cultures may comprise standard basal media or media comprising suitable levels of one or more growth factors (such as EGF, noggin, R-spondin, Wnt3A, nicotinamide, SB202190, and/or acetylcysteine).

Examples of methods of generating enteroids for use in cultivation systems of the disclosure are as follows: intestinal fragments or biopsy intestinal sample fragments are obtained or generated and washed with buffer (such as PBS) until the supernatant is clear, incubated in a buffer that comprises EDTA, and then the fragments are vigorously resuspended to isolate intestinal crypts. Following a resuspension/sedimentation procedure, supernatants comprising crypts are subject to procedures to separate crypts into single cells. These crypts are expanded as 3D cultures and then embedded in a gelatinous protein mixture (such as Matrigel or hydrogels), followed by polymerization. After further expansion in growth media, the cells in the three-dimensional cultures are dissociated and may be plated onto monolayers on top of a thin coating of Matrigel or collagen or other such substrates for forming monolayer cultures. Cultures in either 3D or monolayer (2D) format can be differentiated by withdrawal of Wnt3a, for example, which then results in the appearance of all the cells in the epithelium being produced. Both non-differentiated and differentiated cultures can be infected, in certain embodiments, but in particular cases only differentiated cultures may be infected.

In particular embodiments, the infection of the virus in the culture results in detectable changes in the culture, such as cytopathic changes, and such changes can be detected by assaying for viral structural and/or nonstructural proteins and increases in viral RNA. In specific embodiments, viruses are monitored through detection of one or more viral antigens, including at least in some cases their localization.

Enteroids may be transduced with viral vectors (such as adenovirus, lentivirus, or adeno-associated virus, for example); when lentivirus or adeno-associated viruses are utilized, they can permanently express one or more genes. CRISPR/Cas9 or CRISPRi may alternatively be employed to genetically manipulate the cultures to express one or more genes. The cells of the enteroids may be transduced to overexpress molecule(s) in pathways identified to be critical for virus entry or replication. Pathways to be targeted may include ESCRT, autophagy, calcium mobilization, lipid biogenesis and cholesterol metabolism, and the unfolded protein response. A variety of biosensors can also be expressed that can detect by fluorescent imaging or flow cytometry a cell property that changes after infection. These modified cell lines may be established cells that currently do not support HuNoV replication in the presence of bile or bile acids (e.g., HEK, CaCo-2, HT29, MA104, Vero, as examples). In addition, permissive cells within the enteroid cultures may be identified and immortalized by expressing molecules such as telomerase or SV40 T antigen to develop homogeneous epithelial cell lines that support virus replication and can be expanded easily and robustly. Examples of some specific proteins in the pathways above for overexpression are Rab1, dynamin, VAP-1, VAMP1, ALIX, FXR, SHP and PPAR gamma, or silencing HMG-CoA synthase and ACAT.

In alternative embodiments, gastroids or colonoids are utilized in the system instead of enteroids to culture viruses that replicate in the stomach or colon, for example. Gastroids and colonoids may be produced in the same manner and with the same medium as enteroids from human tissue with the exception that the Wnt3a concentration in the growth media is increased to obtain gastroids, in at least particular cases.

B. Bile Compositions or Functional Component(s) Thereof

In particular embodiments, the cultivation system of the present disclosure utilizes bile or one or more functionally active fraction(s) or component(s) thereof. A functionally active fraction or component thereof as referred to herein is a fraction or component of bile that is required to allow viral replication (for HuNoV embodiments, for some strains of HuNoV, such as GII.3, GII.17 and GI. 1 strains) or enhances viral replication (for HuNoV embodiments, for some strains of HuNoV, such as GII.4 strains). In some embodiments, bile or components of bile would be required or would enhance replication of the viruses.

Bile may be used at any concentration in the system, and in some cases the concentration of bile is different for different viruses. Examples of concentrations include the following percentages (or at least one or more of these percentages or no more than one or more of these percentages): 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50%. In specific embodiments, the bile is in a concentration in a range from 0.01% to 50%; 0.1% to 50%; 1.0% to 50%, 10% to 50%; 0.01% to 40%; 0.1% to 40%; 1.0% to 40%, 10% to 40%; 0.01% to 30%; 0.1% to 30%; 1.0% to 30%, 10% to 30%; 0.01% to 20%; 0.1% to 20%; 1.0% to 20%, 10% to 20%; 0.01% to 10%; 0.1% to 10%; 1.0% to 10%, 0.01% to 5%; 0.1% to 5%; 1.0% to 5%; 0.01% to 1.0%; and so forth. Minimum concentrations of bile may be at least or no more than 0.075%, 0.005%, 0.0025%, 0.001%, and so forth.

The maximum bile concentration is the concentration where it is toxic to cells and the minimum concentration is the concentration wherein it no longer allows viral replication. Such concentrations may be determined empirically using standard methods in the art or methods analogous to those described herein. In at least some cases, the bile concentration differs depending on the species source. In specific embodiments, when the source of bile is human, a range of concentration is 0.2-10%. When the bile is human bile, the concentration may be no more than 50, 49, 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1%, in at least some cases. Human bile concentrations, in some cases, may be in a range of 0.2-10%, 0.2-9%, 0.2-8%, 0.2-7%, 0.2-6%, 0.2-5%, 0.2-4%, 0.2-3%, 0.2-2%, 0.2-1%, 0.2-0.5%, 0.3-10%, 0.3-9%, 0.3-8%, 0.3-7%, 0.3-6%, 0.3-5%, 0.3-4%, 0.3-3%, 0.3-2%, 0.3-1%, 0.3-0.5%, 0.4-10%, 0.4-9%, 0.4-8%, 0.4-7%, 0.4-6%, 0.4-5%, 0.4-4%, 0.4-3%, 0.4-2%, 0.4-1%, 0.4-0.5%, 0.5-10%, 0.5-9%, 0.5-8%, 0.5-7%, 0.5-6%, 0.5-5%, 0.5-4%, 0.5-3%, 0.5-2%, 0.5-1%, 0.6-10%, 0.6-9%, 0.6-8%, 0.6-7%, 0.6-6%, 0.6-5%, 0.6-4%, 0.6-3%, 0.6-2%, 0.6-1%, 0.7-10%, 0.7-9%, 0.7-8%, 0.7-7%, 0.7-6%, 0.7-5%, 0.7-4%, 0.7-3%, 0.7-2%, 0.7-1%, 0.8-10%, 0.8-9%, 0.8-8%, 0.8-7%, 0.8-6%, 0.8-5%, 0.8-4%, 0.8-3%, 0.8-2%, 0.8-1%, 0.9-10%, 0.9-9%, 0.9-8%, 0.9-7%, 0.9-6%, 0.9-5%, 0.9-4%, 0.9-3%, 0.9-2%, 0.9-1%, 1-10%, 1-9%, 1-8%, 1-7%, 1-6%, 1-5%, 1-4%, 1-3%, 1-2%, 2-10%, 2-9%, 2-8%, 2-7%, 2-6%, 2-5%, 2-4%, 2-3%, 3-10%, 3-9%, 3-8%, 3-7%, 3-6%, 3-5%, 3-4%, 4-10%, 4-9%, 4-8%, 4-7%, 4-6%, 4-5%, 5-10%, 5-9%, 5-8%, 5-7%, 5-6%, 6-10%, 6-9%, 6-8%, 6-7%, 7-10%, 7-9%, 7-8%, 8-10%, 8-9%, or 9-10%.

When the bile is bovine bile, the concentration may be no more than 5, 4, 3, 2, 1, or 0.5% concentration, in at least some cases. Bovine bile concentrations, in some cases, may be in a range of 0.01-0.1%, 0.01-0.09%, 0.01-0.08%, 0.01-0.07%, 0.01-0.06%, 0.01-0.05%, 0.01-0.04%, 0.01-0.03%, 0.01-0.02%, 0.02-0.1%, 0.02-0.09%, 0.02-0.08%, 0.02-0.07%, 0.02-0.06%, 0.02-0.05%, 0.02-0.04%, 0.02-0.03%, 0.03-0.1%, 0.03-0.09%, 0.03-0.08%, 0.03-0.07%, 0.03-0.06%, 0.03-0.06%, 0.03-0.05%, 0.03-0.04%, 0.04-0.1%, 0.04-0.09%, 0.04-0.08%, 0.04-0.07%, 0.04-0.06%, 0.04-0.05%, 0.05-0.1%, 0.05-0.09%, 0.05-0.08%, 0.05-0.07%, 0.05-0.06%, 0.06-0.1%, 0.06-0.09%, 0.06-0.08%, 0.06-0.07%, 0.07-0.1%, 0.07-0.09%, 0.07-0.08%, 0.08-0.1%, 0.08-0.09%, or 0.09-0.1%.

When the bile is sow bile, the concentration may be no more than 20, 19, 18, 17, 16, 15, 14, 13, 12, 11, 10, 9, 8, 7, 6, 5, 4, 3, 2, 1, or 0.5%, in at least some cases. Sow bile concentrations, in some cases, may be in a range of 1-2%, 1.1-2%, 1.2-2%, 1.3-2%, 1.4-2%, 1.5-2%, 1.6-2%, 1.7-2%, 1.8-2%, or 1.9-2%.

In some embodiments, the source of the bile is mammalian, including from human, bovine, or pig. In particular cases, the organism from which the enteroid tissue is generated is the same organism from which the bile is obtained.

The bile may be fractionated prior to its employment in the system, including by standard fractionation methods, and its components may be identified by mass spectrometry, for example.

In certain embodiments, the enteroids are cultured with the bile prior to, during, and/or subsequent to viral infection. In specific embodiments, the enteroids are cultured with bile or bile acids prior to infection, and in at least some cases the bile and/or bile acids are combined with the enteroids at least or no more than 48, 47, 46, 45, 44, 43, 42, 41, 40, 39, 38, 37, 36, 35, 34, 33, 32, 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, 1, or 0.5 hours prior to infection.

In particular embodiments, one or more bile acid selected from the group consisting of glycochenodeoxycholic acid, taurochenodeoxycholic acid, taurodeoxycholic acid, glycocholic acid, taurocholic acid, tauroursodeoxycholic acid, cholic acid, deoxycholic acid, lithocholic acid, chenodeoxycholic acid, glycodeoxycholic acid, taurolithocholic acid, ursodeoxycholic acid, glycolithocholic acid, and a combination thereof are utilized in systems of the disclosure. In specific embodiments, deoxycholic acid does not enhance GII.3 replication.

In particular cases, one or more concentrations of bile acids may be employed in the systems of the disclosure and still enhance replication. In particular embodiments the concentration of any bile acid is from 5 µM to 500 µM. Examples of ranges also include 5-450 µM; 5-400 µM; 5-350 µM; 5-300 µM; 5-250 µM; 5-200 µM; 5-150 µM; 5-100 µM; 5-75 µM; or 5-50 µM.

In alternative embodiments, certain stomach, colon, and intestinal viruses do not require the addition of bile or a functional component(s) thereof (including bile acids) for cultivation in a system that utilizes the respective enteroids, gastroids, or colonoids. For example, rotavirus replication is not enhanced with bile but is enhanced with pancreatic enzymes in an enteroid system.

C. Viral Components for Cultivation and Cultivation Thereof

The culturing systems, methods, and/or compositions of the present disclosure may be used in any strain, genotype, or variant of any virus that infects the gastrointestinal tract of a mammal. In specific embodiments, the mammal is a human, bovine, or pig. In cases wherein norovirus is cultured, any genogroup may be cultivated, including GI, GII, GIII, GIV, GV, GVI or GVII. Variants for HuNoV, including at least GII.4 and GII.3, may be cultured, in specific cases.

In some embodiments, a source of virus for cultivation includes human clinical samples, samples from other mammals (e.g., primates, canine, feline, porcine, bovine), environmental surfaces, foods (fruit, shellfish, ready-to-eat foods, etc.), liquids (e.g., water), and other environmental samples (e.g., sewage, sludge).

The viruses may be cultivated upon exposure to the system comprising the enteroids and the bile or functionally active fraction(s) or component(s) thereof. In particular embodiments, the enteroids are cultured for a specific amount of time prior to exposure to the virus(es). In specific embodiments, the enteroids are cultured for at least or no more than 0.5-3 hours prior to exposure to the virus. Prior to exposure of the viruses, the enteroid culture may have the gelatinous protein mixture removed. In some cases, the bile is combined with the enteroid culture prior to, during, and/or after exposure of the virus to the enteroid culture.

In at least particular embodiments, the enteroid cultures are plated in a monolayer prior to exposure to the virus, and in specific embodiments the monolayer comprises differentiated cells. The combination of bile with the enteroid culture may occur prior to, during, and/or after exposure of the system to the virus.

In at least some cases, infection of the culture cells by the virus is monitored, and the monitoring can occur by any suitable means, including by measuring viral nucleic acid(s) levels, viral protein(s) levels, and/or cytopathic changes in the enteroids that are plated in a monolayer. When viral nucleic acids are measured, they may be analyzed for identity and/or quantity, and they may be analyzed by polymerase chain reaction, including at least quantitative RT-PCR; hybridization methods (such as dot blot hybridization or in situ hybridization); sequencing; or a combination thereof, for example. In certain embodiments, the genes being assayed using reverse-transcription polymerase chain reaction (particularly quantitative RT-PCR) include housekeeping genes, such as enzymes, dehydrogenases, and so forth. Examples of viral genes include p48, NTPase, p22, VPg, protease, RNA-dependent RNA polymerase, VP1 and VP2

In at least some cases, infection of the culture cells by the virus is monitored by measuring viral protein(s) levels and/or identity. In specific examples, the protein(s) levels are measured by antibody, and in some cases the antibody is labeled. The viral proteins may be of any kind, including one or more structural proteins, one or more non-structural proteins, or a combination thereof. In some cases, viral proteins are detected by immunofluorescence, immunohistochemistry, and/or by Western blots. In other cases, virus production is measured by ELISA, such as to detect capsid structural protein, and/or it may be assayed by electron microscopy and/or immune electron microscopy.

In some cases, it is useful to monitor if the viruses are mutating over the course of propagation. Thus, in specific embodiments this is measured by detecting at least part of the sequence of nucleic acid(s) of the viruses produced by the system, particularly in comparison to the original virus for the culture. For example, the genomic sequence of the virus from a sample may be compared to the genomic sequence of a virus cultivated by the method, such as using standard sequencing techniques, for example.

II. Methods of Use of Cultivation Systems

The cultivation system of the present disclosure may be used for research purposes, for therapy or diagnostic identification purposes, for viral identification purposes, and so forth. In particular embodiments, one can cultivate any viruses of Caliciviridae for their robust replication and passaging to study and/or test such viruses related to worldwide disease. One can use the systems to characterize cellular processes and pathways to obtain information on targets exploited by the viruses for infection, replication, and/or induction of pathogenesis. One can also evaluate whether or not a particular virus is infectious, thereby providing useful information related to public health. One can also assess methods and/or compositions (such as disinfectants and/or sanitizers) that can inactivate the virus and such activity can be measured for effectiveness. In addition, one can characterize assays useful for measuring antibodies (such as protective neutralizing antibodies, for example), and whether or not the antibodies can elicit natural or vaccine-induced immunity. One can also cultivate the viruses to understand host genetics in viral evolution. In a specific embodiment, the cultivation system provides for the development of a vaccine (for example, a live attenuated vaccine) to induce long lasting immunity. In specific embodiments of the methods, the effects are measured of cytokines/chemokines/other innate immunity molecules on the susceptibility of the enteroids to infection (e.g., types 1 and 3 IFNs block replication).

In specific embodiments, a sample from an individual that is known to have or that is suspected of having Caliciviridae infection or that is suspected of having been exposed to Caliciviridae infection is subjected to cultivation systems and/or methods of the disclosure. The methods may be applicable to acutely infected individuals and/or chronically infected individuals. The sample may be taken at from an individual at any time after infection or exposure, including at or at least at 1, 2, 3, 4, 5, 6, 7, 8, 9, 10, 11, 12, 13, 14, 15, 16, 17, 18, 19, 20, 21, 22, 23, 24, 25, 26, 7, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more days after infection or exposure. In some individuals, a sample is subjected to cultivation methods of the disclosure after 1, 2, 3, 4, 5, 6, 7, 8, 9, 10, 11, 12, 13, 14, 15, 16, 17, 18, 19, 20, 21, 22, 23, 24, or more months after infection or exposure.

In specific embodiments, a sample from an environment known to have been exposed or suspected of having been exposed to Caliciviridae is subjected to cultivation systems and/or methods of the disclosure. The environment may be a health care facility (including hospital or nursing home), a food service facility (such as a restaurant), banquet halls, school, transportation vehicle (including boat (such as a cruise ship), airplane, train, and so forth), sports or entertainment venue, institutional setting, school, child care center, prison, college, military encampment, and so forth.

In some embodiments, an individual is screened for having Caliciviridae infection prior to exposure to an environment that encompasses large groups of individuals, such as a health care facility (including hospital or nursing home), a food service facility (such as a restaurant), banquet halls, school, transportation vehicle (including boat (such as a cruise ship), airplane, train, and so forth), sports or entertainment venue, institutional setting, school, child care center, prison, college, military encampment, and so forth.

An individual whose sample may be subjected to methods of the disclosure include an individual that may or may not be showing symptoms of Caliciviridae infection. Symptoms include at least acute gastroenteritis, stomach inflammation (for example, when the virus is a gastrointestinal virus), intestinal inflammation, and so forth. In specific embodiments, an individual with Caliciviridae infection experiences at least one of the following symptoms: nausea, projectile vomiting, diarrhea, and/or abdominal pain. An individual whose sample may be tested using cultivation systems of the disclosure include an individual that has contact with food to be served to the public (such as leafy greens, fresh fruits, and/or shellfish), an individual with exposure to the public, and so forth.

Methods of the disclosure may be used to test comestibles and/or beverages that are implicated in outbreaks to determine if infectious virus (such as HuNoV) is present. Also, methods of the disclosure may be used in asymptomatic patients who might be food handlers to determine if they are shedding a virus, such as HuNoV. Individuals shed at least some viruses for a long period of time after an acute infection, and the individual can be symptomatic or asymptomatic. In specific embodiments, methods of the disclosure may be used to test shedding in individuals who have chronic viral infections, such as chronic HuNoV infections (immunocompromised or transplant patients, for example). In certain embodiments, methods of the disclosure may be used to evaluate the effectiveness of one or more antiviral treatments. In specific embodiments, methods of the disclosure are utilized to determine when an individual in the food service industry can return to work following gastroenteritis, including after having HuNoV gastroenteritis, for example.

In at least some cases, the enteroid culture system of the disclosure allows measurement of direct neutralization activity in samples, including serum samples, for example. The culture system allows for cultivation of viruses that are resistant to disinfectant and/or sanitizer, in at least some cases.

In certain embodiments, there are methods of providing to systems of the disclosure an effective amount of a composition being tested for the ability to inactivate the virus. This new cultivation system will allow (i) the testing of inactivation methods and sanitizers to reduce transmission by inactivating these viruses, (ii) testing of possible contaminated food and other environmental surfaces or vehicles to determine whether or not infectious virus is present, (iii) determination of whether antibodies induced by natural infection or vaccination correlate with protection from infection or disease following a subsequent exposure to infectious virus (iv) determination of the number of serotypes of virus and whether broadly neutralizing antibodies can be induced by vaccination to protect against infection and/or disease, (v) development of live, attenuated or inactivated vaccines, (6) development of improved diagnostic assays, (vi) evaluation of antivirals and other therapeutics, (vii) discovery of neutralizing epitopes on virus particles that can be used to make new vaccines or improve current vaccines and understand virus evolution, (viii) discovery and elucidation of the molecular mechanisms that regulate virus replication, which could be targets for preventative drugs or treatments; ix) detection of virus in comestibles and/or water to determine vehicles implicated in outbreaks of gastroenteritis; x) detection of virus in chronically infected individuals to determine whether they are potentially infectious for public health management; xi) evaluating of the effectiveness of treatments in patients.

In certain embodiments, upon infection the enteroid cultures are assayed for the presence of one or more viral proteins, and the one or more viral proteins may be a structural or non-structural or when there is more than one assayed, one or more of each type. Exemplary structural proteins include major capsid protein VP1 and the minor structural protein VP2, and exemplary non-structural proteins include p48, NTPase, p22, VPg, protease, and RNA-dependent RNA polymerase (RdRp). Any of these proteins may be assayed to verify the presence or activity of Norovirus in culture.

EXAMPLES

The following examples are included to demonstrate preferred embodiments of the disclosure. It should be appreciated by those of skill in the art that the techniques disclosed in the examples that follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

Cultivation of Human Noroviruses

Human noroviruses infect and replicate in human intestinal enteroids. Reasoning that a culture model that mimics the environment of the natural infection would support HuNoV growth, we generated human intestinal enteroids from stem cells isolated from intestinal crypts following the methods of Sato et al. (14). Monolayer cultures of human jejunal enteroids were produced and infected with 10% stool samples (although one could utilize 5-50% stool samples) that were filtered (0.22 μm filter) and contained high HuNoV genomic copy numbers. An increase in the quantitative RT-PCR (qRT-PCR) signal was used as an indicator of HuNoV replication. FIG. 1 shows representative data from four GII.4 strains, and illustrates the robust (2-3.5 log 10 increase in viral-specific RNA over 72 hours) replication of these GII.4 strains. Such primary infections are highly reproducible. Currently we have successfully obtained replication of 10 HuNoV strains characterized as being in 4 HuNoV genotypes. The strains of virus include several GII.4 variants, a GI.1, GII.3, and GII.17 strains (Table 1). The quantity of human noroviruses was determined as cycle threshold (CT) values using qRT-PCR and subsequently converted into genomic equivalents (15). The initial viral load of each stool sample, determined by qRT-PCR of serial dilutions of the processed stool samples, shows that a range of titers of input virus could be cultured (Table 1).

TABLE 1

HuNoV strains that replicate in human intestinal enteroids and titer of virus in the original stool filtrate.

| Sample | Genotype (Variant) | Titer (genomic copies/ul) |
|---|---|---|
| 551-07 | GI.1 | $3.4 \times 10^6$ |
| TCH04-577 | GII.3 | $8.5 \times 10^6$ |
| TCH12-580 | GII.4 (2012 Sydney) | $1.8 \times 10^8$ |
| TCH14-10 | GII.4 (2012 Sydney) | $3.0 \times 10^6$ |
| TCH07-194 | GII.4-(2006a) | $7.0 \times 10^7$ |
| TCH07-882 | GII.4-(2006b) | $1.5 \times 10^7$ |
| TCH08-227 | GII.4-(2006b) | $5.3 \times 10^6$ |
| MDA09-01 | GII.4-(2006b) (MDA) | $1.1 \times 10^7$ |
| TCH11-64 | GII.4-(2009) | $3.0 \times 10^7$ |
| TCH14-385 | GII.17 | $1.4 \times 10^7$ |

Figure 2:
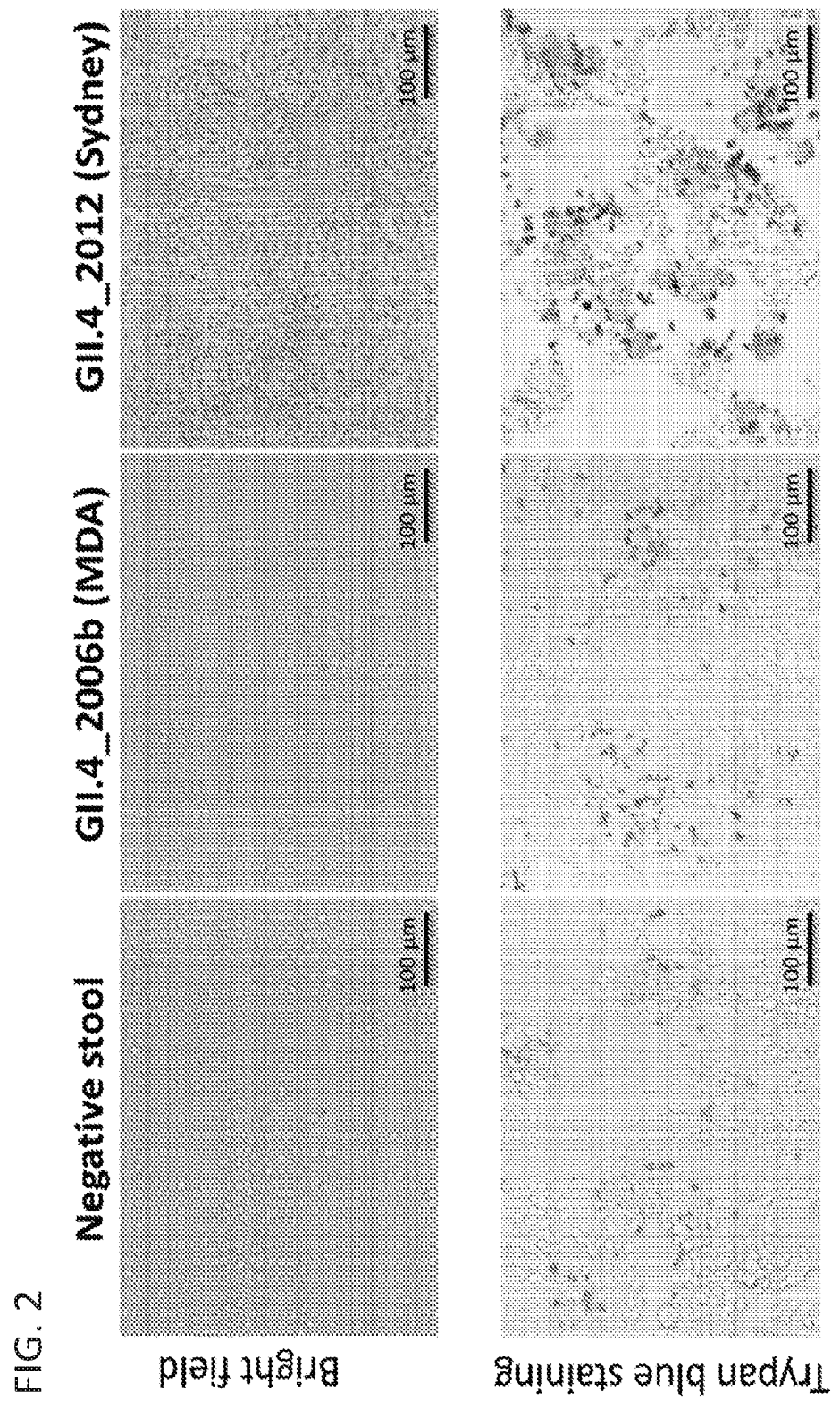
FIG. 2. Cytopathic effect of HuNoV infection. Monolayers of J2 human intestinal enteroids were cultured with a HuNoV-negative stool filtrate or stool filtrates containing GII.4_2006b (MDA) or GII.4_2012 (Sydney) virus for 1 hour at 37° C. The treated monolayers were washed twice with CMGF(−) media (complete media without growth factors) and cultured for 6 days in differentiation medium. To assess cytotoxicity, trypan blue was added to the cultures at 6 dpi and imaged by bright field on a Zeiss microscope. Top panel, prior to addition of trypan blue. Bottom panel, after the addition of trypan blue that allows visualization of virus-induced cytopathic effects. Increased cytopathic effect is seen in cell infected with the Sydney HuNoV but not with the MDA HuNoV compared to the control negative stool.
Figure 3:
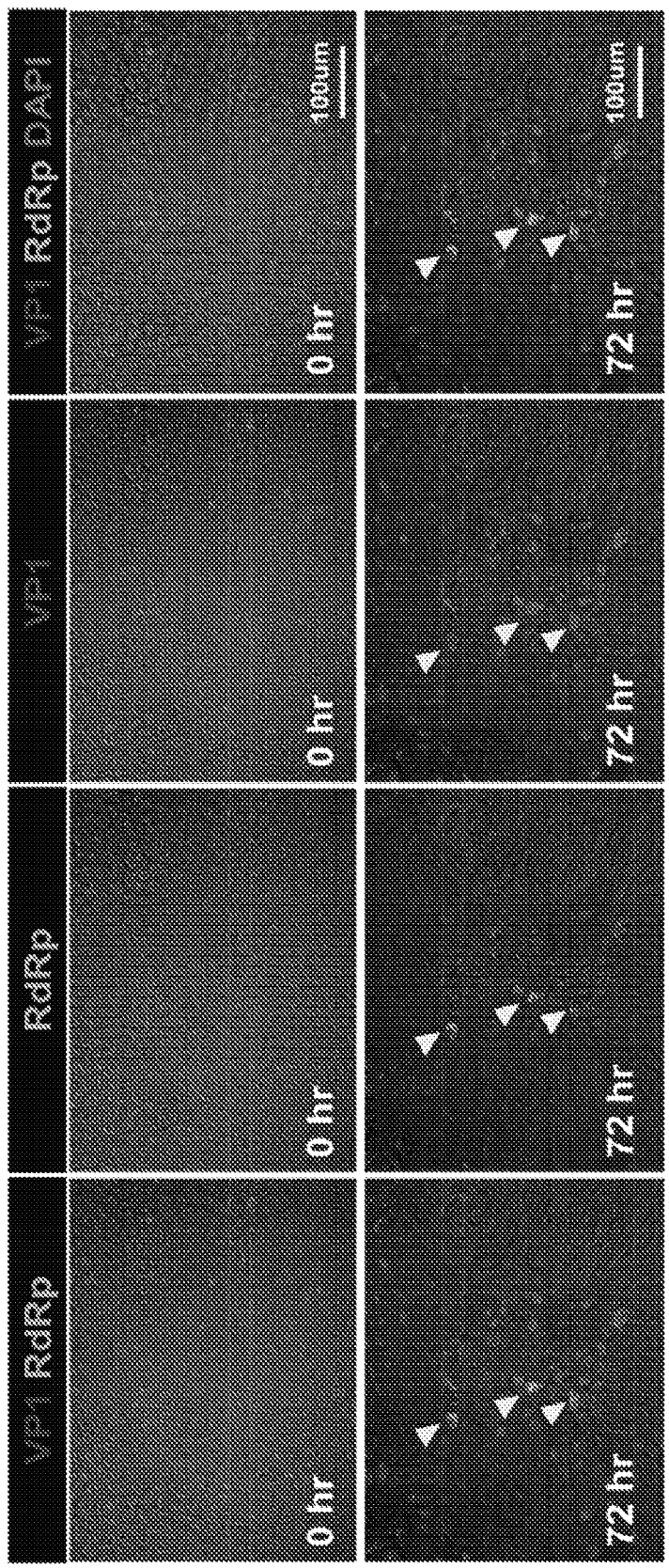
FIG. 3. Detection of norovirus structural and nonstructural proteins in GII.4-infected human intestinal enteroids. Monolayers of human jejunal enteroids were infected with GII.4_2012 (Sydney) virus for 1 hour at 37° C. and then the monolayers were washed twice. One set of monolayers was fixed with methanol (top panel, 0 hpi) and media was added to another set of infected monolayers, which was fixed at 72 hpi (bottom panel). Expression of the capsid protein (VP1) and a non-structural protein [(RNA-dependent RNA polymerase (RdRp)] was detected using antibodies raised against GII.4_2012 (Sydney) virus-like particles (VLPs) in guinea pigs (red, anti-VP1, 1:100) or raised against GII.3 HuNoV RNA-dependent RNA polymerase in rabbits (green, RdRp, 1:100). Nuclei are detected with DAPI (4′,6-diamidino-2-phenylindole; blue). Arrows indicate cells expressing both VP1 and RdRp.

Infection results in cytopathic changes in the infected monolayer (FIG. 2). Infection can be monitored by detection of viral structural and nonstructural proteins by immunofluorescence microscopy and demonstrates approximately 30-40% of the cells are infected (FIG. 3). Detection of viral antigen by confocal microscopy shows differential localization of both the capsid protein VP1 and the NTPase nonstructural protein in different cells (FIG. 4). These results indicate this robust system can be used to define what cell types in the HIEs are infected as well as delineate cellular processes that HuNoVs co-opt for viral replication and for induction of pathogenesis.

Figure 5:
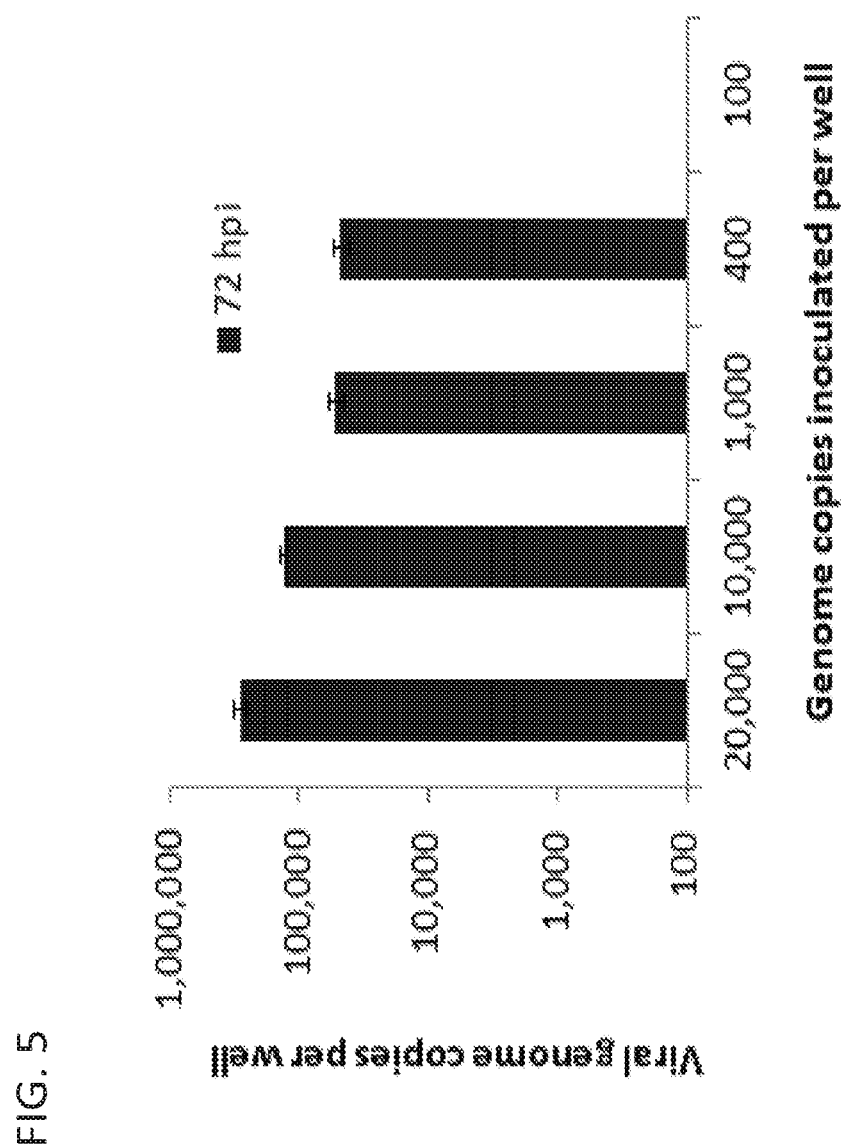
FIG. 5. Determination of the minimal infectious dose of HuNoV. To determine the minimal infectious dose of GII.4_2012 (Sydney) virus, virus-containing stool filtrate was diluted to the indicated genome copies and inoculated onto human J2 enteroids. At these dilutions of virus, the amount of virus bound at 0 hpi is below the limit of detection by qRT-PCR. At 72 hours post infection, the cells and media were harvested, RNA was extracted and viral genomic copies quantified by qRT-PCR. Data represent the mean of three biologic replicates in individual wells quantified by qRT-PCR in duplicate and the error bars denote standard deviation.

As few as 400 genomic copies of HuNoV are infectious. The minimal infectious dose of HuNoV in humans has been estimated to range from 20 to several thousand particles, depending on the study and corresponding modeling assumptions (2, 21). The minimal infectious dose using the enteroid infection model is approximately (<400) genome equivalents of the GII.4_2012 (Sydney) virus (FIG. 5). This result indicates that this model system is amenable to determining the infectivity of low levels of virus, such as that shed from patients at later time points after infection, from 6 to 55 days in acutely-infected patients or for years in chronically-infected individuals, in vomitus that has a median of 41,000 genomic equivalents of HuNoV per ml of vomitus, and in contaminated water or food, such as shellfish (2). This model system will allow evaluation of whether virus currently detected by measuring the viral genomic RNA (by qRT-PCR or other methods) is detecting infectious virus and provide a way to test and identify products that pose a risk to human health.

Figure 6A:
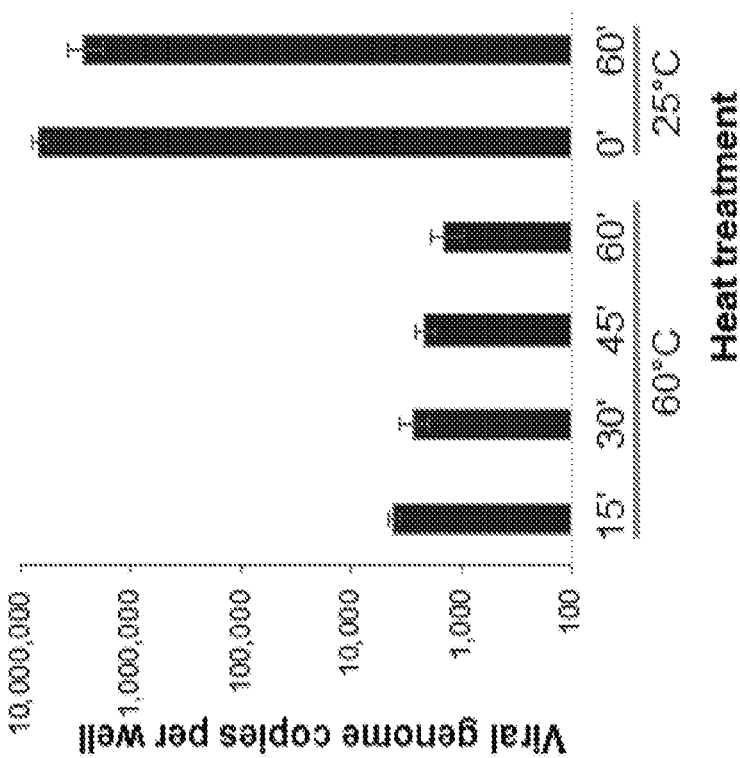
FIGS. 6A-6B. Infectious GII.4_2012 (Sydney) virus is inactivated by gamma irradiation and heat treatment. (6A) GII.4_2012 (Sydney) virus was irradiated or incubated overnight at room temperature. (6B) Three replicates of GII.4_2012 (Sydney) virus were heat-inactivated at 60° C. for the indicated time points. Two other aliquots of virus were incubated at room temperature for 0 and 60 minutes. Human jejunal enteroid monolayers were infected with each sample and then cells and media were harvested at the indicated times post-infection. RNA was extracted and the viral genome copies per well quantified by qRT-PCR. Data represent the mean of three wells quantified by qRT-PCR in duplicate and the error bars denote standard deviation.
Figure 6B:
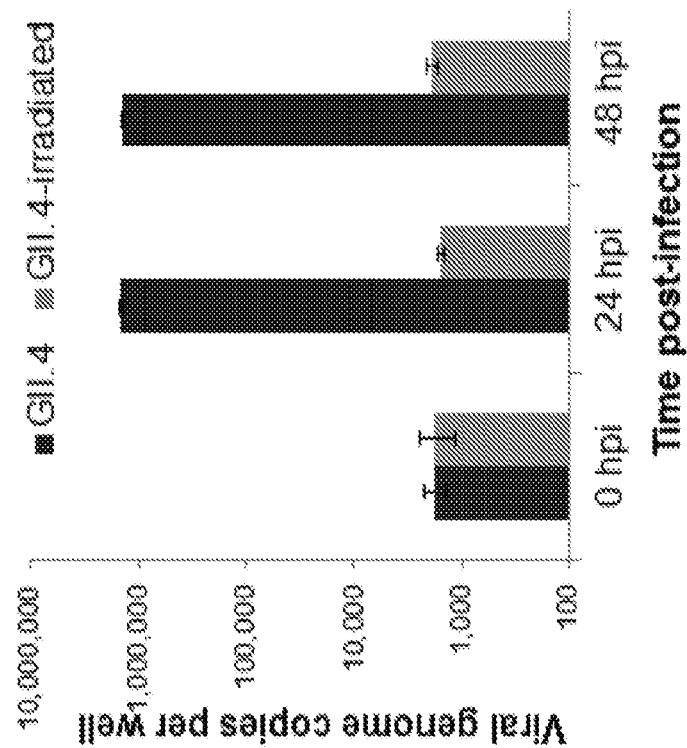

HuNoV is inactivated by gamma irradiation and heat. Another advantage of this cultivation system is the ability to evaluate environmental conditions and inactivation treatments on virus infectivity. FIGS. 6A and B demonstrate that HuNoV is inactivated by gamma irradiation and heat treatment, respectively. These studies indicate HuNoV infection of enteroids will allow discovery of new methods to inactivate HuNoVs and to measure the effectiveness of disinfectants and sanitizers, including characterization of the efficacy of both traditional and novel control measures.

Figure 7:
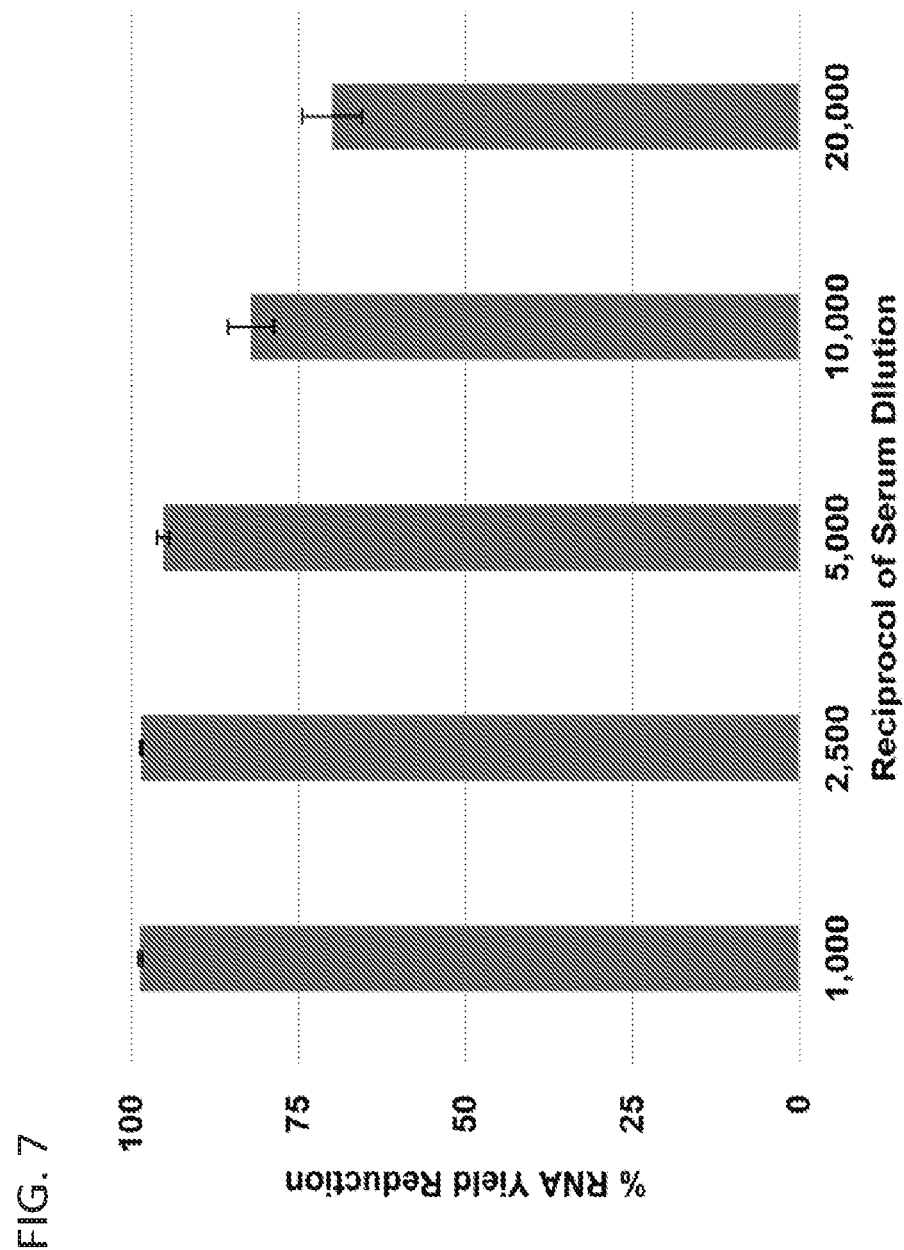
FIG. 7. Human serum neutralizes HuNoV. $2.5 \times 10^5$ copies of GII.4_2012 (Sydney) virus were incubated in 50 µl of diluted human serum, which has a histoblood group antigen-virus blocking antibody titer of 671, or PBS for 1 hour at 37° C. The volume was then brought to 100 µl by adding 50 µl CMGF(−) basal medium for the final indicated serum dilutions. Human jejunal enteroid monolayers were infected with each sample and then cells and media were harvested at the indicated times post-infection. RNA was extracted and the viral genome copies per well quantified by qRT-PCR. Data represent the mean of three wells quantified by qRT-PCR in duplicate and the error bars denote standard deviation. Yield reduction is relative to 0% neutralization data from control PBS plus virus samples.
Figure 8A:
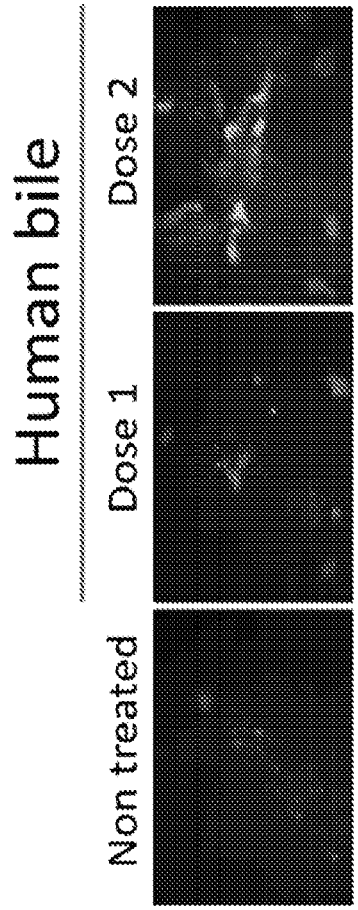
FIGS. 8A-8F. Human bile enhances GII.4 HuNoV replication. J2 human intestinal enteroid monolayers were treated with media (non-treated) or media containing 1% (dose 1) or 10% (dose 2) human bile for 2 days during differentiation. The monolayers were infected with GII.4_2012 (Sydney) (8A, 8C and 8E) or GII.4_2006b (MDA) (8B, 8D and 8F). (8A and 8B) Non-treated or treated, infected monolayers were fixed with methanol at 72 hpi and VP1 (green) detected by immunofluorescence and the number of infected cells were quantified (8C and 8D). (8E and 8F) The viral genome copies per well were quantified by qRT-PCR [0 hpi (light blue bars) and 48 hpi (dark blue bars)]. Data represent the mean of three wells quantified by qRT-PCR in duplicate and the error bars denote standard deviation. An unpaired student t-test showed a significant difference between 1% or 10% human bile treated verses non-treated with $p<0.01$ (student t test) for both GII.4 viruses.
Figure 8B:
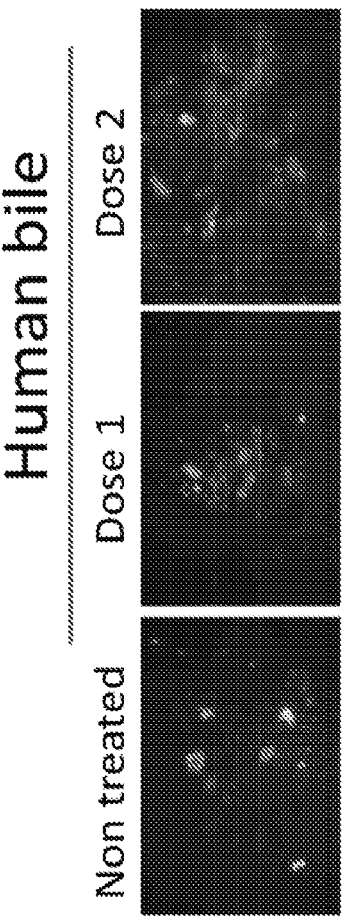
Figure 8C:
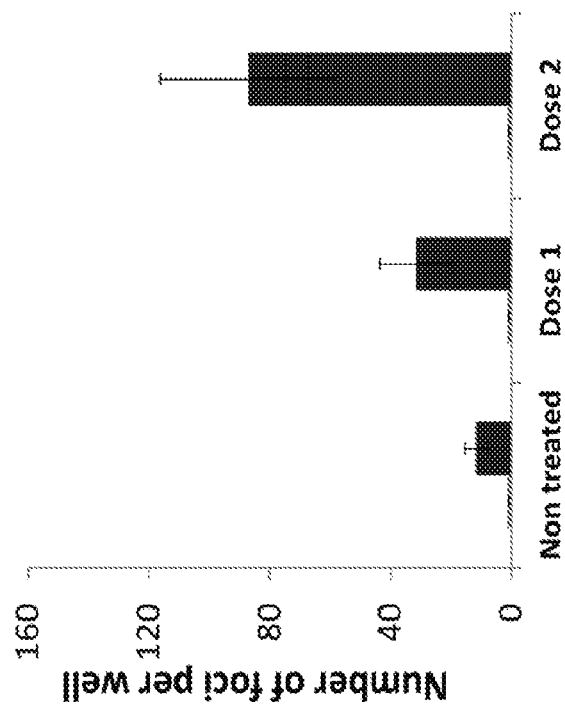
Figure 8D:
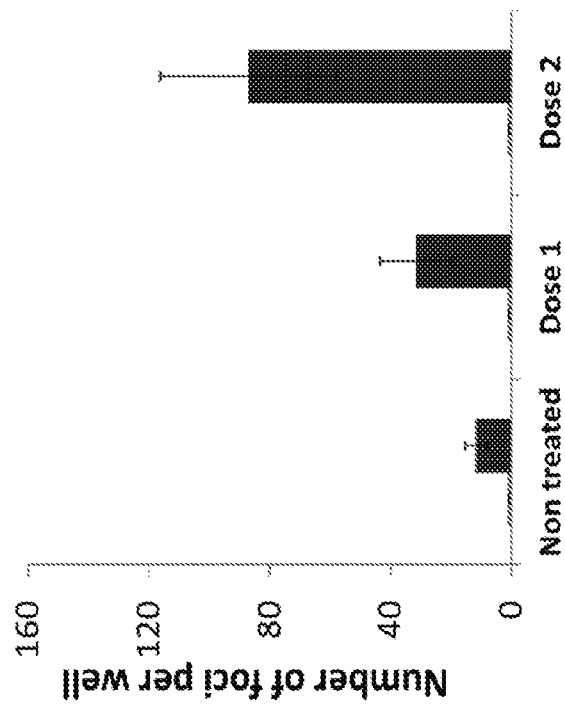
Figure 8E:
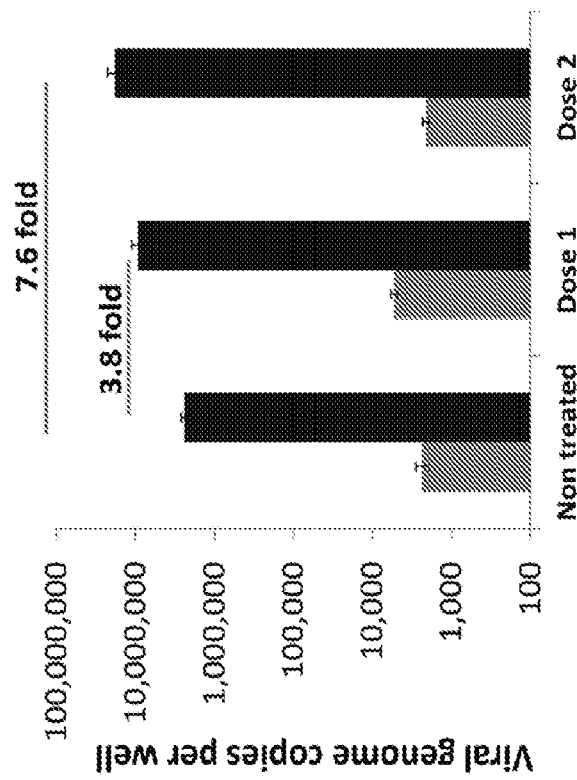
Figure 8F:
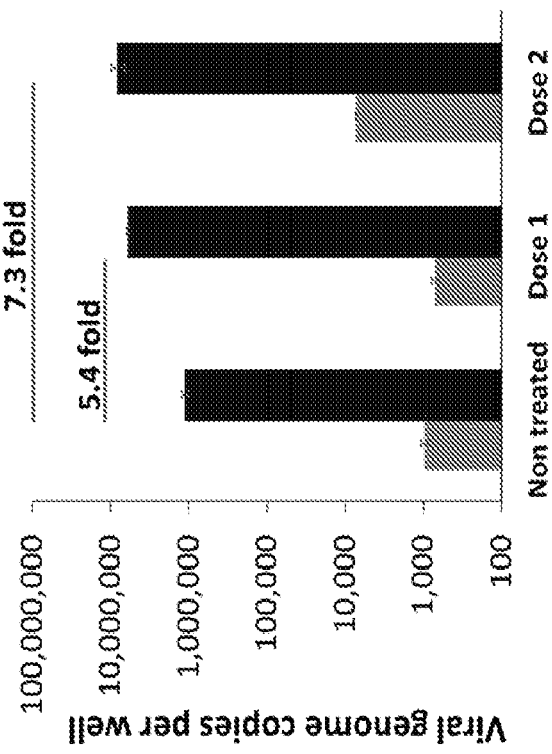

Serum HuNoV neutralization titer is higher than the glycan blocking titer. Host genetic resistance to human norovirus has been observed in challenge and outbreak studies. The lack of a functional fucosyltransferase 2 (FUT2) that transfers fucose to a histo-blood group (HBGA) precursor in gastrointestinal cells provides certain humans and animals high protection from infection from most HuNoVs. We previously discovered a correlate of protection against clinical HuNoV gastroenteritis using a HBGA-blocking assay that examines the ability of human serum to block the interaction of HuNoV virus-like particles with H type 1 and H type 3 glycans (1, 13). Due to the prior lack of an in vitro cultivation system, this assay has been used as surrogate for virus neutralization. Virus neutralization gives the measure of how much or how effective the antibody present in serum is in reducing infectivity by 50% compared to virus incubated in no serum or buffer alone. The new cultivation system can be used to measure direct neutralization activity in serum samples. Using a human serum with a GII.4 HuNoV HBGA-blocking titer of 671, we now show that this same serum, at a dilution of 1:20,000 reduces the yield of virus by 70% as assessed by a decrease in genomic RNA copies (FIG. 7). This result, showing that the same serum, which blocks virus-HBGA binding by 50% at a dilution of 1:671 and neutralizes or reduces virus infectivity by 70% at a dilution of 1:20,000 (the serum requires further dilution to obtain a 50% reduction in infectivity), suggests virus neutralization is a more sensitive assay than the HBGA blocking assay. This model system will aid in the development and use of assays to measure protective neutralizing antibodies conferred either by natural or vaccine-induced immunity and allow broadly reactive neutralizing antibodies to be measured. Neutralization epitopes on the virus capsid can also be identified and the involvement of other HuNoV proteins in neutralization can also be tested.

Figure 9A:
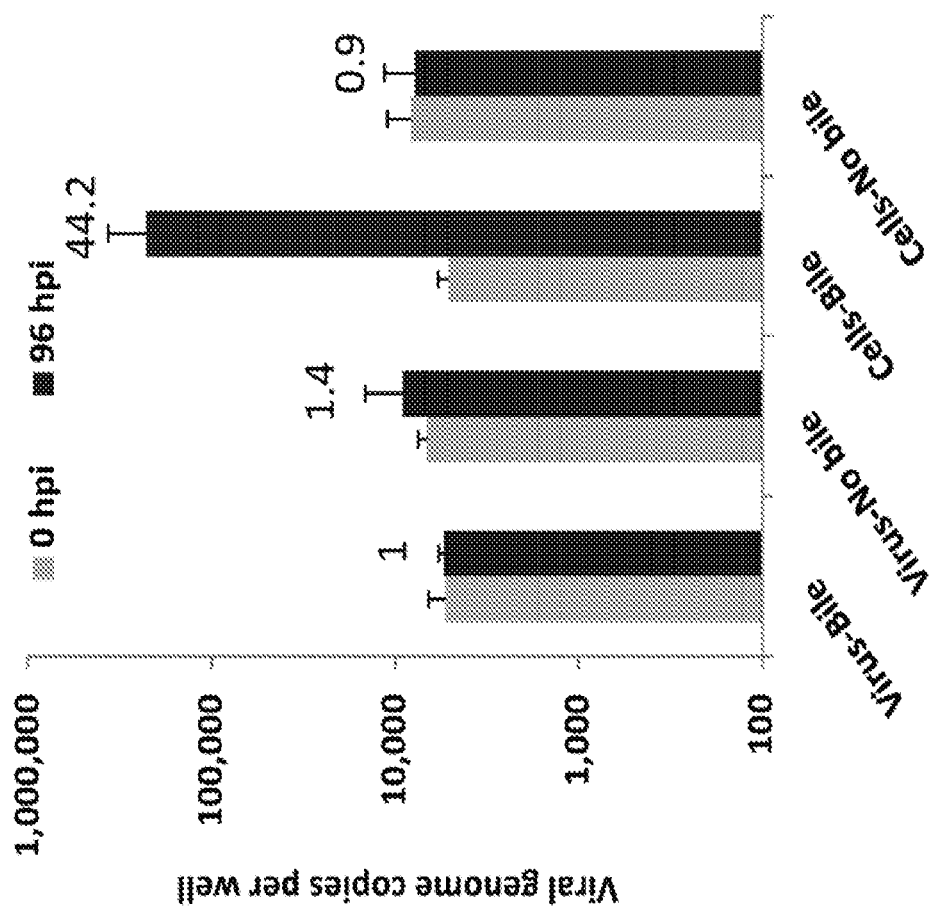
Figure 9C:
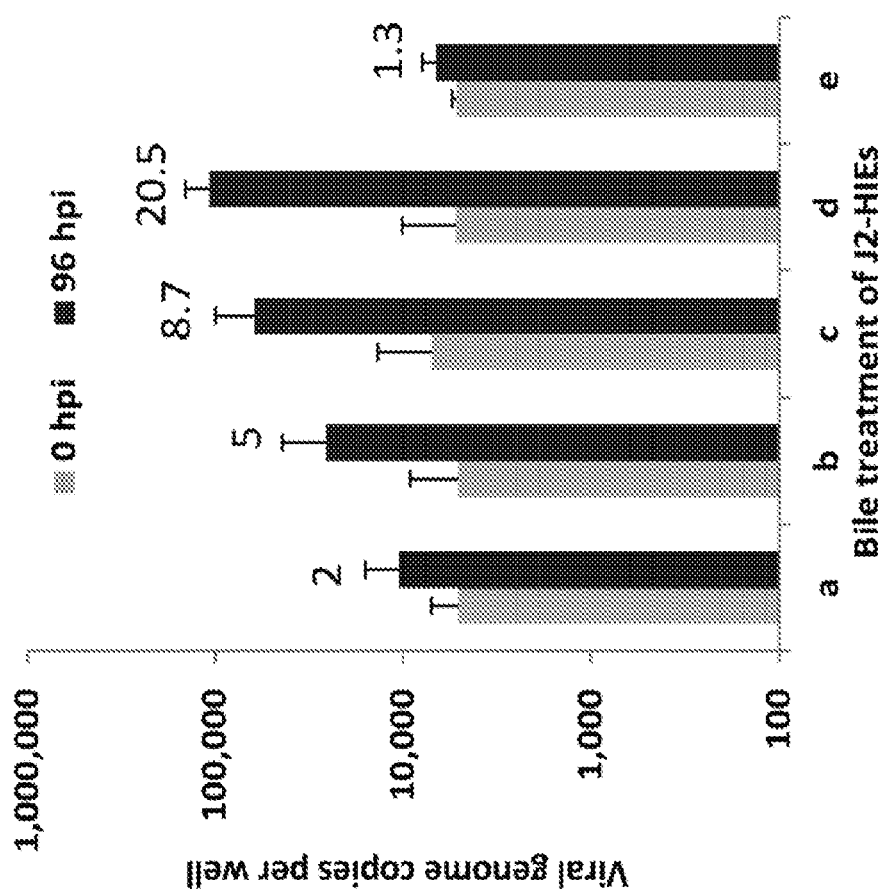

Bile enhances GII.4 and is required for GII.3 HuNoV replication. Bile from humans, pigs and bovines have been tested for their ability to enhance HuNoV infectivity. We found that GII.4 viruses can grow in the absence of bile but the addition of bile enhances the infectivity yield of GII.4 viruses as shown by a fluorescent focus assay and by qRT-PCR (FIG. 8). In contrast, bile is required for the growth of GII.3 HuNoV (FIG. 9). Pretreatment of virus with bile does not enhance infection and replication (FIG. 9A), indicating that the effect of bile is on the cells and not the virus. We next evaluated bile treatment of the intestinal cells prior to, during, and following infection as shown in the schematic (FIG. 9B). Pretreatment of cells alone had little effect on enhancement of infectivity. The greatest enhancement of infectivity was found with treatment prior to, during and after infection (condition d, FIG. 9C). These results indicate bile enhances infectivity but with differing effects on different virus strains. Fractionation experiments are performed to identify the active component(s) in bile that enhances infectivity, and in specific embodiments identification of the active component(s) in bile will further simplify cultivation.

Figure 10A:
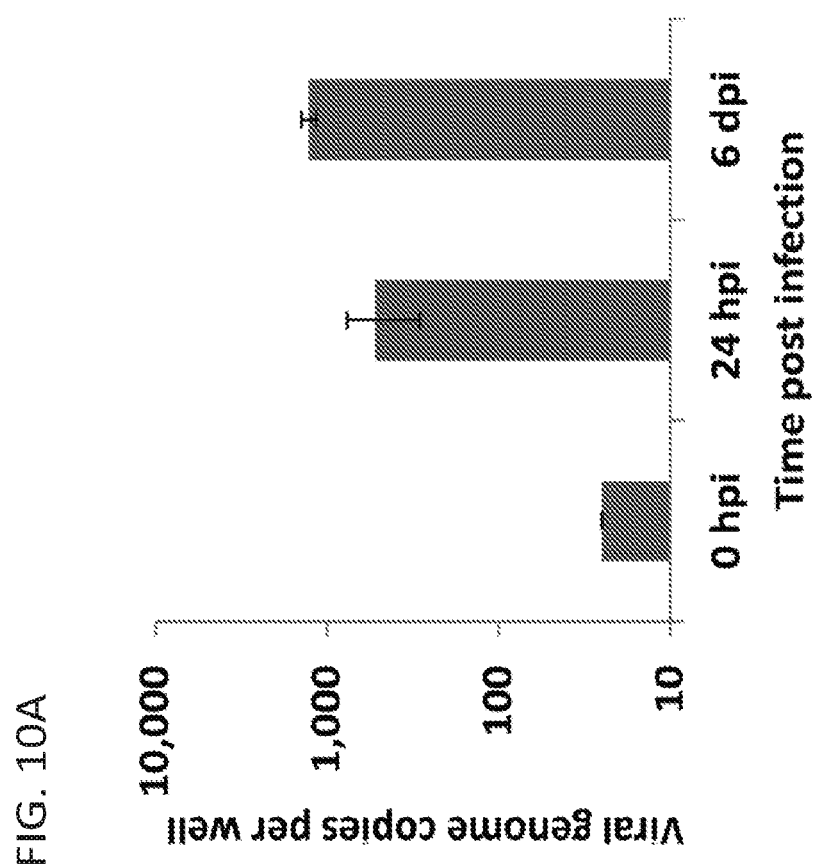
FIGS. 10A-10C. Passaging of HuNoV in human intestinal enteroids. P1 stocks of GII.4_2006b (MDA) ($0.7 \times 10^6$ genome copies) or GII.4_2012 (Sydney) ($1.1 \times 10^6$ genome copies) were inoculated onto intestinal enteroid monolayers and cultured in the presence of bile. RNA was extracted from the cells and media, and the viral genome copies of GII.4 MDA (10A) and GII.4_2012 (Sydney) (10B) per well was quantified by qRT-PCR. (10C) New passage 1 (P1) and P2 stocks of GII.4_2012 (Sydney) virus were prepared. The P2 6 dpi virus stock was then concentrated by ultracentrifugation and passaged on enteroid monolayers to examine replication and generate a P3 stock. Data represent the mean of three wells quantified by qRT-PCR in duplicate and the error bars denote standard deviation.
Figure 10B:
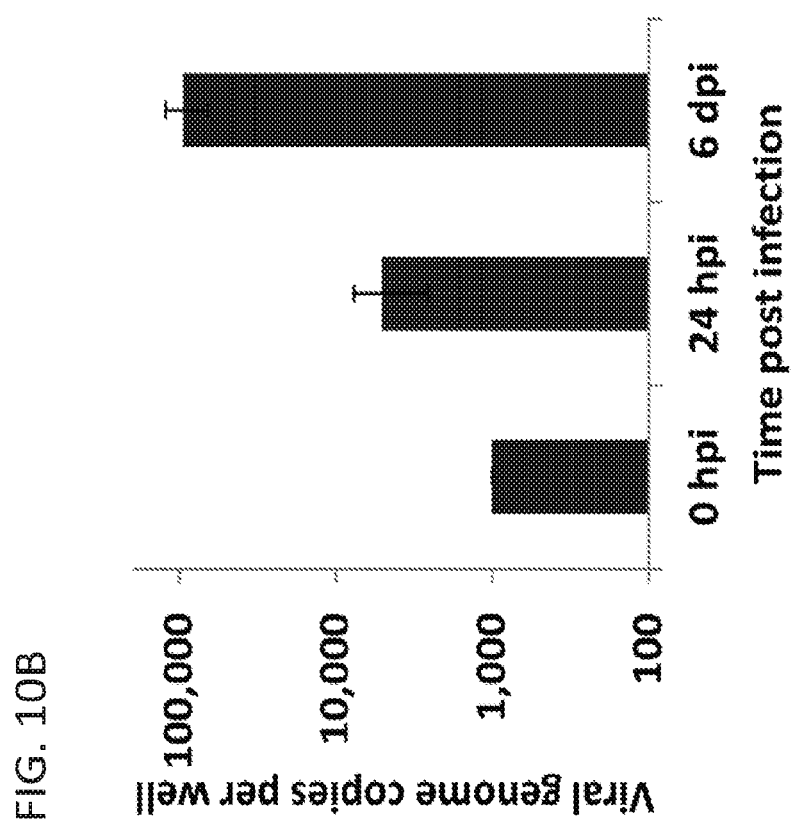
Figure 10C:
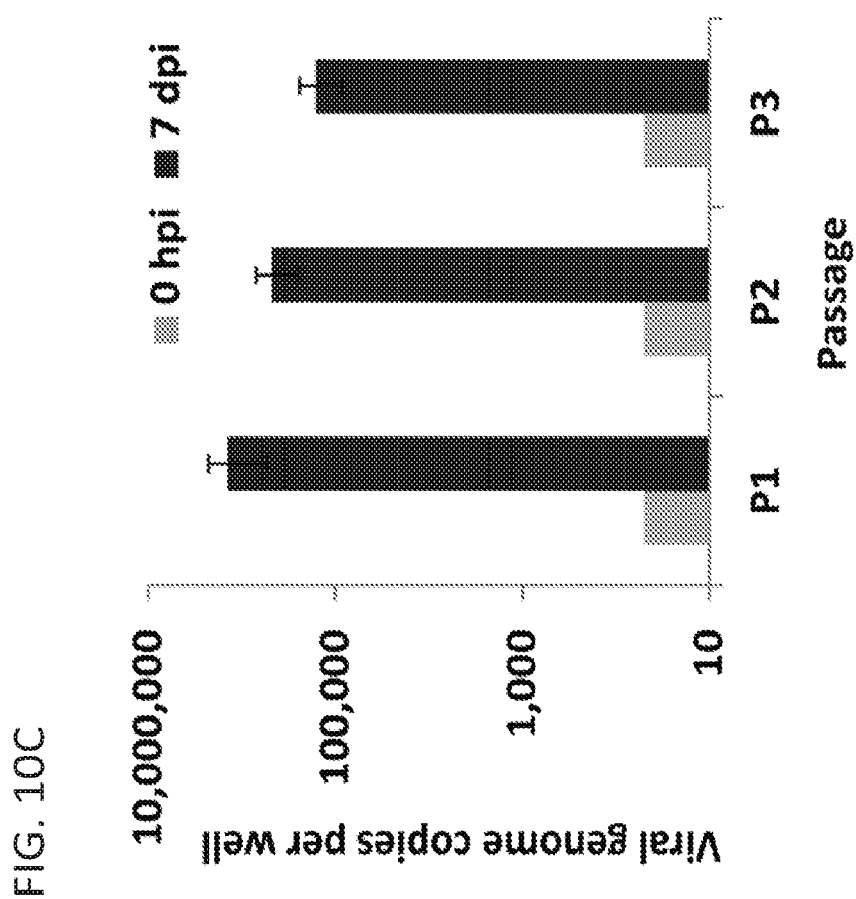

Passaging the GII.4 HuNoVs. Two different GII.4 variants, 2012 (Sydney) and 2006b viruses, have been passaged either in the presence or absence of bile (FIGS. 10A and B, passage 2 in the presence of bile shown). A third passage of the GII.4_2012 (Sydney) strain has been accomplished (FIG. 10C). We are continuing to passage these viruses to generate large pools of virus stocks. Comparative analysis of the nucleotide sequence of the virus in the original stool sample and in passaged stock will allow discovery of whether specific genomic mutations are selected in virus that adapts to continuous cultivation.

Figure 11:
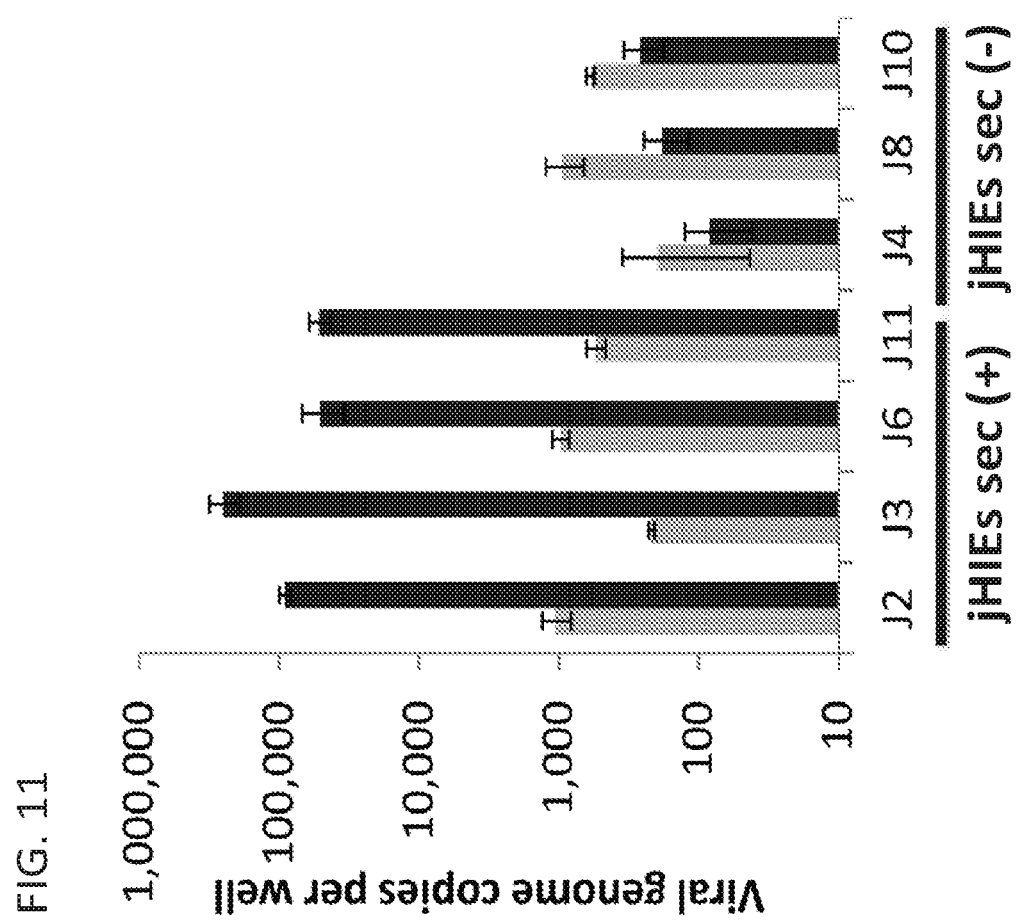
FIG. 11. GII.4_2012 (Sydney) strain replicates in secretor positive but not secretor negative enteroids. Jejunal enteroids from 4 secretor positive [Sec (+)] and 3 secretor negative [Sec (−)] individuals were infected with GII.4_2012 (Sydney) virus in the presence of bile. Cells and media were harvested at 0 (light blue bars) and 7 dpi (dark blue bars), RNA was extracted and the viral genome copies per well quantified by qRT-PCR. Data represent the mean of three wells quantified by qRT-PCR in duplicate and the error bars denote standard deviation, jHIEs, jejunal human intestinal enteroid.
Figure 12:
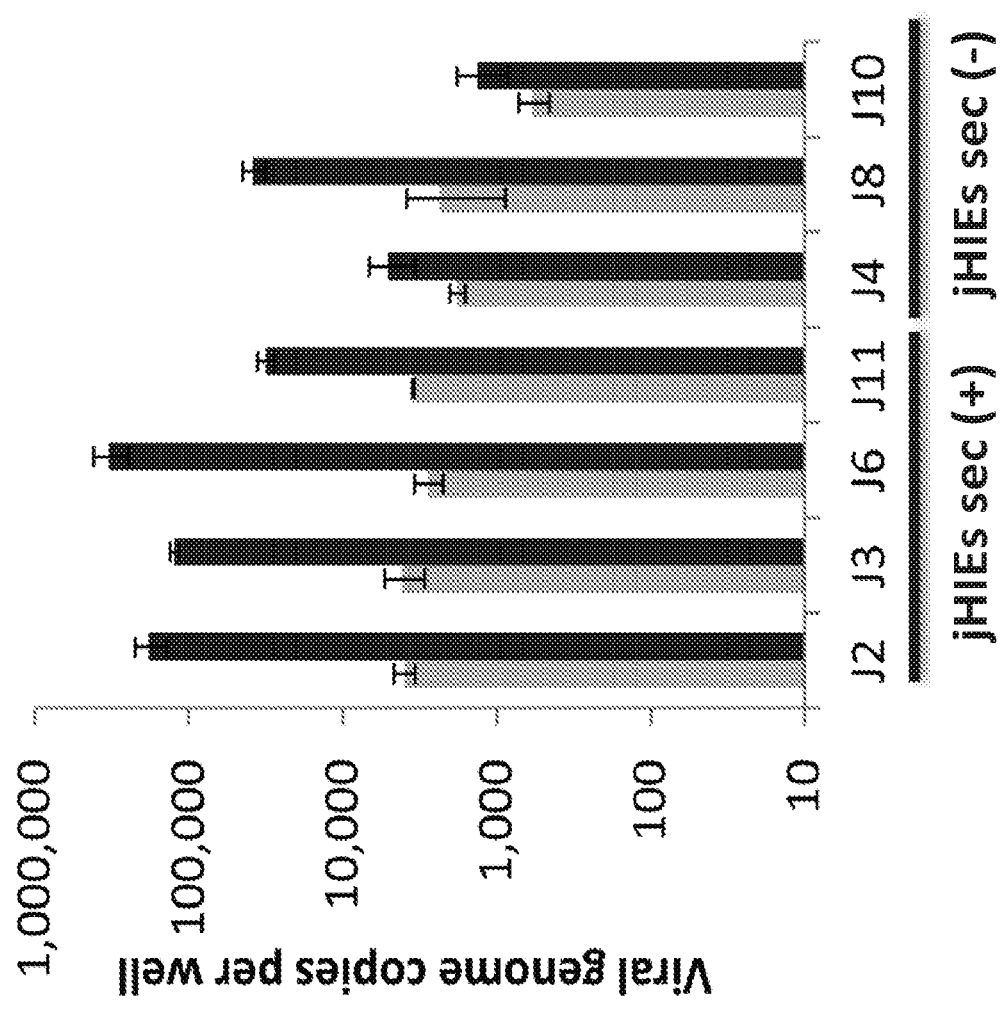
FIG. 12. GII.3 virus replicates in all secretor positive enteroids and in one of three secretor negative enteroids. Jejunal enteroids from 4 secretor positive [Sec (+)] and 3 secretor negative [Sec (−)] individuals were infected with a GII.3 virus in the presence of bile. Cells and media were harvested at 0 (light blue bars) and 7 dpi (dark blue bars), RNA was extracted and the viral genome copies per well quantified by qRT-PCR. Data represent the mean of three wells quantified by qRT-PCR in duplicate and the error bars denote standard deviation. Replication of GII.3 in J8 and J4 HIEs was confirmed in additional experiments (see FIG. 18C).
Figure 13:
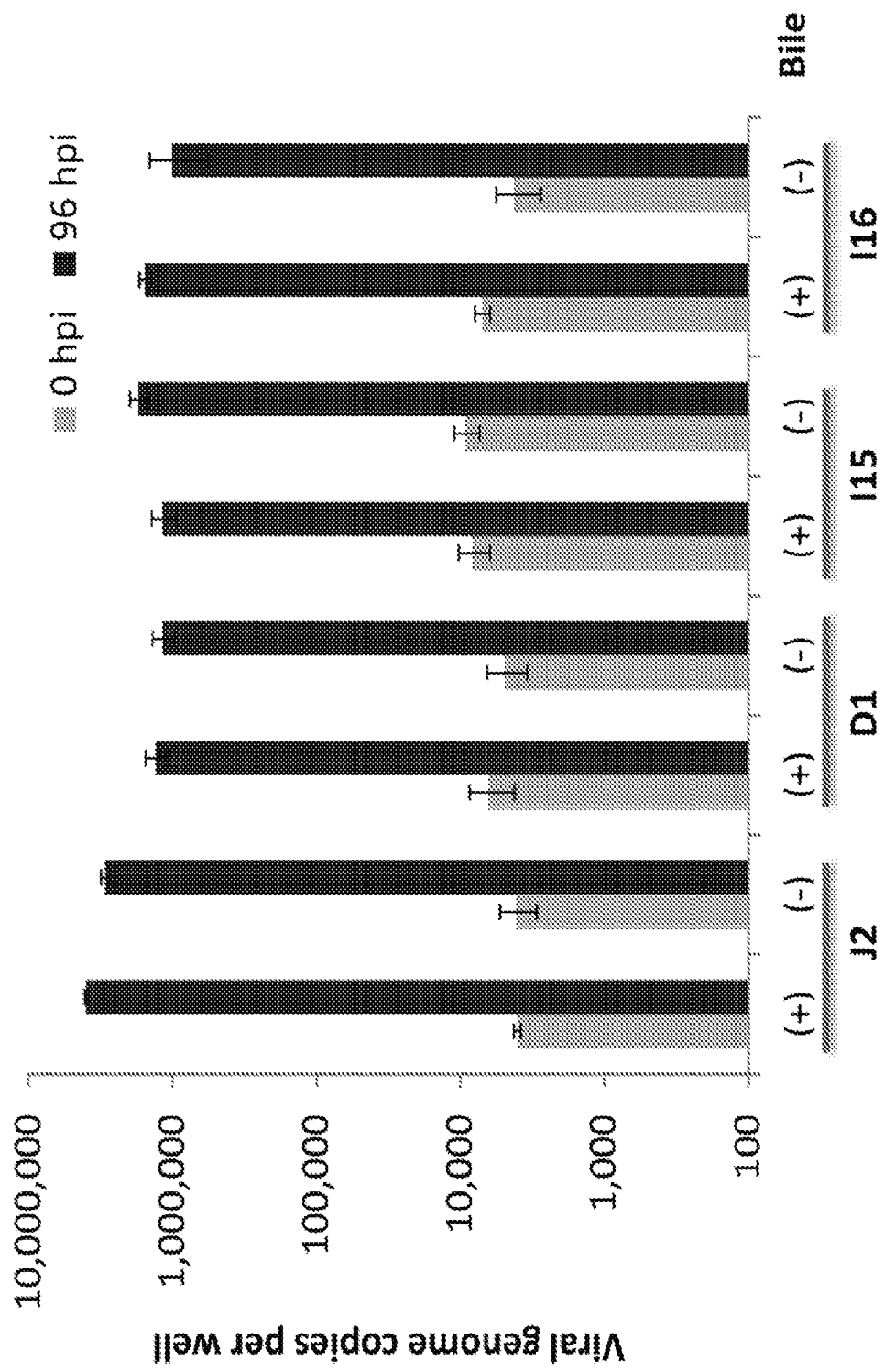
FIG. 13. GII.4 HuNoV replicates in human enteroids generated from different intestinal segments. Jejunal (J2), duodenal (D1), and ileal (I15 and I16) enteroids were infected with GII.4_2012 (Sydney) in the presence (+) or absence (−) of bile. Cells and media were harvested at 0 and 96 hpi, RNA was extracted and the viral genome copies per well quantified by qRT-PCR. Data represent the mean of three wells quantified by qRT-PCR in duplicate and the error bars denote standard deviation.

GII.3 but not GII.4 HuNoVs infect a secretor negative enteroid line. Because we and others have shown that human susceptibility to infection by some HuNoV genotypes is linked to the genetically determined expression of HBGAs, we tested the infectivity of both GII.4 and GII.3 viruses in enteroids generated from secretor positive (functional FUT2) and secretor negative (nonfunctional FUT2) individuals. Because we found that bile enhances the infectivity of both GII.4 and GII.3 viruses, enteroids were infected and maintained in the presence of bile. GII.4_2012 (Sydney) virus replicated in enteroids from secretor positive [Sec (+)] but not secretor negative [Sec (−)] individuals (FIG. 11). In contrast, GII.3 virus replicated in all 4 Sec (+) enteroid lines as well as in one of the Sec (−) enteroid lines (a 1 log 10 increase) (FIG. 12, J8 enteroid line). In addition, the GII.4_2012 (Sydney) HuNoV replicates in human enteroids generated from different intestinal segments (FIG. 13). These results indicate HuNoV infectivity in enteroids is a biologically relevant system. They also indicate that enteroids generated from individuals with different genetic backgrounds will aid in the establishment of improved diagnostic and infectivity assays that may be slightly different for different virus strains.

Summary. The results demonstrate the first culture system for HuNoVs in human intestinal cells in enteroid cultures that overcomes the single most important limitation for the study of HuNoVs, the lack of an in vitro cultivation method. Infection with multiple HuNoV strains, including GI.1, GII.4 variants, GII.3 and GII.17 strains, results in robust replication and progeny virus that can be passaged. Cultivation of these strains is significant because they are the predominant ones currently causing human gastrointestinal disease worldwide. This robust system can be used to define cellular processes and pathways HuNoVs exploit for infection and replication as well as for induction of pathogenesis. Demonstration that the minimal amount of HuNoV is <400 genome copies, a value well within the reported dose required to cause disease in human subject trials, indicates that this model system will allow evaluation of whether virus detected by measuring viral RNA (by qRT-PCR or other methods) is detecting infectious virus and provides a way to identify products and/or individuals that pose a risk to human health. In addition, methods to inactivate HuNoVs and to measure the effectiveness of disinfectants and sanitizers can be readily assessed in this system. Other benefits include the development and use of assays to measure protective neutralizing antibodies conferred either by natural or vaccine-induced immunity and to understand host genetics in HuNoV evolution. The ability to grow HuNoV will aid in the development of a live attenuated HuNoV vaccine that may provide longer-lasting immunity than the current virus-like particle vaccine currently in clinical trials. It will also facilitate development or antivirals and other therapeutics, including protease inhibitors, polymerase inhibitors and immune serum globulin and neutralizing and non-neutralizing monoclonal antibodies, for example.

Example 2

Cultivation Embodiments Utilizing Bile

Bile was reported not to enhance the replication of the sapovirus, porcine enteric calicivirus (Flynn and Saif, 1988) and tauroursodeoxycholic acid did not enhance the replication of porcine enteric calicivirus (Chang et al., 2004). However, embodiments of the cultivation system of the present disclosure utilizes bile or a functionally active fraction thereof to cultivate Caliciviruses such as HuNoV.

Bile from humans, pigs and bovine were tested for their ability to enhance HuNoV infectivity. Bile from each of these sources is required for GII.3 replication. Bile from three different sows used at a 1% concentration allows GII.3 replication. Infection in the presence of a commercially available bovine bile at 0.1%, 0.05% and 0.01% results in yields similar to those obtained in the presence of 5% human bile.

One can determine the active component in bile that allows GII.3 (as an example) replication. To begin to evaluate the components in bile that enhance HuNoV replication, several studies were performed to determine whether a lipid micelle or a protein is the active component. To determine whether the component is in a lipid micelle, human bile was sonicated 3 times for 1 minute or 1 time for 5 minutes (for example). Compared to replication with 5% human bile, the yield of GII.3 viral genome copies was not changed in the presence of the sonicated human bile. To determine whether the component is a protein, trypsin-treated or heat-treated human bile were tested; no change in replication enhancement was seen with these treatments. To determine whether the component is a lipid or cholesterol, bovine bile was extracted twice overnight with chloroform:methanol and growth of GII.3 was evaluated in the presence of (i) untreated bovine bile, (ii) the aqueous phase after extraction that should contain bile acids, and (iii) the organic phase that should contain sterols such as cholesterol, lipids and fatty acids. GII.3 grew to a similar level in the presence of each of these fractions. Therefore, in at least some embodiments of the disclosure, there are one or more components in bile, in addition to bile acids that are in the aqueous phase, that allow GII.3 replication.

One can analyze these samples by mass spectroscopy to determine the bile acid, lipid, fatty acid and/or cholesterol content. Bile was also fractionated based on filtration through different molecular cut-off filters. GII.3 grew well in the presence of high molecular weight material, greater than 100,000 molecular weight cut-off whereas, GII.4 grew well in material that passed through the 100,000 molecular weight cut-off filter. These results suggest that GII.3 and GII.4 require different components for replication, in at least some embodiments.

Figure 14:
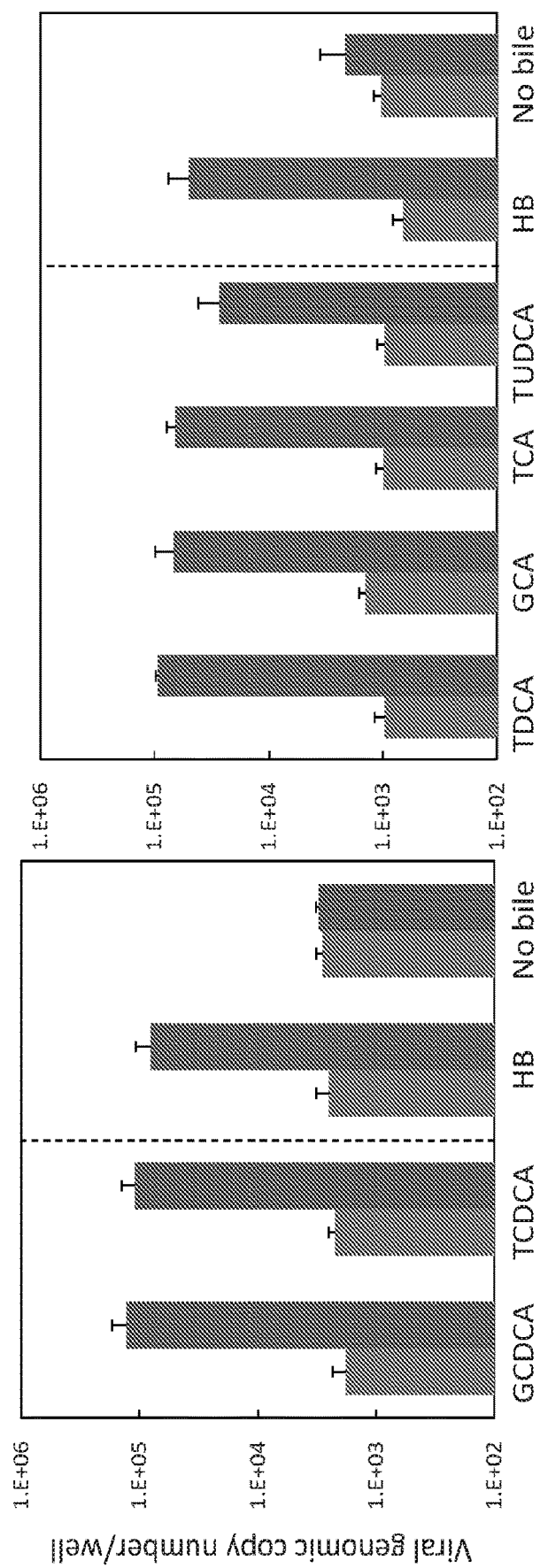
FIG. 14. Bile acids are an active component of bile that enhance HuNoV GII.3 replication. Abbreviations for additives: GCDCA (Glycochenodeoxycholic acid); TCDCA (Taurochenodeoxycholic acid); TDCA (Taurodeoxycholic acid); GCA (Glycocholic acid); TCA (Taurocholic acid); TUDCA (Tauroursodeoxycholic acid); HB (human bile).

FIG. 14 illustrates that bile acids are an active component of bile that enhance HuNoV GII.3 replication. Monolayers of J2 enteroids were infected with TCH04-577 GII.3 HuNoV in the presence of each additive in CMGF(−) media. At 72 hours post infection, the cells and media were harvested and viral RNA was quantified by qRT-PCR. Each bile acid was added at a concentration of 0.5 mM. One can also assay other bile acids and combinations of bile acids using these methods or others in the art.

Additional bile acids to those described in FIG. 14 were also tested, and all results are summarized in Table 2. This table also shows that two exemplary bile acids that enhanced porcine enteric calicivirus growth do not enhance GII.3 HuNoV replication. One bile acid tested increased HuNoV but not PEC replication. It also demonstrates that GCDCA bile acid can enhance GII.4 replication.

TABLE 2

Yield of GII.3 HuNoV in the presence of bile acids.

| Bile Acid | Concentration (uM)[1] | Fold increase in viral genome copies compared to no bile (0-72 hpi) | PEC growth[2] |
|---|---|---|---|
| human bile | 5% | 40-75 | ND[3] |
| CA | 500 | 49-63 | + |
| CDCA | 100 | no increase | + |
| GCDCA | 500 | 71-106 | + |
| TCDCA | 500 | 48-103 | + |
| GCA | 500 | 48 | + |
| TCA | 500 | 65 | + |
| TDCA | 500 | 95 | + |
| GDCA | 500 | 160 | + |
| TLCA | 500 | 268 | + |
| DCA | 100 | no increase | + |
| UDCA | 500 | no increase | − |
| TUDCA | 500 | 27 | − |
| LCA | | ND | + |

[1]Concentration used for GII.3 growth.
[2]Chang et al., PNAS 2004
[3]ND—not done
Difference in growth between HuNoV and PEC.

An example of an enteroid maintenance protocol is provided below, although the skilled artisan recognizes that specific reagents and/or steps, for example, may be modified and still provide a useful system.

Exemplary Reagents (all Stock Solutions and Aliquot are Stored in −20° C. Matrigel is Aliquoted and Stored in −20° C.)

| Reagent name | Solvent | Stock solution | final conc |
|---|---|---|---|
| Matrigel, GFR, phenol free | | | |
| GlutaMAX-I | | 200 mM | 2 mM |
| Penicillin/Streptomycin | | 100X | 1x |
| N2 supplement | | 100x | 1x |
| B27 supplement | | 50x | 1x |
| N-Acetylcysteine | dd H$_2$O | 500 mM | 1 mM |
| mouse recombinant EGF | PBS | 50 microg/ml | 50 ng/ml |
| A-83-01 | DMSO | 500 microM | 500 nM |
| SB202190 | DMSO | 10 mM | 10 microM |
| Nicotinamide | ddH$_2$O | 1M | 10 mM |
| [Leu15]-Gastrin I | PBS | 10 microM | 10 nM |
| HEPEs 1M | | 1M | 10 mM |
| Advanced DMEM/F12 | | | |
| Recovery Cell Freezing Media | | | |

Equipment

| | Cat No. |
|---|---|
| 24 well Nunclon delta surface tissue culture dish | Thermo Scientific 142475 |
| Refrigerated centrifuge with swing rotor | |
| Sterilized filter pipette tips | |
| BD 1 ml TB syringe | 309626 |

Enteroid Medium:

CMGF− (Complete Media without Growth Factor): Keep at 4° C. for Up to 4 Weeks
  500 ml Advanced DMEM/F12 (contains albumin, and ITS)
  5 ml Glutamax 100×
  5 ml HEPES 1M
  5 ml Pen/Strep CMGF+(complete media with growth factor): keep at 4° C. for up to 2 weeks, amount listed are for 10 ml:
  1.5 ml CMGF−
  5 ml Wnt 3 conditioned media
  200 ul B27 (50×)
  100 ul N2 (100×)
  20 ul n-acetylcysteine (500 mM)
  2 ml Rspo-1 conditioned medium
  1 ml Noggin
  10 ul EGF (1000× final conc. 50 ng/ml)
  10 ul Gastrin (1000× final conc. 10 nMI)
  100 ul Nicotinamide (final conc. 10 mM)
  10 ul A83 (TGFb type I receptor inhibitor) (1000× final conc. 500 nM)
  10 ul SB202190 (P38 inhibitor) (1000× final conc. 10 uM)

Differentiation Media:
CMGF+ without Wnt 3a, Nicotinamide and SB202190, reduce R-Spondin and Noggin, conditioned medium to half of the concentration Revive Enteroids from LiN$_2$
 1. Thaw matrigel aliquot overnight at 4° C.
 2. Add 10 ml of CMGF− into 15 ml corning tube, leave tube on ice
 3. Transfer frozen vial containing entroids from LiN$_2$ to dry ice
 4. Hold vial under room temperature tap water till ice detaches from the vial wall
 5. Transfer contents in the vial to 15 ml tube containing 10 ml cold CMGF− using 2 ml pipet
 6. Spin down in refrigerated swing rotor centrifuge at 80 g at for 5 min at 4° C.
 7. Take off medium and leave 15 ml tube containing enteroids pellet on ice. Resuspend pellet in 120 ul matrigel (enough to seed 4 wells, 30 ul/well) using cold P200 pipet tips, plate enteroids as droplets in 4 wells of 24 well plate and transfer plate to 37° C. incubator. Let gel settle for 5-10 minutes, add 500 ul of room temperature CMGF+ to each well and culture in 37° C. incubator.
 8. Refresh culture with CMGF+ every other day until it's ready to be passaged.

Passage Enteroids (Usually 1:5, Following Protocol is for One Well Only, Repeat with Other Wells)
 1. Usually after 6-7 days, enteroids are ready to be passaged
 2. Remove medium from wells (around the solid Matrigel) with P1000 pipet
 3. Add 500 ul cold CMGF− to well and mechanically break up Matrigel with pipetting P1000 up and down couple of times
 4. Then using 1 ml syringe with needle 25G×⅝, up and down 3-4 times in each well, then transfer whole contents into 15 ml tube (if you have more wells to passage, you can combine wells into same tube), add 2× more cold CMGF−
 5. Spin down in refrigerated swing rotor centrifuge at 80 g at for 5 min at 4° C.
 6. Remove all medium. Keep tube on ice.
 7. Resuspend entroids pellet in Matrigel (calculate the amount of matrigel you will need, 30 ul/well) using cold P200 pipet tips.
 8. Pipet 30 ul/well of enteroids matrigel mixture as droplet into 24 well plate using cold P200 pipet tips. Transfer plate into 37° C. incubator. Let gel settle for 5-10 minutes, add 500 ul of room temperature CMGF+ to each well and culture in 37° C. incubator.
 10. Refresh culture with CMGF+ every other day.

Freeze Enteroids (Usually After 6-7 Days in Culture, Combine Two Wells of Enteroids into 1 Cryovial)
1. Usually after 6-7 days, enteroids are ready to be passaged.
2. Remove medium from wells (around the solid Matrigel) with P1000 pipet
3. Add 500 ul cold CMGF- to well and mechanically break up Matrigel with pipetting P1000 up and down couple of times
4. Spin down in refrigerated swing rotor centrifuge at 80 g at for 5 min at 4° C.
5. Remove all medium. Keep tube on ice.
6. Resuspend enteroids into freezing medium (each cryovial using 500 ul) at original ratio of 2 wells into 1 vial
7. Keep cryovial into cell freezing container and keep in −80c for at least overnight. Next day transfer vials into LiN2

Enteroids Differentiation

Usually after 4 days in culture, switch CMGF+ to differentiation medium for 3-5 days, refresh medium every other day.

Example 3

Replication of Human Noroviruses in Stem Cell-Derived Human Enteroids

Introduction—

Human noroviruses (HuNoVs) are the most common cause of epidemic and sporadic cases of acute gastroenteritis worldwide, and the leading cause of food-borne gastroenteritis (Ramani, et al., 2014; Ahmed, et al., 2014; Hall, et al., 2013). Following the introduction of rotavirus vaccines, HuNoVs have become the predominant gastrointestinal pathogen within pediatric populations in developed countries (Payne, et al., 2013). HuNoVs are highly contagious, with rapid person-to-person transmission directly through the fecal-oral route and indirectly from contact with contaminated fomites, or consumption of contaminated food or water. In addition to causing morbidity and mortality in young children, immunocompromised patients, and the elderly, norovirus disease causes significant economic burden as a result of health care costs and loss of productivity (Green, 2014; Belliot, et al., 2014). HuNoVs have resisted significant efforts to establish in vitro cultivation methods for over 40 years. Previous reports of possible cultivation systems have not been reproduced or support limited replication of a single strain (Straub, et al., 2007; Moore, et al., 2015; Jones, et al., 2015; Jones, et al., 2014). Insight into the pathophysiology of HuNoV infections has been elucidated primarily from studies using healthy adult volunteers. The lack of a reproducible culture system for HuNoVs has remained the major barrier to achieving a full mechanistic understanding of their replication, stability, antigenic complexity and evolution. An in vitro cultivation system is critical to define HuNoV-host interactions that underlie the high virus infectivity and explosive illness they cause, to determine how to prevent transmission, and to treat infections and illness.

Ex Vivo Human Intestinal Enteroid Cultures Support HuNoV Replication—

Figure 20:
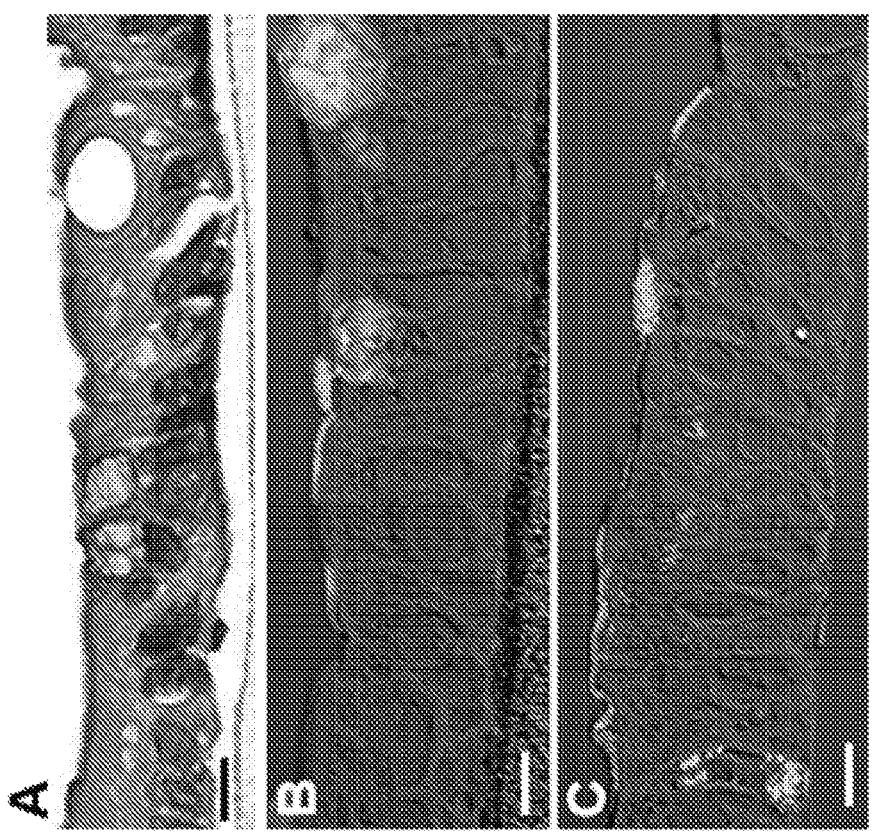
FIG. 20A-20C. Monolayer cultures of human intestinal enteroids contain enterocytes, goblet and enteroendocrine cells. Jejunal human intestinal enteroid monolayers grown on Matrigel-coated transwells were fixed with 10% formalin and embedded in paraffin. Thin sections were stained with (A) hematoxylin and eosin (H&E), and for expression of (B) the differentiation markers sucrase isomaltase (green) and Muc2 (cyan) that label enterocytes and goblet cells, respectively, or (C) chromogranin A (cyan) that labels enteroendocrine cells. (C) Expression of histoblood group antigens (HBGAs) was detected by UEA-1 lectin (green). In (B and C), adherens junctions are stained by E-cadherin (red) and nuclei by DAPI. Scale bar—10 μm.
Figure 21:
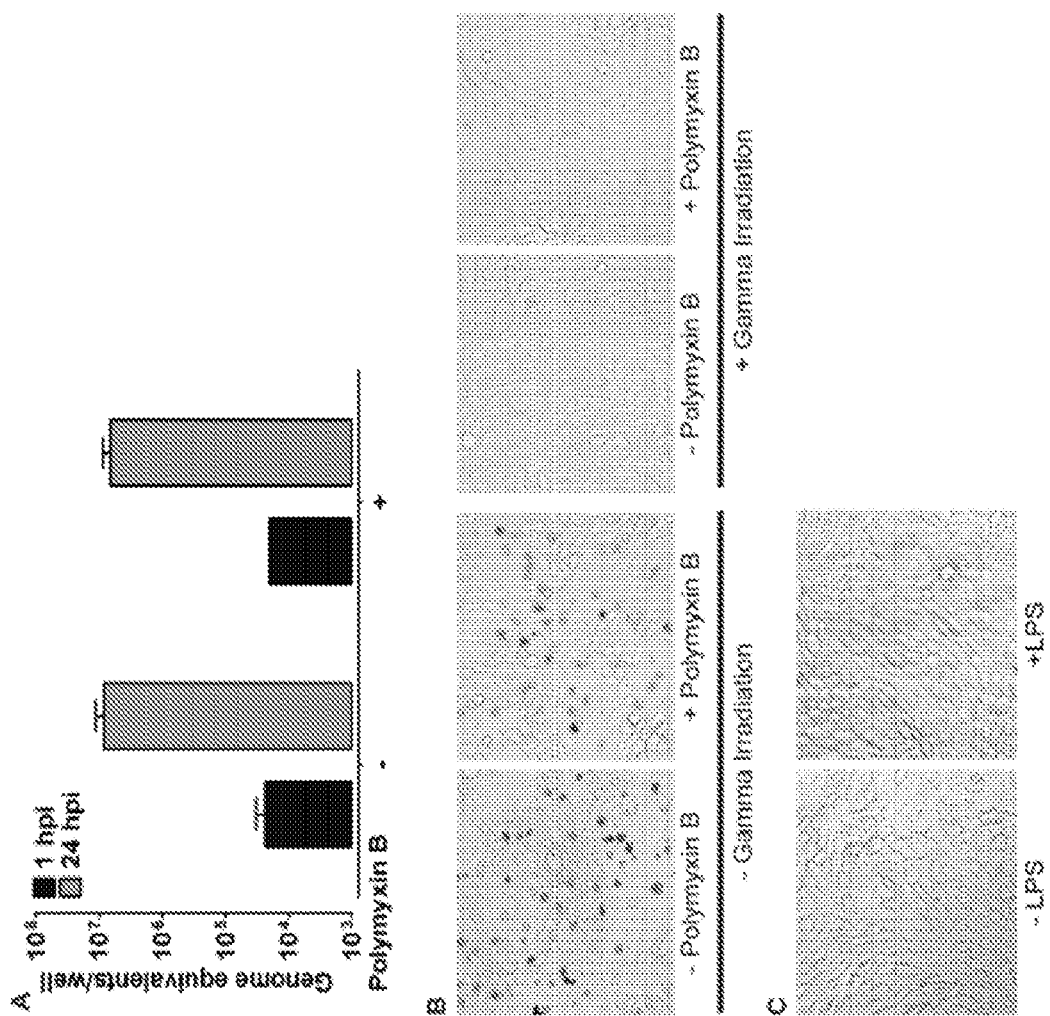
FIG. 21A-21C. Lipopolysaccharide does not enhance GII.4 replication and virus infection induces CPE. (A) GII.4/2012-1 stool filtrates were not treated (−) or treated (+) with 100 μg/ml polymyxin B for 24 hours. Then, $9\times10^5$ genome equivalents of the filtrates were inoculated onto each jejunal HIE monolayer for 1 hour. The monolayers were washed twice with CMGF(−) medium and cultured in differentiation medium. RNA was extracted from the cells and media and viral genome equivalents quantified by RT-qPCR. Data represent the mean of three wells for each treatment and time point. Error bars denote standard deviation. (B) Gamma irradiated or non-irradiated GII.4/2012-1 stool filtrates were either not treated (−) or treated (+) with polymyxin B for 24 hours. Jejunal HIE monolayers were inoculated with $9\times10^7$ genome equivalents for 1 hour as described above. (C) Jejunal HIE monolayers were either not treated (−) or treated (+) with LPS. (B and C) To assess cytotoxicity, trypan blue was added to the cultures at 3 dpi and imaged by bright field on an Olympus IX70 microscope with 20× magnification.
Figure 22:
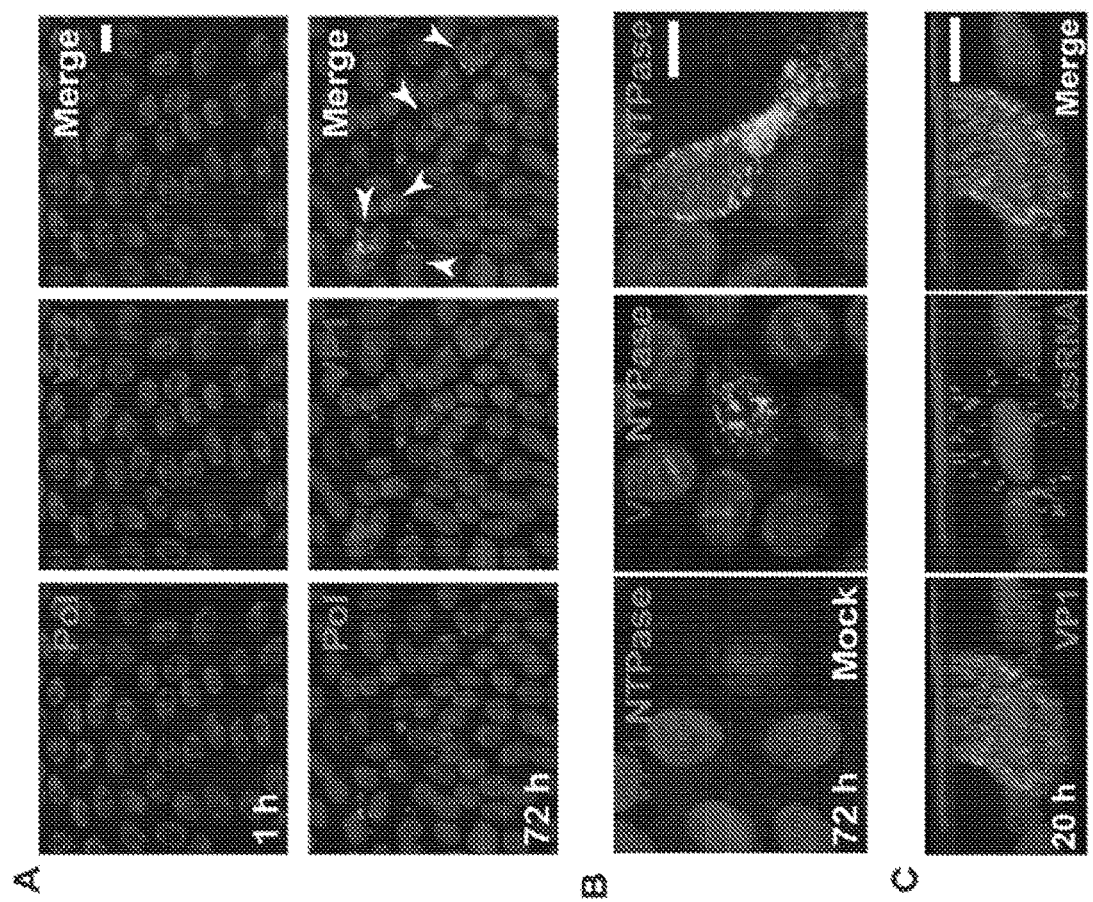
FIG. 22A-22C. Detection of GII.4 replication in human intestinal enteroids by immunofluorescence. Monolayers of jejunal human intestinal enteroids were mock-inoculated (B, left panel) or inoculated with $5.5\times10^5$ genome equivalents of GII.4/2006b-3 (all panels in A, and middle and right panels in B) or $9\times10^7$ genome equivalents of GII.4/2012-1 (C) for 1 hour at 37° C. The inoculated monolayers were washed twice with CMGF(−) media and cultured for 3 days (A and B) or 20 hours (C) in differentiation medium. (A-C) Expression of HuNoV proteins was detected in 4% PFA-fixed enteroid monolayers. VP1 was detected using guinea pig anti-GII.4/2012 VLP serum (red, A and B; green, C). Non-structural proteins were detected using (A) rabbit anti-GII.3 HuNoV polymerase (Pol, green) and (B) rabbit anti-GII.3 HuNoV NTPase (green), and double-stranded RNA (dsRNA) was detected (C) using J2 monoclonal anti-dsRNA (purple). DAPI detects nuclei (blue). (A) Arrowheads indicate cells expressing both VP1 and polymerase. (B) The middle and right panels represent two different cells expressing both VP1 and NTPase. Yellow represents colocalization of these two HuNoV proteins. (A-C) Scale bar—10 μm.

Attempts to culture HuNoVs in transformed intestinal epithelial cells and in primary human immune cells have been unsuccessful (Moore, et al., 2015; Duizer, et al., 2004; Lay, et al., 2010). We hypothesized that a novel culture system pioneered by the Clevers group in the Netherlands that generates human intestinal enteroids (HIEs) from stem cells isolated from intestinal crypts in human intestinal tissues (Sato, et al., 2011; Saxena, et al., 2015) and recapitulates the natural intestinal epithelium should support HuNoV growth. These multicellular, differentiated HIEs are nontransformed, physiologically active cultures that respond to agonists and contain multiple intestinal epithelial cell types (enterocytes, goblet, enteroendocrine, and Paneth cells) whether grown as three dimensional or monolayer cultures (FIG. 20) (Sato, et al., 2011; Saxena, et al., 2015; VanDussen, et al., 2015; Zachos, et al., 2016). To evaluate whether these novel cultures support replication of the previously noncultivatable HuNoVs, monolayers of HIEs were inoculated with GII.4 HuNoVs, which cause the majority of pandemic and outbreak infections worldwide (Ramani, et al., 2014). Jejunal monolayer cultures were readily infected by stool filtrates of multiple GII.4 variants (2006a, 2006b-1-3, 2009, and 2012-1, -2; Table 3). At 96 hours post-infection (hpi), 1.5-2.5 $\log_{10}$ increases in genome equivalents of viral progeny were identified by RT-qPCR in comparison to the amount of genomic RNA detected at 1 hpi after removal of the virus inoculum and two washes of the monolayers to remove unattached virus (FIG. 15A, fold changes indicated above the bars for each variant). All inocula used to infect enteroid cultures were fecal filtrates, suggesting that bacteria were not required as co-factors for infection in contrast to previous reports of HuNoV cultivation in BJAB and Raji B cell lines (Jones, et al., 2015; Jones, et al., 2014). Lipopolysaccharide (LPS) in stool filtrates did not promote replication, as there was no reduction in HuNoV replication in samples treated with polymyxin B that reduced LPS levels from 4.84 to 0.63 endotoxin units (Lay, et al., 2010) (FIG. 21A).

TABLE 3

Cultivatable HuNoV strains.

| Reference Strain | Strain | Genotype_variant | Strain Designation | P-type[1] | Titer (genome equivalents/μl)[2] |
| --- | --- | --- | --- | --- | --- |
| GI/Hu/US/1968/GI.1/Norwalk | BCM723-02 | GI.1 | GI.1 | GI.P1 | $5.7 \times 10^6$ |
| GII/Hu/US/2004/GII.3/TCH04-577 | TCH04-577 | GII.3 | GII.3 | GII.P21 | $8.5 \times 10^6$ |
| GII/Hu/US/2007/GII.4/TCH07-194 | TCH07-194 | GII.4_Yerseke_2006a | GII.4/2006a | GII.P4 | $7.0 \times 10^7$ |
| GII/Hu/US/2007/GII.4/TCH07-882 | TCH07-882 | GII.4_Den Haag_2006b | GII.4/2006b-1 | GII.P4 | $1.5 \times 10^7$ |
| GII/Hu/US/2008/GII.4/TCH08-227 | TCH08-227 | GII.4_Den Haag_2006b | GII.4/2006b-2 | GII.P4 | $5.3 \times 10^6$ |
| GII/Hu/US/2009/GII.4/MDA09-01 | MDA09-01 | GII.4_Den Haag_2006b | GII.4/2006b-3 | GII.P4 | $1.1 \times 10^7$ |
| GII/Hu/US/2011/GII.4/TCH11-64 | TCH11-64 | GII.4_New Orleans_2009 | GII.4/2009 | GII.P4 | $3.0 \times 10^7$ |
| GII/Hu/US/2012/GII.4/TCH12-580 | TCH12-580 | GII.4_Sydney_2012 | GII.4/2012-1 | GII.Pe | $1.8 \times 10^8$ |
| GII/Hu/US/2014/GII.4/TCH14-10 | TCH14-10 | GII.4_Sydney_2012 | GII.4/2012-2 | GII.Pe | $3.0 \times 10^6$ |
| GII/Hu/US/2014/GII.17/TCH14-38 | TCH14-385 | GII.17 | GII.17 | GII.Pn | $1.4 \times 10^7$ |

[1]Polymerase type.
[2]Titer of the processed 10% stool suspension filtered through a 0.22 μm filter (25% for GI.1 and 10% for GII.17 filtered through a 0.45 μm filter).

Figure 15:
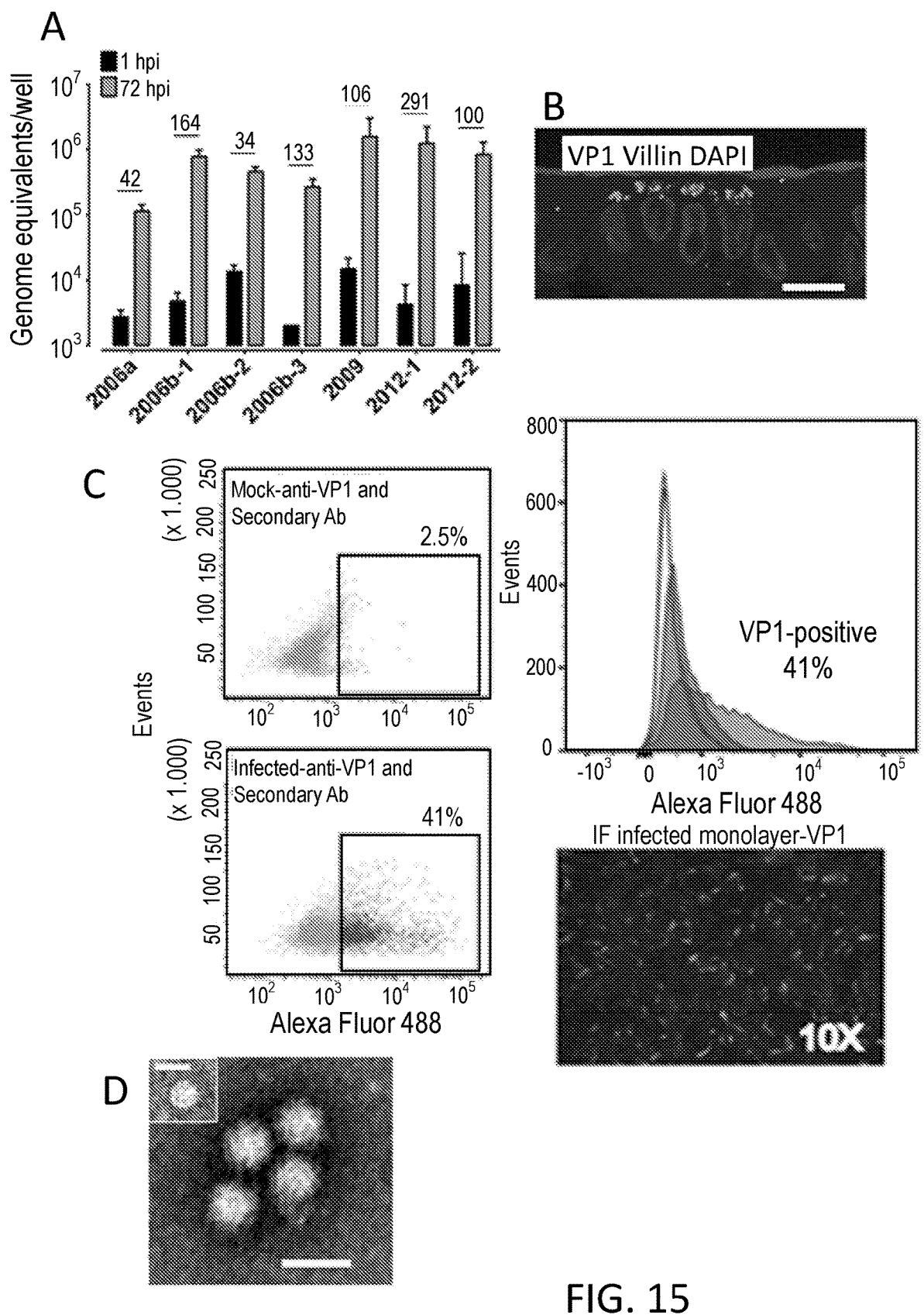
FIG. 15A-15G. Replication of GII.4 variants in human intestinal enteroids. Jejunal HIE monolayers were inoculated with (A) $9 \times 10^5$ genome equivalents of the indicated HuNoV GII.4 stool filtrates. RNA was extracted from cells and medium, and viral genome equivalents quantified by RT-qPCR. RNA at 1 hpi was collected after removal of virus inoculum and washing of cells twice to remove any unattached viruses. Each data bar represents the mean of three wells of inoculated HIEs. Error bars denote standard deviation. Each experiment was performed two or more times, with three technical replicates in each experiment. Panels (B-E) and (F) represent monolayers inoculated with $9 \times 10^7$ and $9 \times 10^5$ genome equivalents of GII.4/2012-1, respectively. (B) Expression of VP1 was detected in enterocytes (villin, red) in formalin-fixed, paraffin-embedded enteroid monolayer sections using antibody against GII.4/2012 VLPs (green). DAPI detects nuclei (blue). Scale bar=25 µm. (C) Flow cytometry quantitation and immunofluorescent detection of infected cells. Scale bar=100 µm. (D) Electron micrograph of HuNoV particles from the supernatant of infected HIEs. Scale bar=50 nm. Inset: small particle. Scale bar=25 nm. (E) Western blot detecting polyprotein processing and VP1 expression. Asterisk marks a non-specific band. (F) Kinetics of HuNoV yield at the indicated time points. (G) Passaging of GII.4/2009 HuNoV in jejunal HIEs. (F, G) Viral genome equivalents quantified by RT-qPCR as indicated for panel A.
Figure 23:
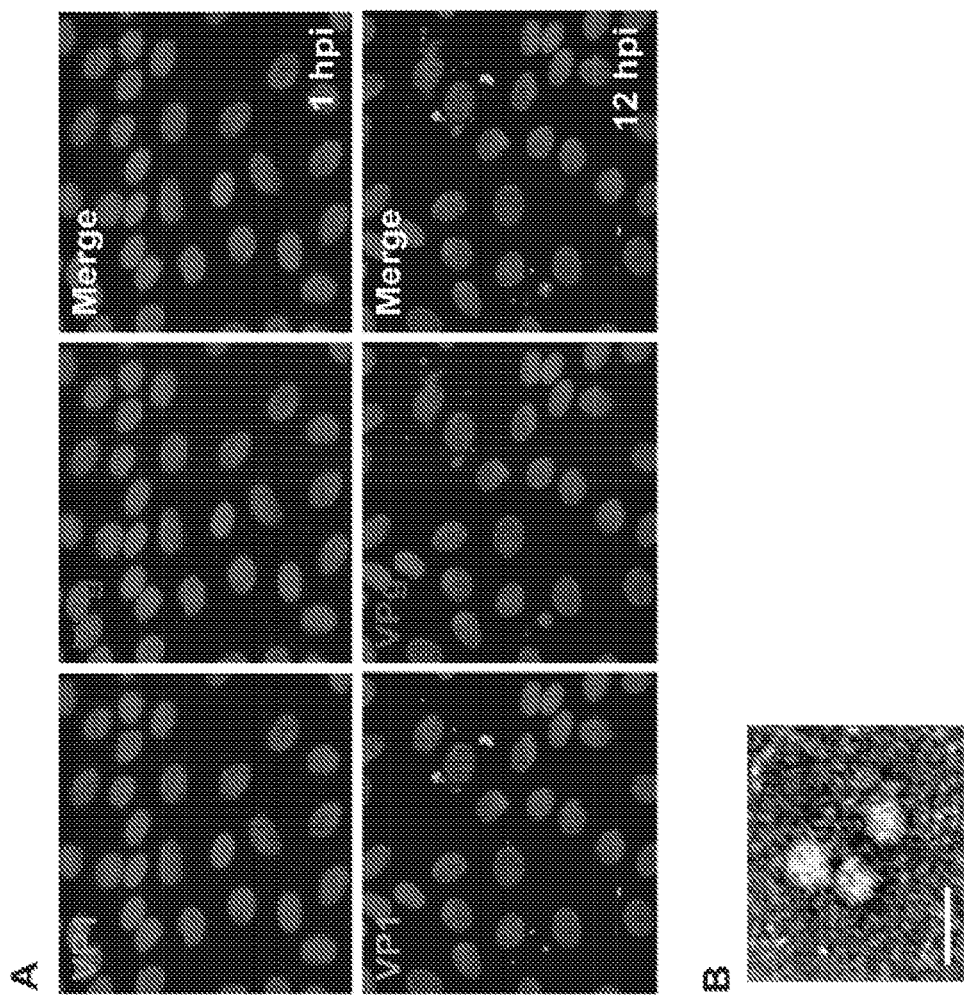
FIG. 23A-23B. Detection of HuNoV antigen and virus particles in passage 4 infections. Jejunal HIEs were infected with GII.4/2012-1 passage 3 virus. (A) Cells were fixed at 1 and 12 hpi and stained with antibody against GII.4/2012 VLPs (green) and VPg (red). (B) Media collected at 72 hpi, was clarified by centrifugation for 10 min at 8,000×g, applied to grids, stained and imaged by EM as described in FIG. 1. Scale bar=50 nm.

We next evaluated the growth characteristics of HuNoV infection by assessing cytopathic effect (CPE), antigen detection, and the kinetics of infection. Cytopathic changes such as cell rounding, destruction of the monolayer and an increase in number of dead cells as assessed by trypan blue staining were observed in GII.4-inoculated cultures. CPE was observed for GII.4 variants tested (2012-1, -2 and 2006b-3, see Table 3 for strain details; GII.4/2012-1 results shown in FIG. 21B, left panel). CPE was not reduced by inoculation with polymyxin B-treated samples (FIG. 21B), and CPE was not observed in cultures inoculated with gamma-irradiated stool filtrate (FIG. 21B, right panels), which abrogated viral replication. Viral replication was demonstrated by detecting the major viral capsid protein (VP1), with nonstructural proteins, [RNA-dependent RNA polymerase (Pol) and NTPase], or double-stranded RNA (dsRNA, an intermediate in HuNoV RNA replication) in infected cells by confocal microscopy (FIG. 15B and FIG. 22A-C). Immunofluorescent analysis for VP1 revealed 35-45% of cells in the HIE monolayer were infected, which was confirmed by flow cytometry where 41% of cells were VP1-positive (FIG. 15C). HIE cultures contain multiple cell types (stem cells, Paneth cells, goblet, enteroendocrine and enterocyte cells) and only the enterocytes were infected. Detection of villin, an enterocyte marker, in VP1-positive cells showed that HuNoVs infected and replicated in enterocytes (FIG. 15B). Productive infection was confirmed by transmission electron microscopic visualization of virus particles with typical morphology (Kapikian, et al., 1972) in the supernatant of infected HIEs (FIG. 15D). Two particle sizes were detected (FIG. 15D), with particles of the expected size (31.6+/−3.3 nm) and some smaller particles (FIG. 15D inset, 18.5+/−3.7 nm). Both particle sizes have been observed previously in stools of children infected with HuNoVs and in preparations of recombinant virus-like particles (VLPs) (White, et al., 1997). By Western blot analysis, nonstructural polyprotein synthesis and processing (as evidenced by the detection of several VPg-containing polyprotein processing intermediates) and capsid protein (VP1) production were first detected at 12 hpi in infected cells but not at 1 or 6 hpi or in mock-infected cells (FIG. 15E). Consistent with the production of virus particles (FIG. 15D), VP1 was detected in the culture supernatant by 24 hpi (FIG. 15E). Replication was confirmed by the growth kinetics of GII.4/2012-1 in jejunal HIE monolayer cultures, which showed a time-dependent increase in genome equivalents between 1 and 24 hpi after which a plateau was reached (FIG. 15F). Because polyprotein processing, RNA replication, and synthesis of subgenomic RNA are required for VP1 and particle production (Green, et al., 2013), these findings demonstrate that an entire HuNoV replication cycle occurs in infected HIEs by 24 hpi. GII.4/2009 and GII.4/2012-1 HuNoV could also be passaged in jejunal HIEs with optimized conditions (FIG. 15G, GII.4/2009 shown, see below for conditions). Cells expressing VP1 and VPg were observed during infection with passaged virus and particles of both sizes (FIG. 23B) were seen. Together, these results indicate that GII.4 HuNoV-infection of HIEs results in a productive and complete virus replication cycle and this system can be used to define cellular processes HuNoVs co-opt to replicate and induce pathogenesis.

Replication of Some HuNoV Strains Requires the Presence of Bile—

Figure 16:
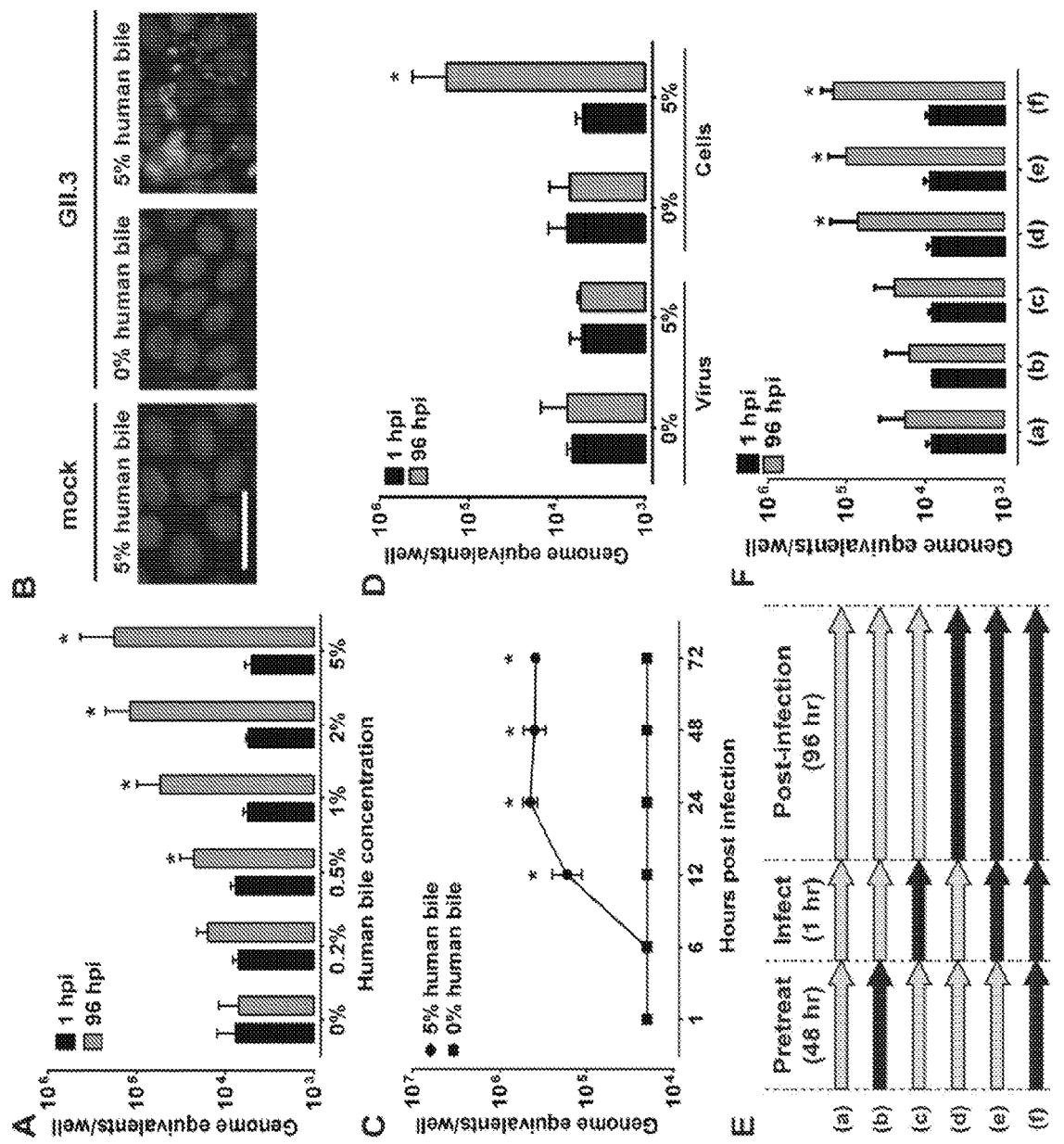
FIG. 16A-16F. Bile is required for GII.3 HuNoV replication and affects the cells. Jejunal HIE monolayers were pretreated (A-C) with the indicated concentrations of human bile for 2 days and then inoculated with GII.3 stool filtrate [(A, C) $4.3 \times 10^5$ or (B) $4.3 \times 10^7$ genome equivalents] and incubated with the same bile concentrations as used for pretreatment (see supplementary methods). (B) VP1 was detected in methanol-fixed monolayers at 24 hpi using guinea pig anti-GII.3 VLP antiserum (green) and DAPI to detect nuclei (blue). Scale bar=25 µm. (D) To determine if the effect of bile was on the virus or the cells, the virus was either not treated or treated with 5% human bile for 1 hour at 37° C., and then diluted to decrease the bile concentration to 0.025% prior to infection of HIE monolayers not pretreated with bile. Alternatively, cells were either not treated or treated with 5% human bile for 2 days prior to and during infection. Inoculations were performed with $4.3 \times 10^5$ genome equivalents. (E) Schematic showing with black arrows when bile was added to HIEs for the experiment shown in (F). For A, C, D and F, genome equivalents were determined as indicated in FIG. 15. Error bars denote standard deviation. *, P<0.05 comparing genome equivalents to 1 hpi.
Figure 24:
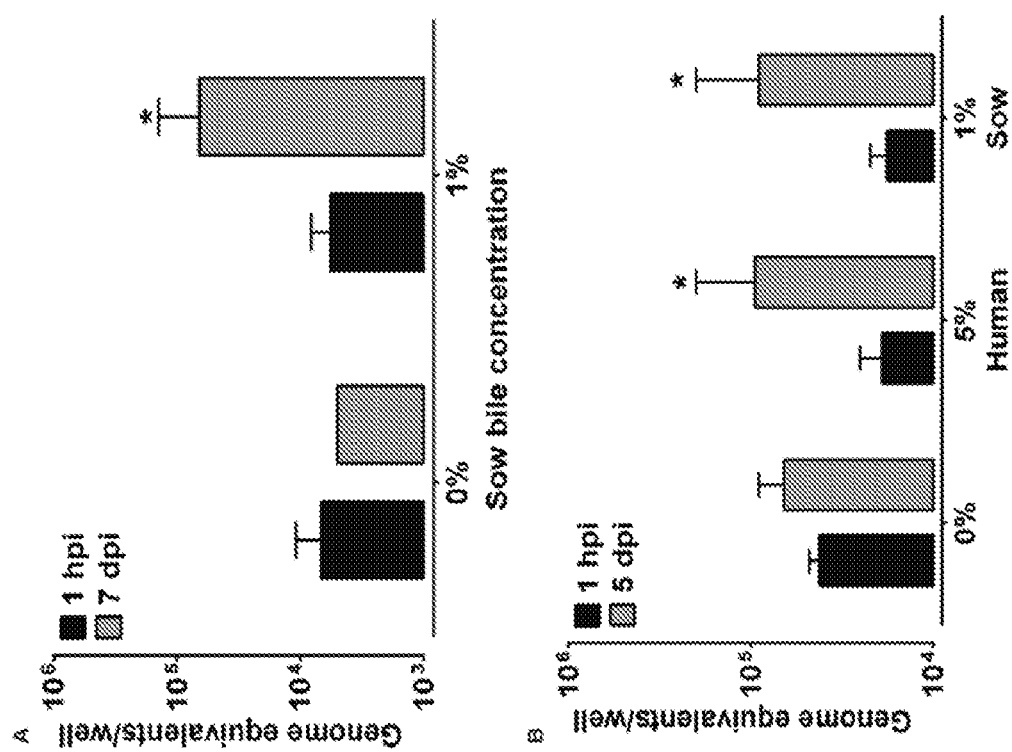
FIG. 24A-24B. GI.1 and GII.17 HuNoVs require bile for replication in human intestinal enteroids. Jejunal human intestinal enteroid monolayers were pretreated with the indicated concentrations of bile for 2 days, inoculated with (A) GI. 1 or (B) GII.17 stool filtrates ($2.9\times10^6$ or $9.7\times10^6$ genome equivalents, respectively) in the presence of the indicated concentrations of bile for 1 hour at 37° C. The monolayers were washed three times with CMGF(−) medium and cultured for the indicated days in differentiation medium in the absence (0%) or presence of the indicated concentrations of bile. At 1 hour and the indicated time post-inoculation, the cells and medium were harvested, RNA extracted and viral genome equivalents quantified by RT-qPCR. Data represent the mean of three wells for each treatment and time point. Error bars denote standard deviation. *, $P<0.05$ comparing genome equivalents from 1 hpi to the indicated time points.
Figure 25:
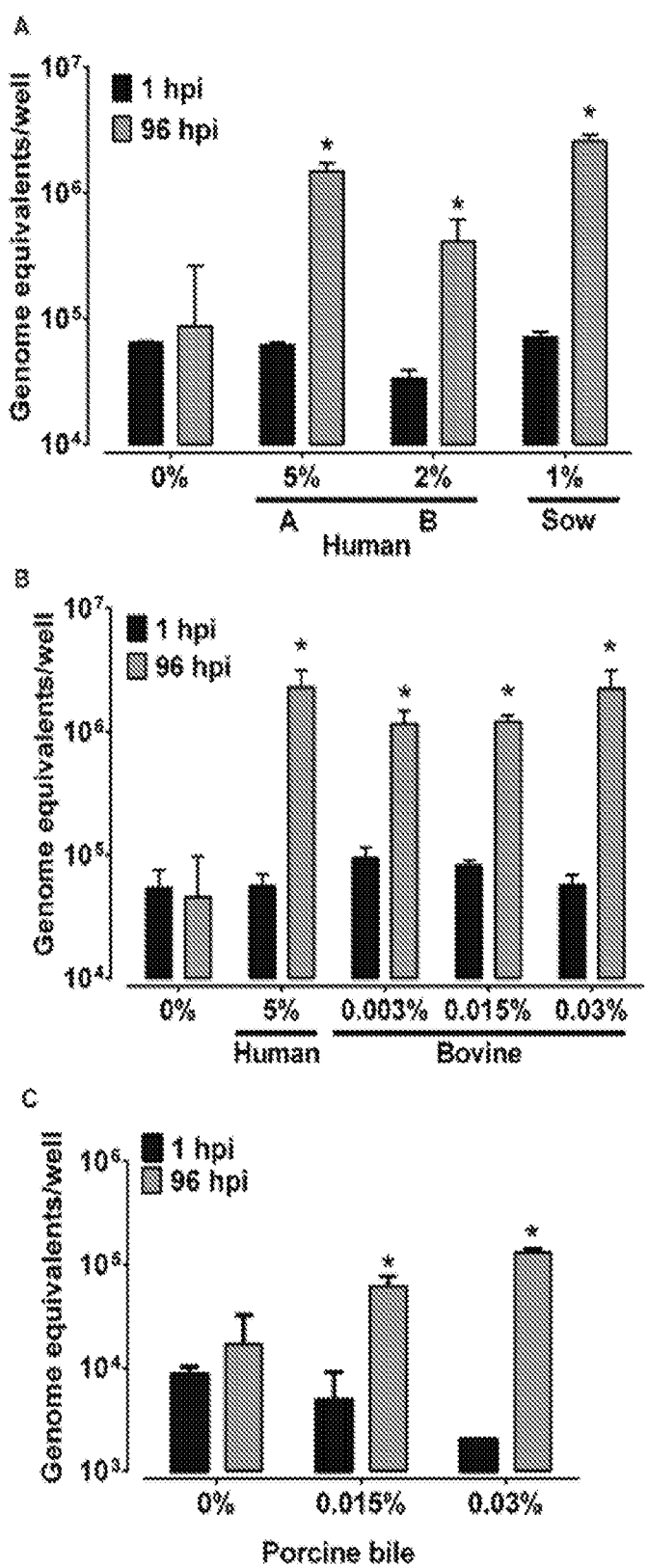
FIG. 25A-25C. Bile from different sources promotes GII.3 HuNoV replication. (A-C) Jejunal human intestinal enteroid monolayers were pretreated with the indicated concentrations of bile for 2 days, inoculated with $4.3\times10^5$ genome equivalents of GII.3 stool filtrates in the presence or absence of bile for 1 hour at 37° C. The monolayers were washed twice with CMGF(−) medium and cultured for 96 hours in differentiation medium in the absence (0%) or presence of the indicated concentrations of bile. At 1 and 96 hpi, the cells and medium were harvested, RNA extracted and viral genome equivalents quantified by RT-qPCR. Data represent the mean of three wells for each treatment and time point. Error bars denote standard deviation. *, $P<0.05$ comparing genome equivalents from 1 to 96 hpi.
Figure 26:
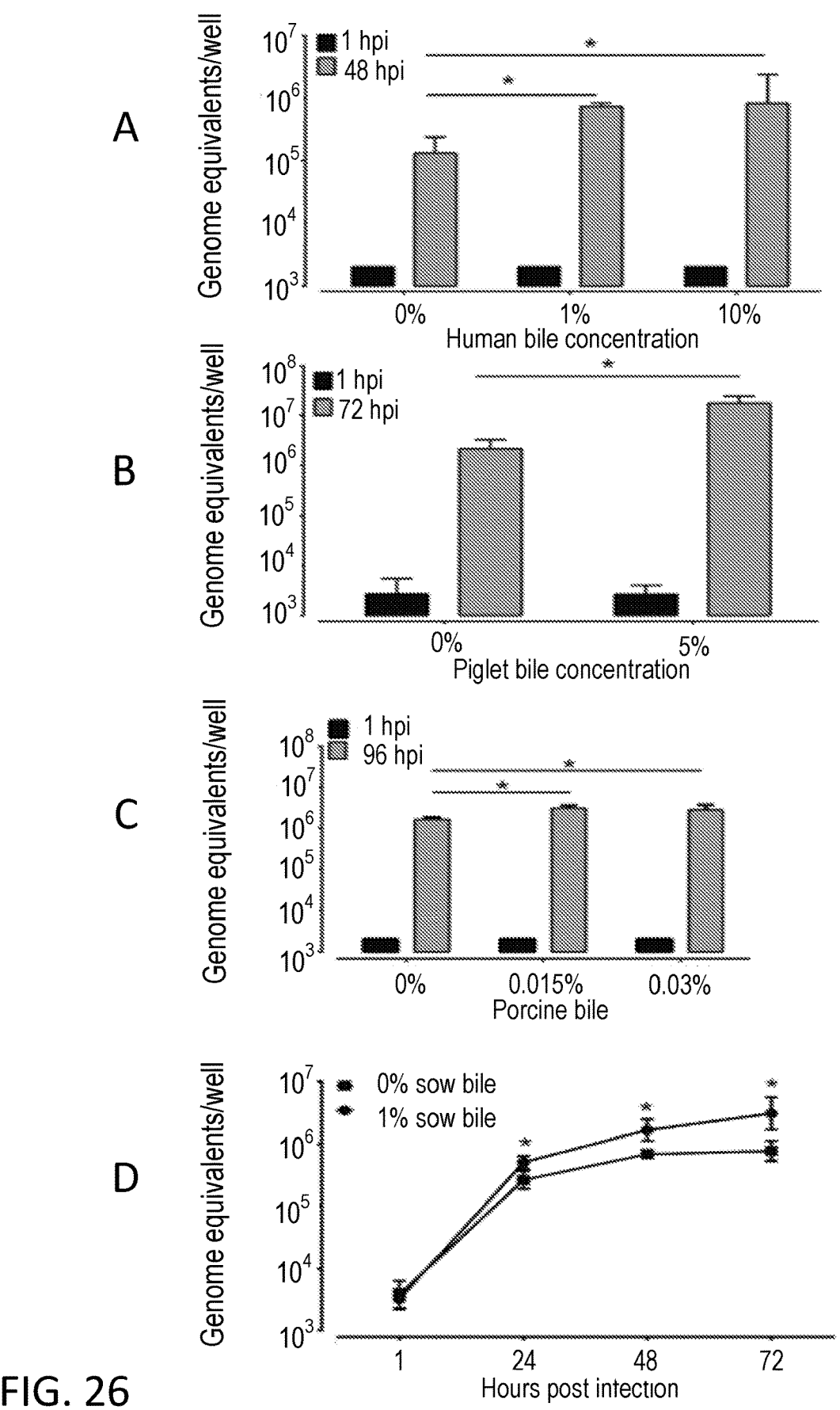
FIG. 26A-26D. Bile is not required but enhances GII.4 HuNoV replication. (A-D) Jejunal human intestinal enteroid monolayers were treated with the indicated concentrations of bile for 2 days during differentiation. The monolayers were inoculated with $5.5\times10^5$ genome equivalents of (A) GII.4/2006b-3 or, (B) GII.4/2009, or (C and D) GII.4/2012-1 in the absence or presence of the indicated bile for 1 hour at 37° C. The monolayers were washed twice with CMGF(−) medium and cultured in differentiation medium in the absence (0%) or presence of the indicated concentrations of bile. RNA was extracted from the cells and media and viral genome equivalents quantified by RT-qPCR. Data represent the mean of three wells for each treatment and time point. Error bars denote standard deviation. *, $P<0.05$ comparing genome equivalents between no bile and bile treatment for A-C, and between 0 and 1% sow bile for each time point for D.

Noroviruses are genetically diverse. Most HuNoVs are classified into two genogroups (GI and GII), which are further subdivided into 9 GI genotypes and 20 GII genotypes. We next tested whether monolayer cultures of jejunal HIEs could support replication of other HuNoV strains (GI.1, GII.3, GII.17). Initially, no replication of these viruses was observed. Consequently, several components of the intestinal milieu were assessed for their ability to promote replication of these HuNoVs in HIE monolayers. Addition of proteases (trypsin, pancreatin) required for the replication of another gastrointestinal virus, human rotavirus, failed to enhance HuNoV replication. In contrast, viral replication, as demonstrated by RT-qPCR and immunofluorescence analyses, was observed in HIEs pretreated with nontoxic levels of human bile and inoculated with stool filtrates of GII.3, GII.17 and GI.1 HuNoVs (FIGS. 16A and B, and FIG. 24). Replication occurred in a bile dose-dependent manner, with concentrations of human bile greater than or equal to 0.5% being required for GII.3 replication (FIG. 16A). Bile from different sources such as human, sow and commercially available bovine and porcine, all promoted GII.3 replication without CPE (FIG. 25). Assessment of the kinetics of GII.3 infection demonstrated that, similar to GII.4 strains, virus yields increased between 1 and 24 hpi (FIG. 16C). The addition of bile to GII.4 HuNoV-inoculated cultures was not required, but it enhanced virus replication (FIG. 26). Enhancement was observed when human (FIG. 26A), piglet (FIG. 26B), porcine (FIG. 26C) and sow (FIG. 26D) bile were evaluated. These results indicate there are strain-specific differences in the requirement for factors in the intestinal milieu such as bile to support or enhance HuNoV replication. Of note, even with the addition of bile, the increases in yields for GII.3 as well as for GII.17 and GI. 1 virus strains were lower than that observed for the GII.4 variants. In 12 independent experiments performed in triplicate on jejunal HIEs, the mean fold increase of GII.3 genome equivalents ranged from 10-173 fold with an average of a 48 fold increase as compared to 34-6730 fold increases (average 670 fold) for GII.4 HuNoVs. Evaluation of additional intestinal components or further optimization of conditions may be required to achieve higher levels of replication for GII.3 and other HuNoVs. To date, we have successfully obtained replication of two HuNoV genogroups comprising four genotypes of virus (including four GII.4 variants, and GII.3, GII.17 and GI.1 strains) in human jejunal enteroid monolayers (Table 3).

Figure 27:
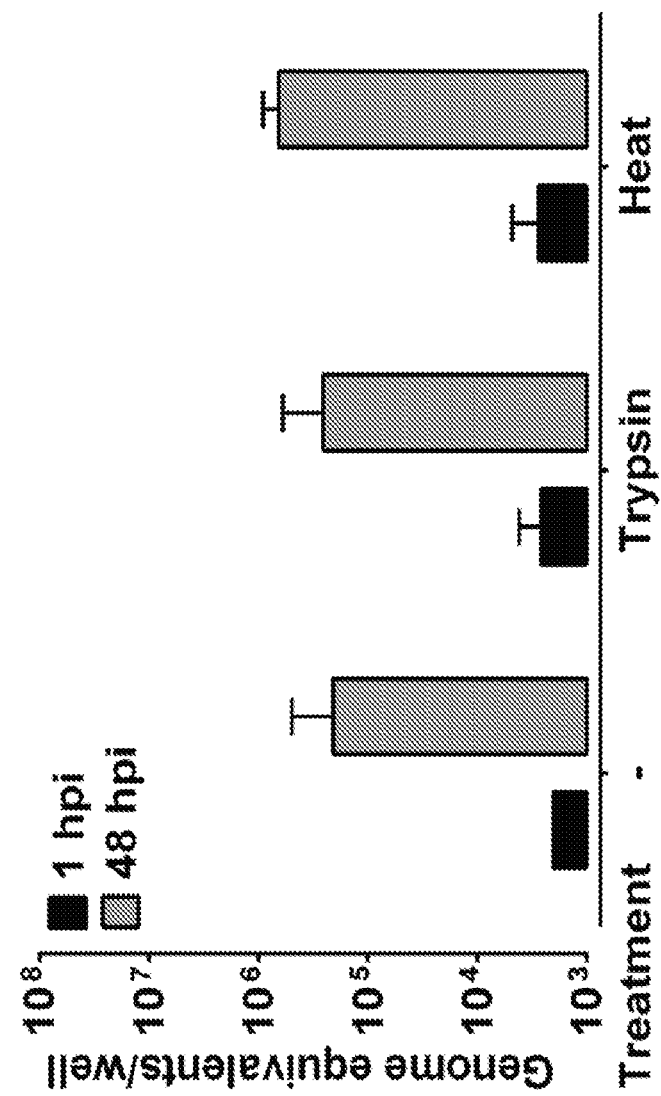
FIG. 27. The factor in bile required for GII.3 infection is not proteinaceous. Human bile was not treated (−) or treated with trypsin for 24 hours at 37° C., followed by the addition of soybean trypsin inhibitor to inactivate the trypsin or bile was heated at 100° C. for 5 minutes. These bile preparations (5% final concentration) were used to pretreat HIE monolayers for 2 days during differentiation followed by infection with $4.3\times10^5$ genome equivalents of GII.3 for 1 hour at 37° C. as previously described. RNA was extracted from the cells and media, and viral genome equivalents quantified by RT-qPCR. Data represent the mean of three wells for each treatment and time point. Error bars denote standard deviation.
Figure 28:
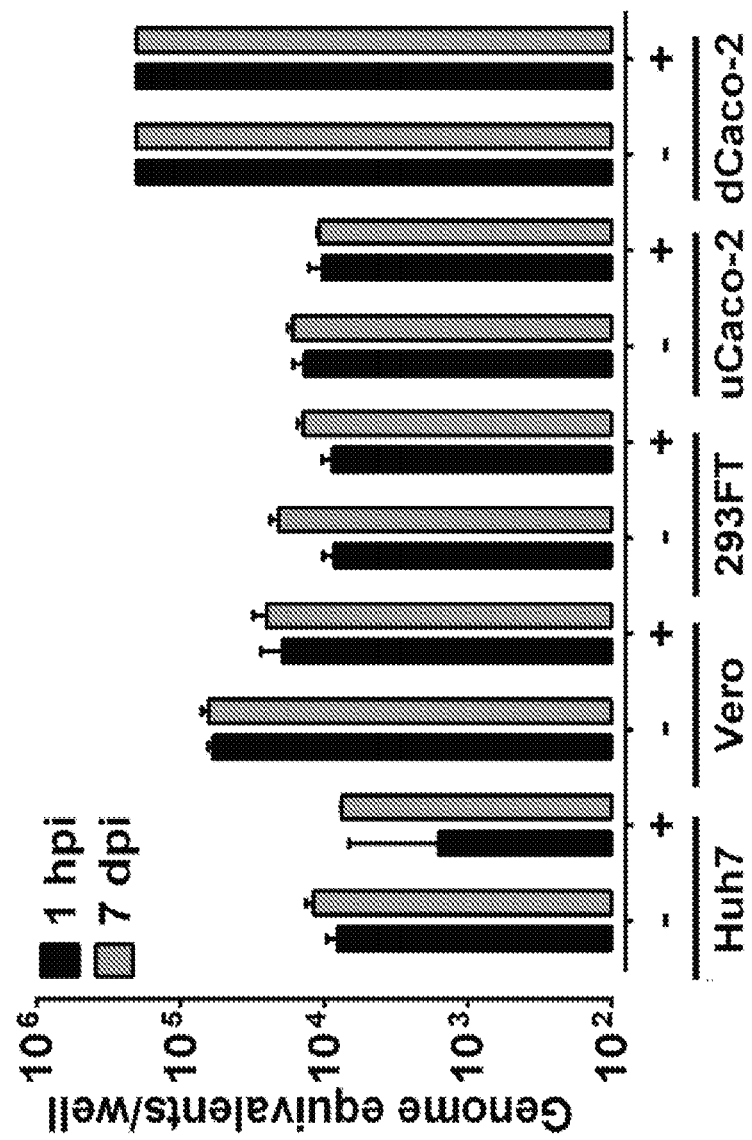
FIG. 28. GII.3 does not replicate in transformed cell lines treated with bile. Huh7, Vero, 293FT and undifferentiated Caco-2 BBe (uCaco-2) cells were pretreated with 0 (−) or 5% (+) human bile for 2 days. The pretreated cells were inoculated with GII.3 ($4.3\times10^6$ genome equivalents of GII.3 stool filtrate) for 1 hour at 37° C. and cultured for 7 days. Differentiated Caco-2 BBe (dCaco-2) cells cultured in transwells for 21 days were pretreated as indicated with bile and inoculated with GII.3 stool filtrate. The human bile was added or not into medium during and post-inoculation. At 1 hour and 7 days post-inoculation, the cells and medium were harvested, RNA extracted and viral genome equivalents quantified by RT-qPCR. Data represent the mean of three wells for each treatment and time point. Error bars denote standard deviation.

We next evaluated whether the requirement of bile for GII.3 HuNoV infection and replication was due to a bile effect on the HIE cells or the virus. Stool filtrate was pretreated with 5% bile or PBS for 1 hour and then diluted in PBS (final concentration of 0.025% in the bile-treated sample) prior to inoculating HIE cultures not treated with bile. HIEs also were either not treated or treated with 5% bile for 48 hours prior to and during infection. The pre-treatment of cells with bile was carried out for a longer duration as compared to pre-treatment of the virus with bile because bile has multiple known effects on cellular functions, including acting as a detergent, increasing digestion and absorption of fat, and regulating metabolic and inflammatory processes by activating various signaling pathways (Hoffman, et al., 1994). An increase in genome equivalents was observed only when HIEs, not the virus, was treated with bile (FIG. 16D), indicating that the bile effect is on the cells and not the virus. Further assessment of bile treatment revealed that addition of bile to cultures during or after virus adsorption but not prior to adsorption is required for GII.3 replication (FIGS. 16E and F). Testing of heat- or trypsin-treated bile for GII.3 infections in HIEs found no effect on replication (FIG. 27), indicating that the active factor is not proteinaceous. The successful cultivation of GII.3 HuNoV required both novel HIE cultures and supplementary bile as the addition of bile to transformed epithelial cell lines including Huh7, Vero, HEK293FT and undifferentiated or differentiated Caco-2 BBe cells did not promote HuNoV replication (FIG. 28). These results indicate HIEs and bile together mimic the human replication niche of HuNoVs.

Figure 29:
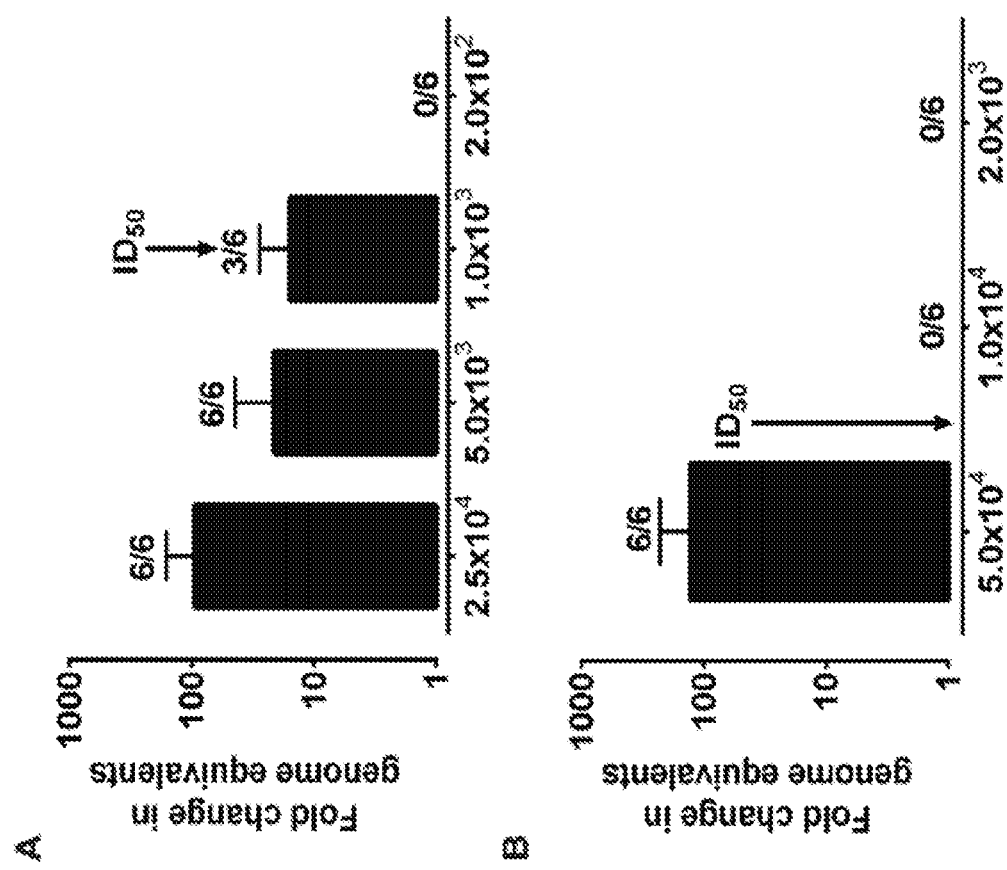
FIG. 29. Determination of $ID_{50}$. Jejunal human intestinal enteroid monolayers were treated with bile (see below) for 2 days during differentiation. The monolayers were inoculated with serial dilutions of (A) GII.4/2012-1 or (B) GII.3 HuNoV genome equivalents in the presence of 1% sow bile for GII.4 or 5% human bile for GII.3 for 1 hour at 37° C. The monolayers were washed twice with CMGF(−) medium and cultured for 7 days in differentiation medium in the presence of bile. At 1 hpi and 7 dpi, the cells and medium were harvested, RNA extracted and viral genome equivalents quantified by RT-qPCR. Data represent the mean of three wells for each treatment and time point from one representative experiment. Error bars denote standard deviation. Infectious dose 50 ($ID_{50}$) was calculated by the Reed-Muench method using the geometric mean of two experiments.

The sensitivity of the HIE culture system to support HuNoV replication was evaluated by determining the lower limit of virus required for successful infection. For this, the infectious dose 50% ($ID_{50}$) for GII.4 and GII.3 HuNoVs was calculated by the Reed-Muench method (Reed, et al., 1938). The $ID_{50}$ for GII.4/2012-1 and GII.3 HuNoVs were ~1,200 and ~$2.0 \times 10^4$ genome equivalents/well, respectively, assessed at 7 days post-infection (dpi, geometric mean of two experiments, representative experiments shown in FIGS. 29A and B). These results indicate that this replication system is amenable to determining the infectivity of low levels of virus, as has been observed in emesis, contaminated food and in fecal samples after recovery from illness (Moore, et al., 2015; Atmar, et al., 2008; Le Guyader, et al., 1996). This replication system also will allow evaluation of whether virus, currently detected in a variety of samples using molecular methods, is infectious and poses a potential risk to human health.

HuNoVs Replicate in Enterocytes in Cultures from Different Segments of the Small Intestine—

Figure 17:
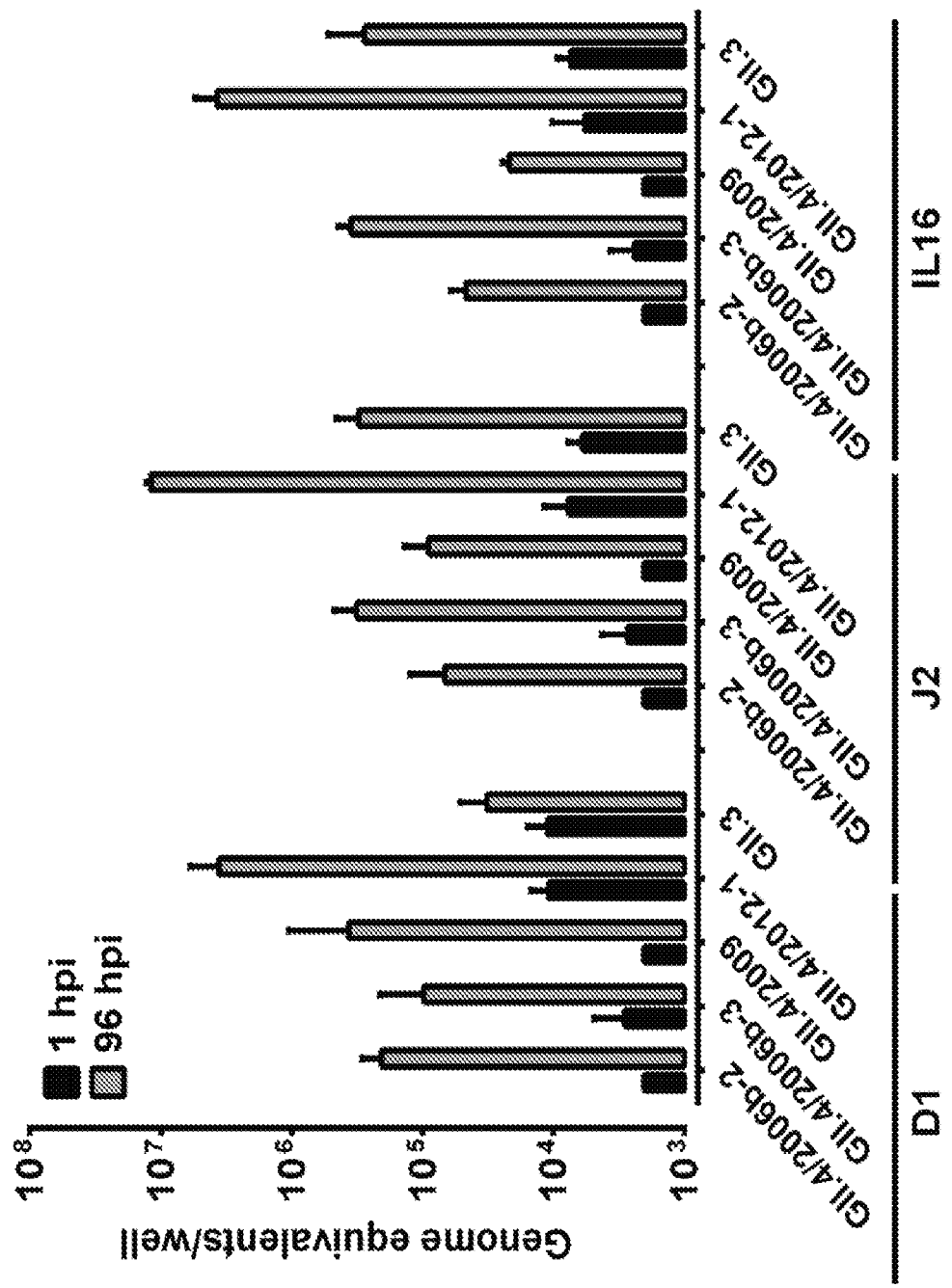
FIG. 17. GII.4 variants and GII.3 HuNoVs replicate in HIEs generated from different intestinal segments. Duodenal (D1), jejunal (J2), and ileal (IL16) HIEs were treated with 1% sow bile for the GII.4 variants or 5% human bile for GII.3 for 48 hours, and then inoculated with the indicated HuNoVs (GII.4/2006b-2, GII.4/2009, GII.4/2012-1: $9 \times 10^5$; GII.4/2006b-3: $5.5 \times 10^5$; GII.3: $4.3 \times 10^5$ genome equivalents) and cultured in the presence of bile. Genome equivalents were determined as indicated in FIG. 15. Error bars denote standard deviation.

The site of replication of HuNoVs in immunocompetent individuals is unknown, although histologic alterations have been observed in biopsies from volunteers infected with Norwalk virus (Agus, et al., 1973) and antigen has been detected in duodenal, jejunal and to a lesser extent in ileal enterocytes from gnotobiotic pigs infected with a GII.4 HuNoV (Cheetham, e al., 2006). We therefore evaluated whether HuNoVs infect cells derived from different regions of the small intestine by inoculating HIE cultures made from biopsies obtained from different intestinal segments that retain segment-specific properties (Middendorp, et al., 2014). GII.4 and GII.3 HuNoVs replicated in enteroids derived from duodenal, jejunal and ileal intestinal segments (FIG. 17). Replication varied by strain and intestinal segment, with GII.4 variants showing 11-1535 fold increases between 1 and 96 hpi in the three segments and GII.3 virus showing 3-51 fold increases. We investigated whether HuNoV replicated in cell types other than enterocytes. HuNoV antigen was not detected in goblet (n=200 cells) or enteroendocrine cells (n=50 cells) assessed in duodenal, jejunal and ileal HIEs. Together, the growth of HuNoVs in HIEs from all segments of the small intestine detected by RNA replication and confocal staining indicates enterocytes (FIG. 15B) are the primary target for infection and replication.

Secretor Status of HIEs Affects Strain-Specific HuNoV Replication—

Figure 18:
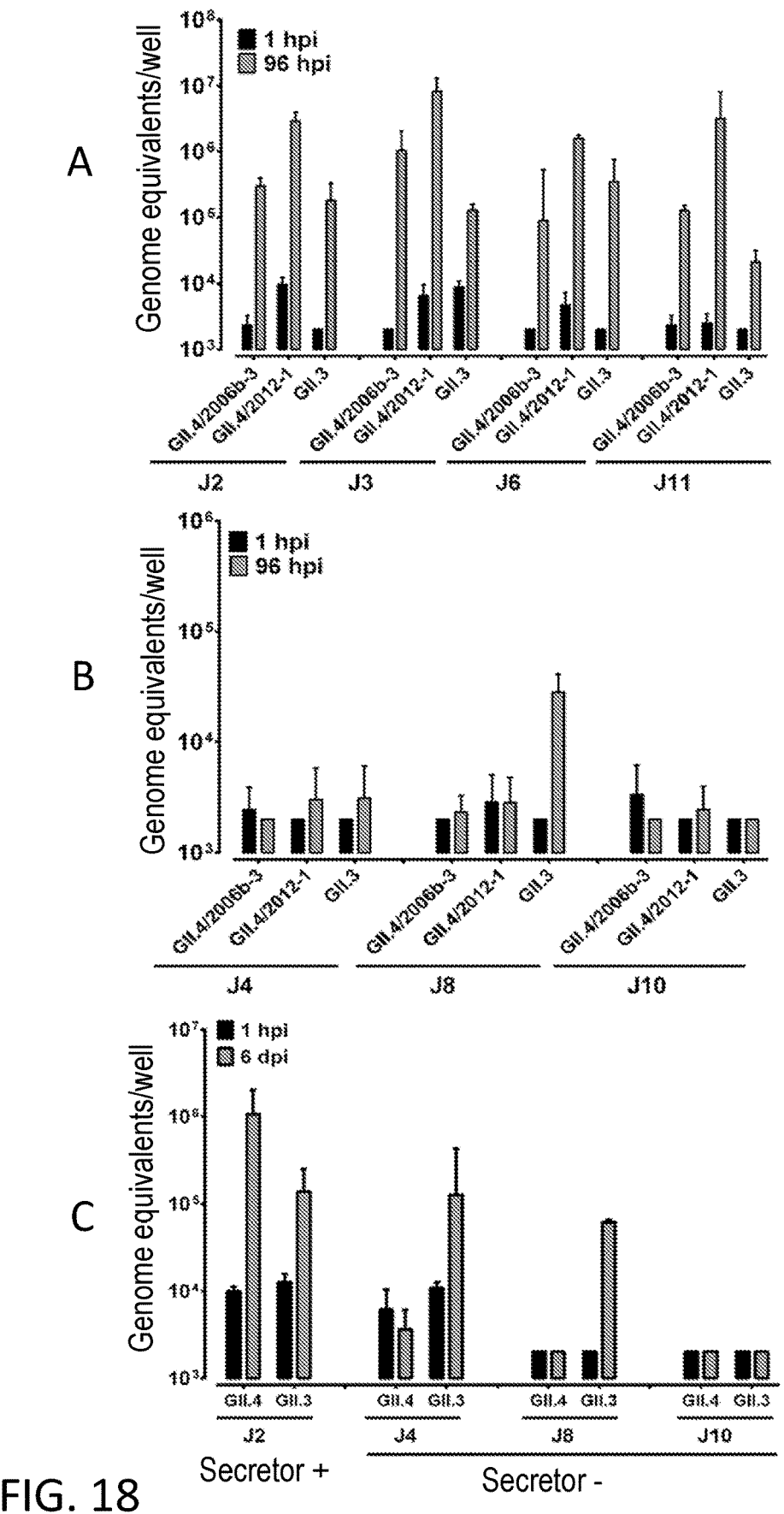
FIG. 18A-18C. Replication of GII.4 strains but not GII.3 depends on HIE secretor status. (A) Secretor positive jejunal (J2, J3, J6 and J11) or (B) secretor negative jejunal (J4, J8 and J10) HIEs were inoculated with the indicated GII.4 or GII.3 HuNoVs (with the same amounts of genome equivalents as indicated in FIG. 3) in the presence of bile (1% sow bile for GII.4 variants or 5% human bile for GII.3) for 96 hours. At 96 hpi, GII.4 strains replicate in secretor positive HIEs but not secretor negative lines, while GII.3 replicates in all secretor positive HIEs and one secretor negative line (J8). (C) At 6 dpi, the GII.3 virus shows replication in an additional secretor negative HIE (J4) while no growth of GII.4/2012-1 virus is seen. A secretor positive J2 HIE is included as control to show replication of GII.4 at 6 dpi. (A-C) Genome equivalents were determined as indicated in FIG. 15. Error bars denote standard deviation.

HuNoV infection is dependent on expression of genetically-determined histoblood group antigens (HBGAs), and genetic resistance to some HuNoV genotypes has been documented in challenge and outbreak studies (Ruvoen-Clouet, et al., 2013). The presence of a functional fucosyltransferase 2 (FUT2, secretor positive genotype) enzyme, which transfers fucose to HBGA precursors in gastrointestinal cells in secretor positive persons, correlates with susceptibility to infection with most GII.4 HuNoVs. We generated HIEs from secretor positive and negative persons to determine whether these cultures recapitulate genotype-specific patterns of HuNoV susceptibility (Saxena, et al., 2015). All secretor positive jejunal HIEs supported productive replication of GII.4 variants (44-1270 fold) and GII.3 HuNoVs (10-173 fold) based on increases in genome equivalents between 1 and 96 hpi (FIG. 18A). In contrast, GII.4 strains did not infect HIEs generated from secretor negative individuals when assayed at 96 hpi or 6 dpi (FIGS. 18B and C, respectively). However, GII.3 virus infected 2 of 3 secretor negative HIEs, one of which was positive only after 6 days in culture (FIGS. 18B and C, respectively). These results mirror epidemiologic data wherein GII.3, but not GII.4 HuNoVs, can infect some secretor negative individuals (Ruvoen-Clouet, et al., 2013) and indicate that HuNoV infection of HIEs is a biologically relevant system that mimics infections in genetically-defined individuals. Further analysis of genetically-defined HIEs will aid in determining additional host susceptibility factors to infection.

HuNoV Culture in HIEs Allows Evaluation of Virus Neutralization and Inactivation—

Figure 30:
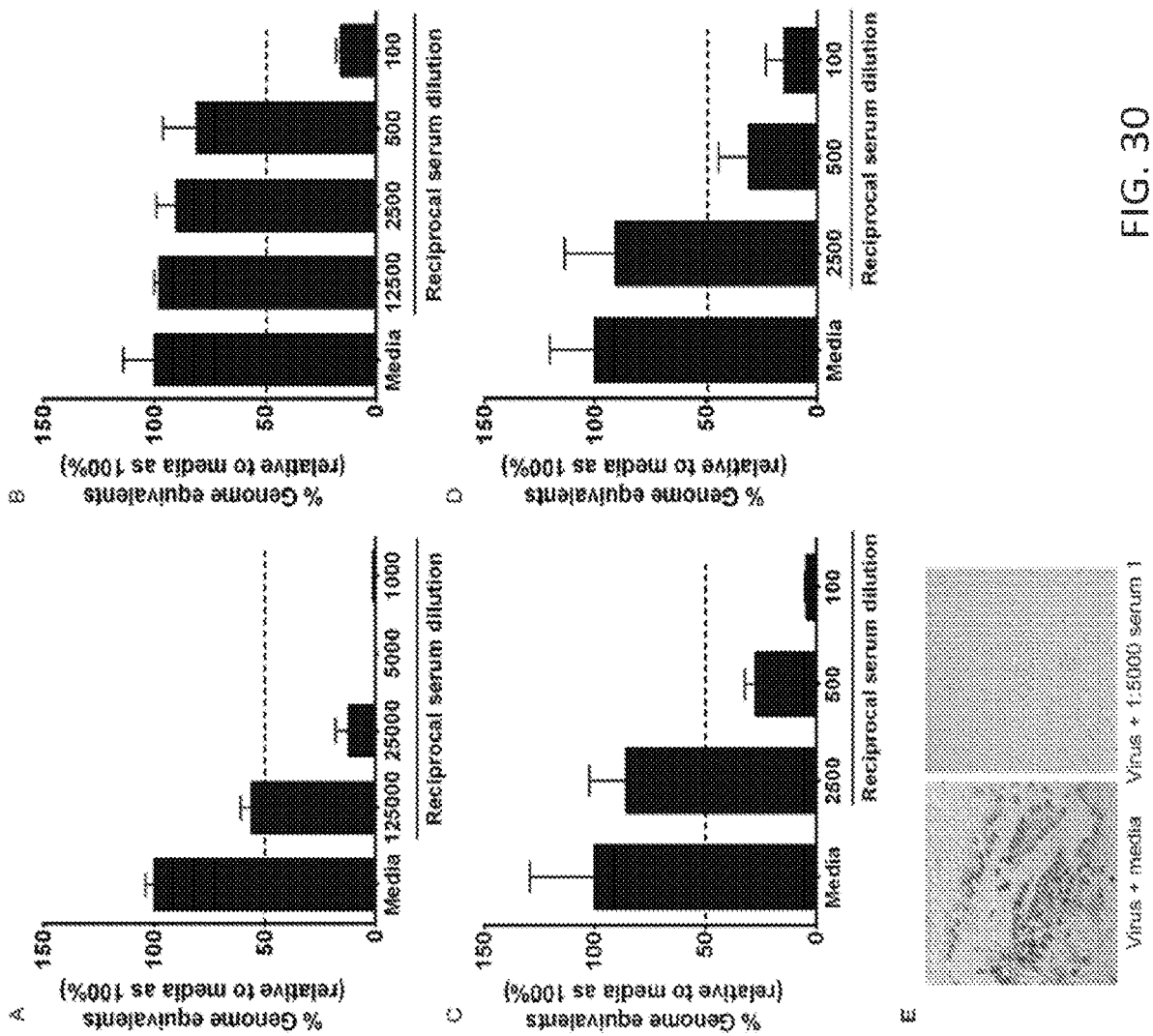
FIG. 30. Two human serum samples (1 and 2) neutralize GII.4/2012-1 and GII.3 viruses. GII.4 or GII.3 virus was mixed with an equal volume of media or dilutions of serum 1 and serum 2, and then incubated at 37° C. for 1 hr. Bile-treated human jejunal enteroids (1% sow bile for GII.4 and 5% human bile for GII.3 virus) were inoculated with each virus-serum mixture for 1 hr at 37° C. in the presence of bile. The monolayers were washed twice and then cultured in the presence of bile for 24 hr. The percent reduction in genome equivalents compared to media was determined. (A) GII.4-serum 1; (B) GII.4-serum 2; (C) GII.3-serum 1; (D) GII.3-serum 2. The dotted line represents 50% neutralization. Data are from 3 wells for each treatment. (E) GII.4/2012-1 ($5 \times 10^7$ genome equivalents) was mixed with an equal volume of media (left panel) or serial dilutions (1:250-1:5000) of serum 1, and then incubated for 1 hr at 37° C. Human jejunal enteroids were infected and CPE assessed by trypan blue exclusion at 72 hpi and imaged by bright field on an Olympus IX70 microscope with 20× magnification. CPE was observed in wells inoculated with virus and media (left panel) but CPE was not observed in any of the cultures treated with the virus-serum mixtures (1:5000 shown, right panel).

Functional antibodies in serum that block the binding of HuNoV VLPs to HBGAs correlate with protection against clinical gastroenteritis in volunteer challenge and vaccination studies (Reeck, et al., 2010; Richardson, et al., 2013; Atmar, et al., 2011). HBGA-blocking assays examine the ability of human serum to block the interaction of HuNoV VLPs with H type 1 and H type 3 glycans and porcine gastric mucin (Atmar, et al., 2006; Tan & Jiang, 2005), and the antibody titer that results in 50% blocking (BT50) has been used as a surrogate for virus neutralization (Reeck, et al., 2010). We used the HIE cultivation system to directly measure virus neutralization. Neutralizing antibody titers (the reciprocal antibody dilution present in serum able to reduce virus yields by 50% compared to virus incubated in media alone) were compared to HBGA-blocking titers. Serum samples from two individuals, one with a high BT50 and another with a low BT50 against GII.4 VLPs, were tested (Table 4). Both samples had low BT50s against GII.3 VLPs. The neutralization titers were higher than the BT50 values (Table 4 and FIG. 30A-D) and virus-induced CPE was neutralized (FIG. 30E), suggesting that virus neutralization is a more sensitive assay than the HBGA blocking assay and, besides HBGA-blocking epitopes, additional neutralization epitopes may exist on norovirus particles.

TABLE 4

Comparison of BT50 and 50% neutralization titers.

| Serum | GII.3 | | GII.4 | |
|---|---|---|---|---|
| | BT50[1] | 50% neutralization[2] | BT50[1] | 50% neutralization[2] |
| 1 | 187 | 990 | 671 | 105,000 |
| 2 | 70 | 835 | 53 | 214 |

[1]BT50 - Serum titer that blocks the interaction of HuNoV VLPs with H type 1 and H type 3 and porcine gastric mucin glycans by 50%.
[2]50% neutralization - Serum titer that reduces the infectivity of indicated HuNoV strains by 50%.

Figure 19:
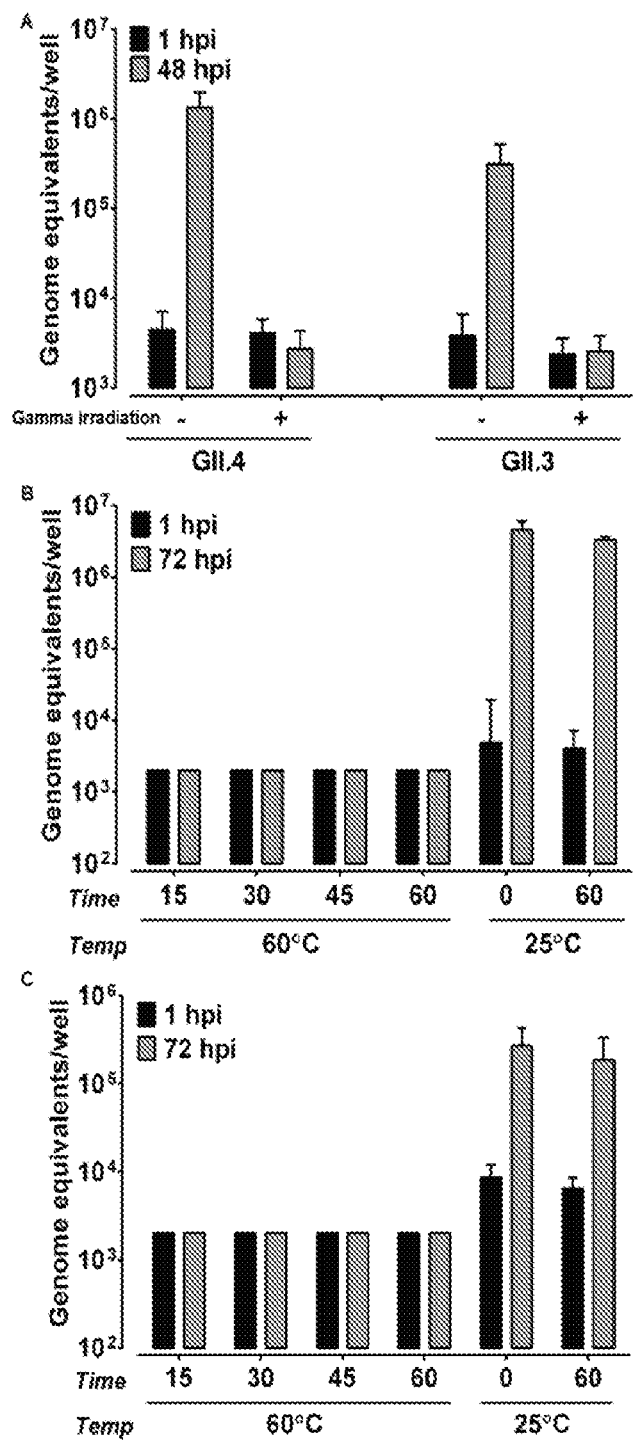
FIG. 19. Inactivation of GII.4 and GII.3 HuNoV infectivity by gamma irradiation and heat treatment. (A) GII.4/2012-1 and GII.3 HuNoVs were gamma irradiated or incubated at room temperature overnight. (B) GII.4/2012-1 or (C) GII.3 ($9 \times 10^5$ and $4.3 \times 10^5$ genome equivalents, respectively) were heat-inactivated at 60° C. for the indicated time points or incubated at room temperature for 0 and 60 minutes. Jejunal HIEs were inoculated with each sample. Genome equivalents were determined as indicated in FIG. 15. Error bars denote standard deviation.

The previous inability to cultivate HuNoVs has hampered the development of strategies to control and prevent HuNoV infection, and determination of the effectiveness of existing methods to inactivate virus to prevent transmission in various settings, including in food or on contaminated surfaces. The persistence of HuNoVs in the environment, high transmissibility and the problem of chronic infection of immunocompromised individuals document a need for antiviral treatment and prophylaxis of norovirus infections. To determine if the HIE infection model is suitable for testing virus inactivation, we evaluated GII.3 and GII.4 HuNoV inactivation by gamma irradiation and heat treatment. No growth was observed following gamma irradiation of either GII.4 or GII.3 HuNoVs (FIG. 19A). Compared to incubation of GII.4 or GII.3 viruses at room temperature for 60 minutes, both viruses were inactivated by heating at 60° C. for as little as 15 min; no increase in yield was detected from 1 to 72 hpi (FIGS. 19B and C). These studies indicate HuNoV infection of HIEs will allow evaluation of new methods to inactivate HuNoVs and to measure the effectiveness of disinfectants and sanitizers, including characterization of the efficacy of both traditional and novel control measures.

Implications of In Vitro Replication of HuNoV for Understanding its Biology—

HuNoV was visualized by Albert Kapikian in 1972, but conditions to grow these viruses in vitro have remained an unsolved mystery for more than 40 years. We demonstrate the successful development of a robust in vitro replication system for multiple HuNoV strains and provide insights into HuNoV strain-specific growth requirements. HuNoV replication in HIEs is robust based on achieving several $\log_{10}$ increases in replication of multiple variants of the epidemiologically predominant GII.4 HuNoVs in HIE lines from different small intestinal segments from multiple immunocompetent individuals; replication was documented by expression of structural and nonstructural proteins, production and release of virus particles into culture supernatants, and successful passaging of virus. The cultivation system described in this study has biologic relevance with replication of different strains being consistent with known host restriction based on HBGA expression. Variability in replication between different HIE cultures is observed; specific cultures (secretor positive) are highly susceptible to HuNoV strains and other cultures (secretor negative) show variable resistance to infection with specific HuNoV strains. These results mirror infectivity patterns seen in epidemiological studies. Future work with additional strains is needed to understand the basis for this variability particularly for infection of different secretor negative lines with GII.3 viruses.

HuNoVs replicate in enterocytes from different intestinal segments in HIEs. In addition, factors present in the intestinal milieu, such as bile, enhance or are required for replication to occur. Bile obtained from various mammalian sources (human, sow, piglet, porcine and bovine) mediate this effect, although there is variability between bile sources and virus strains. These results are consistent with previous data from intestinal biopsies from HuNoV-infected immunocompromised transplant patients and studies in large animals (gnotobiotic pigs and newborn calves) infected orally with HuNoV GII.4 or bovine norovirus GIII. 1 strains, respectively, where enterocytes in different segments of the small intestine are clearly infected and express viral antigen (Cheetham, et al., 2006; Otto, et al., 2011; Karandikar, et al., 2016). Filtered stool was used as inoculum in the present study and bacterial LPS was not required for infectivity. These results differ from reports of cultivation of a single strain of HuNoV in B cells where unfiltered inocula and commensal bacteria are required as co-factors (Jones, et al., 2015; Jones, et al., 2014), and of HuNoV replication in other animal models following non-oral routes of inoculation, including intraperitoneal injection of immunodeficient mice (Taube, et al., 2013) or intravenous injection of chimpanzees (Bok, et al., 2011); in those models, virus was not detected in intestinal epithelium but in cells in the lamina propria with some expressing DC-SIGN (chimpanzees) or with a macrophage-like morphology (mice). Replication of HuNoVs in enterocytes in HIEs supports the observation that another site(s) of primary replication besides B cells must exist because HuNoVs can infect B-cell deficient patients (Green, 2016; Brown, et al., 2016). Our results are reminiscent of initial conditions that required the addition of intestinal contents from gnotobiotic piglets to successfully culture a porcine enteric calicivirus (PEC), a member of the Sapovirus genus of the Caliciviridae family, using primary porcine kidney cells (Flynn, et al., 1988). Species-specific bile enhanced primary replication in that system and subsequent studies showed that bile acids and a continuous porcine kidney cell line can support PEC replication (Chang, et al., 2004). Additional studies are needed to determine the active components of bile needed to support HuNoV replication in HIEs. The active component(s) in bile and mechanism(s) of action required for HuNoV cultivation in HIEs remain to be fully characterized but initial characterization demonstrates that it is not a protein. The establishment of this new cultivation system will facilitate applications in many different realms of public health importance such as food safety, development of new diagnostics, vaccines and therapeutics, and advance research on HuNoV evolution, immunity and pathogenesis.

Material and Methods

Human Intestinal Enteroid (HIE) Cultures.

HIE cultures were derived from biopsies from adults during routine endoscopy or from surgical specimens obtained during bariatric surgery. The biopsies were taken from healthy regions of intestinal tissue as assessed by the physician who obtained the tissues. HIEs were grown as multilobular, 3-dimensional (3D) cultures in Matrigel and maintained as previously described (Saxena, et al., 2015). For all infections, monolayer cultures in 96 well plates or transwells (BD 3413) were prepared from the 3D cultures using a protocol modified from (VanDussen, et al., 2015). Each well of a 96 well plate or transwell was coated with 2.5 µl of Matrigel diluted in 100 µl ice-cold PBS that was removed after 90 min incubation at 37° C. Multilobular, 3D HIEs (50 HIEs/well for a 96 well plate or 100 HIEs/transwell) were washed with 0.5 mM EDTA in ice cold PBS (without calcium chloride-magnesium chloride) and dissociated with 0.05% trypsin/0.5 mM EDTA for 4 min at 37° C. Trypsin was then inactivated by adding FBS diluted in complete medium without growth factors [CMGF(−)] to the cell suspension at a final concentration of 10%. Single cell suspensions were prepared from the 3D HIEs following dissociation of the cells by pipetting with a P1000 pipet and passing the cells through a 40 µm cell strainer. The cells were pelleted for 5 min at 400×g, suspended in 100 µl of complete medium with growth factors [CMGF(+)] containing the ROCK inhibitor Y-27632 (10 µM, Sigma), and seeded in a single well of 96-well plate or a transwell. For transwells, 600 µl of CMGF(+) medium containing 10 µM Y-27632 was added to the lower compartment of the well. After 24 hours of growth, the culture medium was changed to differentiation medium to differentiate the cells for 4 days. Differentiation medium consisted of the same components as those of CMGF(+) medium without the addition of Wnt3A, SB202190, and nicotinamide as well as 50% reductions in the concentrations of Noggin and R-spondin. The secretor status of each enteroid line was determined by genotyping and previously described (Saxena, et al., 2015) and expression of HBGAs was confirmed by staining with UEA-1 lectin. Enteroid cultures are available under a Materials Transfer Agreement.

Stool Filtrates.

To prepare 10% stool suspensions (see Table 3), PBS was added to HuNoV-positive or -negative stools, which were then homogenized by vortexing and sonicated three times for 1 min. The sonicated suspensions were centrifuged at 1,500×g, 10 min at 4° C. The supernatant was transferred to a new tube, centrifuged for a second time, and the resulting supernatant was passed serially through 5 μm, 1.2 μm, 0.8 μm, 0.45 μm and 0.22 μm filters. The filtered samples were aliquoted and frozen at −80° C. until used. A 25% suspension of the GI.1 stool filtrate was prepared as previously described (Ramani, et al., 2015). To determine the effect of LPS on HuNoV infection, HIE monolayers were infected with $2.5 \times 10^5$ genome equivalents of GII.4/2012-1 stool filtrate that was either treated or not treated with 100 μg/ml polymyxin B (Sigma) for 1 hour at room temperature (Lay, et al., 2010). The endotoxin (LPS) level in each sample was determined by the Limulus amebocyte lysate (LAL) QCL1000 kit (Lonza) according to the manufacturer's instructions. To determine the effect of LPS on HIE monolayers, monolayers were cultured in the presence or absence of 10 μg/ml LPS for 4 days and then cytotoxicity was evaluated by trypan blue exclusion.

Cell Lines.

Vero, African green monkey kidney epithelial cells; Huh7, hepatocyte-derived cellular carcinoma cells; 293FT, human embryonic kidney cells that stably express the SV40 large T antigen; and Caco-2 BBe, human epithelial colorectal adenocarcinoma cells were grown in DMEM containing 10% FBS and penicillin and streptomycin. The Caco-2 BBe cell medium also contained 1% nonessential amino acids. Undifferentiated Caco-2 BBe cells were cultured for 3 days and differentiated Caco-2 BBe cells were cultured for 21 days.

Bile.

Waste human bile, obtained from adults undergoing hepatobiliary surgery, was collected through the Texas Medical Center Digestive Diseases Center Study Design and Clinical Research Core. The study protocol was approved by the Baylor College of Medicine Institutional Review Board. Bile was collected from sows and piglets under a study protocol approved by the Animal Care and Use Committee of Baylor College of Medicine and was conducted in accordance with the Guide for the Care and Use of Laboratory Animals [DHHS publication no. (NIH) 85-23, revised 1985, Office of Science and Health Reports, DRR/NIH, Bethesda, Md. 20205]. Bovine and porcine bile were commercially obtained (Sigma) and a 30% weight/volume solution was prepared in PBS. To determine if the active component of bile enhancing HuNoV infection was a protein, human bile was heated to 100° C. for 5 min and immediately chilled on ice. Alternatively, human bile was incubated with or without 167 μg/ml trypsin (Worthington Biochemical) for 24 hours at 37° C., followed by the addition of soybean trypsin inhibitor [31.2 μg/ml final concentration (Merck Millipore)] to inactivate the trypsin. Heat- or trypsin-treated bile was added to medium at the concentration of 5% during infection as described below.

Human Norovirus (HuNoV) Infection of HIE Monolayers, Transwells or Other Cell Lines.

All experiments were performed on monolayer cultures of HIEs in 96-well plates or transwells because of the ease of infecting monolayers rather than 3D HIEs that require additional centrifugation steps and manipulation for infecting. Some experiments (FIG. 15A-F, FIGS. 21A and B, and FIG. 22A-C) were performed in the absence of bile. For other experiments monolayers were pretreated with bile for 48 hours prior to infection. For experiments in FIG. 16Fb-e, bile was added for various times before and after adsorption as indicated. For inoculation, the HIE cell monolayers or transwells were washed once with CMGF(−) medium and mock-inoculated or inoculated with HuNoV diluted in CMGF(−) medium containing bile for 1 hour at 37° C. The inoculum was removed and monolayers were washed twice with CMGF(−) medium to remove unbound virus. Differentiation medium containing bile was then added and the cultures were incubated at 37° C. for the indicated time points. The source of bile and concentration used is indicated in each figure. Due to the limited amount of human bile, this bile was primarily used for GII.3 infections, and bile from other sources (bovine, porcine, sow and piglet) was used for GII.4 infections. Because differences in cytopathic effects (CPE), assessed by trypan blue exclusion, or RT-qPCR signal were not observed between HuNoV-negative stool- or mock-inoculated cultures, most mock-inoculation experiments described were performed using CMGF (−) medium. CPE was not observed in HuNoV-negative stool or mock-inoculated cultures. Infected monolayers on 96 well plates were used for all RT-qPCR and growth studies while infected monolayers on transwells were used for high resolution confocal microscopy studies. High multiplicities of infection (MOI) were used for confocal microscopy, flow cytometry and Western blotting to ensure that protein would be detected at early time points post infection. In contrast, lower MOIs were used for RT-qPCR experiments. The input virus used for each experiment is given in each figure legend.

GII.4/2009 HuNoV was passaged in jejunal HIE monolayers with 2% piglet bile as described above. After 5 days post-infection, cells and media were subjected to two freeze/thaw cycles and sonicated three times for 1 min. For each subsequent passage, 20 μl of virus stock from the previous passage was used to infect jejunal HIE monolayers as described above.

Reverse Transcriptase Quantitative Polymerase Chain Reaction (RT-qPCR).

At the indicated time points, 300 μl of Ribozol™ (Amresco) was added to each mock- and HuNoV-inoculated HIE well containing cells and supernatant and RNA was extracted. RNA extracted at 1 hpi, used as a baseline to account for input virus that remained associated with cells, was from cultures where the inoculum was removed, the cells were washed twice to remove unbound virus and differentiation medium was added. For RT-qPCR, the primer pair p165/p166 and the probe p167 were used for GI (Atmar, et al., 2008) and the primer pair COG2R/QNIF2d and probe QNIFS were used for GII (Loisy, et al., 2005; Kageyama, et al., 2003) with qScript XLT One-Step RT-qPCR ToughMix reagent with ROX (Quanta Biosciences). Reactions were performed on an Applied Biosystems StepOnePlus thermocycler in a 15 μl reaction volume using the following cycling conditions: 50° C. (15 min), 95° C. (5 min), followed by 40 cycles of 95° C. (15 sec) and 60° C. (35 sec). A standard curve based on a recombinant HuNoV RNA transcript was used to quantitate viral genome equivalents in RNA samples (Guix, et al., 2007; Le Guyader, et al., 2008).

Electron Microscopy (EM).

To visualize HuNoV particles, supernatant from infected jHIE monolayers (20 hpi) was clarified by centrifugation at 8,000×g for 10 min. The particles were either directly visualized by EM or were pelleted through a 30% (w/v) sucrose cushion at 135,000×g for 1.5 hours. After staining with 1% ammonium molybdate (pH 5.5), particles were visualized using a JEOL 1230 transmission electron microscope (JEOL USA) with a Gatan Ultrascan 1000 CCD and Digital Micrograph Software (Gatan).

Immunofluorescence.

HIE monolayers on 96 well plates or transwells were fixed with methanol for 20 min at −20° C., 4% paraformaldehyde (PFA) at room temperature for 20 min or fixed in 10% formalin and embedded in paraffin. Transwell cultures were used to obtain high resolution confocal images to determine what cell types are infected by HuNoVs. Cells were blocked for 2 hours in 0.01 M PBS containing 5% BSA. Primary antibodies were incubated overnight at 4° C. Expression of the capsid protein (VP1) was detected using antisera to guinea pig anti-GII.4/2012 virus-like particles (VLPs) [(1:250) made by Covance, Princeton, N.J. as previously described by (Jiang, et al., 1992)] or anti-GII.3 (TCH04-577) VLPs (1:250), or to non-structural proteins [rabbit anti-U201 polymerase (Pol, 1:100), anti-NTPase (1:100), or anti-VPg (1:100)] (Katayama, et al., 2014). Double-stranded RNA (dsRNA) was detected using the J2 monoclonal antibody (1:100, Scicons). Expression of differentiation markers was detected using antisera raised against sucrase isomaltase (1:100, Santa Cruz), mucin 2 (1:500, Santa Cruz), chromogranin A (1:100, Novus Biologicals), or villin (ready to use, Cell Marque). HBGAs and actin were stained with UEA-1 lectin (1:500, Sigma) and phalloidin (1:1000, Sigma), respectively, that were directly conjugated with Alexa 549. After washing with 0.01 M PBS, the cells were incubated for 2 hours at room temperature with the corresponding secondary antibody conjugated to Alexa Fluor 594 or 488 (1:1500, Invitrogen). Nuclei were stained with 300 nM DAPI for 15 min at room temperature. After the final wash step, the monolayers in the 96 well plate were imaged in PBS while the monolayers on transwells were mounted in prolong gold (Thermo Fisher). The immunofluorescence was detected with an IX-70 inverted microscope (for HIE monolayers in 96-well plates) or a Nikon A1-Rs inverted laser-scanning microscope (for HIE monolayers on transwells or optical bottom 96 well plates).

Hematoxylin and eosin (H&E) staining was performed on deparaffinized sections. Sections were incubated in hematoxylin for 1 min, rinsed with tap water, immersed in 95% ethanol, counterstained with eosin for 30 seconds and then dehydrated and mounted in Permount™ mounting medium.

Western Blot Analysis.

Proteins in mock- and HuNoV-inoculated HIEs were detected by Western blot analysis. Briefly, supernatants (100 µl per well) of mock- and HuNoV-infected monolayers in 96-well plates were collected at indicated time points and monolayers were lysed in 50 µl/well NP-40 lysis buffer [50 mM Tris-HCl pH7.5, 150 mM NaCl, 1% NP-40, 10% glycerol, 1 mM DTT, 1× protease inhibitor cocktail (CalBiochem)]. Each cell lysate was clarified by centrifugation and 10-15 µl lysate or supernatant was subjected to SDS-PAGE and Western blotting. Proteins were separated on 4-15% SDS-PAGE and then transferred to nitrocellulose membranes. VP1 expression was detected with guinea pig anti-GII.4/2012 VLP serum (1:2,000). VPg-containing polyprotein processing intermediates were detected using a rabbit polyclonal antiserum to HuNoV GI. 1 strain Norwalk virus (NV) VPg (1:1000), which broadly detects VPg of HuNoV GII strains, as described previously (Katayama, et al., 2014). Actin was detected as a loading control with a mouse monoclonal anti-actin antibody (1:5000, Abcam). Species-specific HRP-conjugated secondary antibodies (1:20000, Sigma) were used to detect the primary antibodies. A lysate of HEK293FT cells transfected with pHuNoVSagalF, an expression plasmid of HuNoV GII.4 strain Saga1 full-length genome at 24 hours post transfection was used as a positive control for detection of VPg-containing polyprotein processing intermediates and the mature VPg, as described previously (Katayama, et al., 2014).

Flow Cytometry.

Human intestinal enteroid cells were harvested from monolayers on 96-well plates after mock-inoculation or infection with HuNoV (GII.4/2012-1, $9 \times 10^7$ genome equivalents) by incubation with 100 µl of 0.05% trypsin-EDTA (Gibco) for 5 min at 37° C. Trypsin was inhibited by addition of 1 ml DMEM with 8% FBS. Cells were pelleted by centrifugation at 400×g for 5 min and suspended in 500 µl of Cytofix (BD Biosciences) for 10 min at 4° C. All washes were carried out twice with Stain Buffer (BD Biosciences) containing 0.5% BSA followed by pelleting each time. Cells were washed, suspended in 900 µl of −20° C. methanol, and incubated at 4° C. for 30 min. Cells were washed and suspended in Stain Buffer containing 5% BSA and guinea pig anti-GII.4/2012 VLP or preimmune antibody (1:20000). The cells were incubated with antibody for 30 min at room temperature, pelleted and washed. The cell pellet was suspended in Stain Buffer containing 5% BSA and goat anti-guinea pig Alexa 488 antibody (1:500) and incubated for 30 min at room temperature in the dark. The cells were pelleted and after the final wash, cells were suspended in 500 µl of Stain Buffer containing 0.5% BSA and analyzed using a LSR II flow cytometer (BD Biosciences). Control mock-inoculated cells were incubated with goat anti-guinea pig Alexa 488 antibody or with guinea pig anti-GII.4/2012 VLP or preimmune antibody, and then goat anti-guinea pig Alexa 488 antibody to assess non-specific binding.

Inactivation of HuNoV.

a) Virus Neutralization Assays.

Serial dilutions of two serum samples were carried out in CMGF(−) medium. GII.4/2012-1 or GII.3 virus ($2.5 \times 10^5$ genome equivalents) were mixed with an equal volume of media or dilutions of each serum sample and incubated at 37° C. for 1 hour. CMGF(−) containing 1% sow bile for GII.4 or 5% human bile for GII.3 was added to each sample and inoculated onto bile-treated HIEs for 1 hour as described above. To determine whether virus-induced CPE was neutralized by human serum, $5 \times 10^7$ genome equivalents of GII.4/2012-1 was mixed with an equal volume of media or dilutions of each serum sample and incubated at for 1 hour at 37° C. CMGF(−) containing 1% sow bile was added to each sample and inoculated onto HIEs for 1 hour as described above. CPE was assessed by trypan blue exclusion as described above.

b) Heat Inactivation of Human Noroviruses.

GII.4 and GII.3 HuNoV stool filtrates ($9 \times 10^5$ and $4.3 \times 10^5$ genome equivalents, respectively) were heat-treated in a digital dry heat block at 60° C. for the indicated time periods or incubated at 25° C. for 0 and 60 min. The treated virus was placed on ice after completion of incubation to stop the heat treatment. Each sample was inoculated onto a HIE monolayer treated with 1% sow bile for GII.4 or 5% human bile for GII.3 as described above.

c) Inactivation of HuNoVs by γ-Irradiation.

GII.4 and GII.3 HuNoV stool filtrates were exposed to 8 kilo Grays (kGy) of γ-irradiation at room temperature using a Gammacell-1000 Irradiator (Atomic Energy of Canada Ltd.) with a Cesium-137 source, at a dose rate of 0.5 kGy/hour. Unexposed HuNoVs were incubated at room temperature for the same length of time as the exposed samples. Each sample was inoculated onto a HIE monolayer treated with 1% sow bile for GII.4 or 5% human bile for GII.3 as described above.

Statistical Analysis.

Each experiment was performed two or more times, with three technical replicates of each culture, condition and time point in each experiment. Data from 1 representative experiment is presented. All statistical analyses were performed on GraphPad Prism version 6.0 for Windows (GraphPad Software, La Jolla Calif. USA). Samples with RNA levels below the limit of detection of the RT-qPCR assay were assigned a value that is one-half the limit of detection of the assay. Comparison between groups was performed using the Students t-test, with statistical significance determined using the Holm-Sidak method. P-values<0.05 were considered statistically significant. A sigmoidal, 4-parameter logistic curve was used to calculate 50% neutralizing antibody titers.

Example 4

Figure 31:
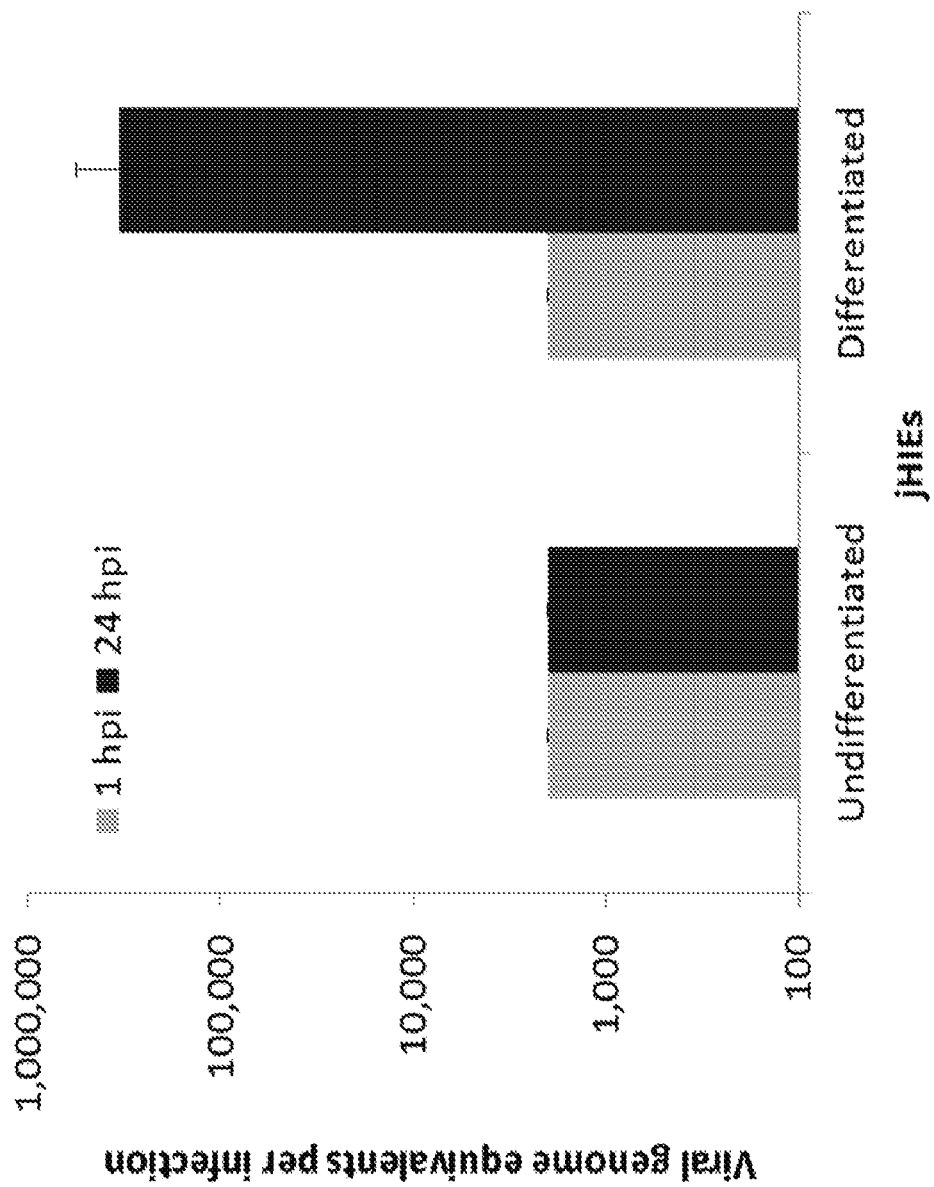
FIG. 31. Effect of differentiation status on susceptibility to HuNoV infection. Undifferentiated and differentiated jejunal enteroids were infected with HuNoV GII.4_Sydney. The amount of infectious virus was quantified at 1 hpi (light blue bars) and 24 hpi (dark blue bars). Error bars denote standard deviation. The experiment was performed two times, with three technical replicates in each condition in each experiment.
Figure 32:
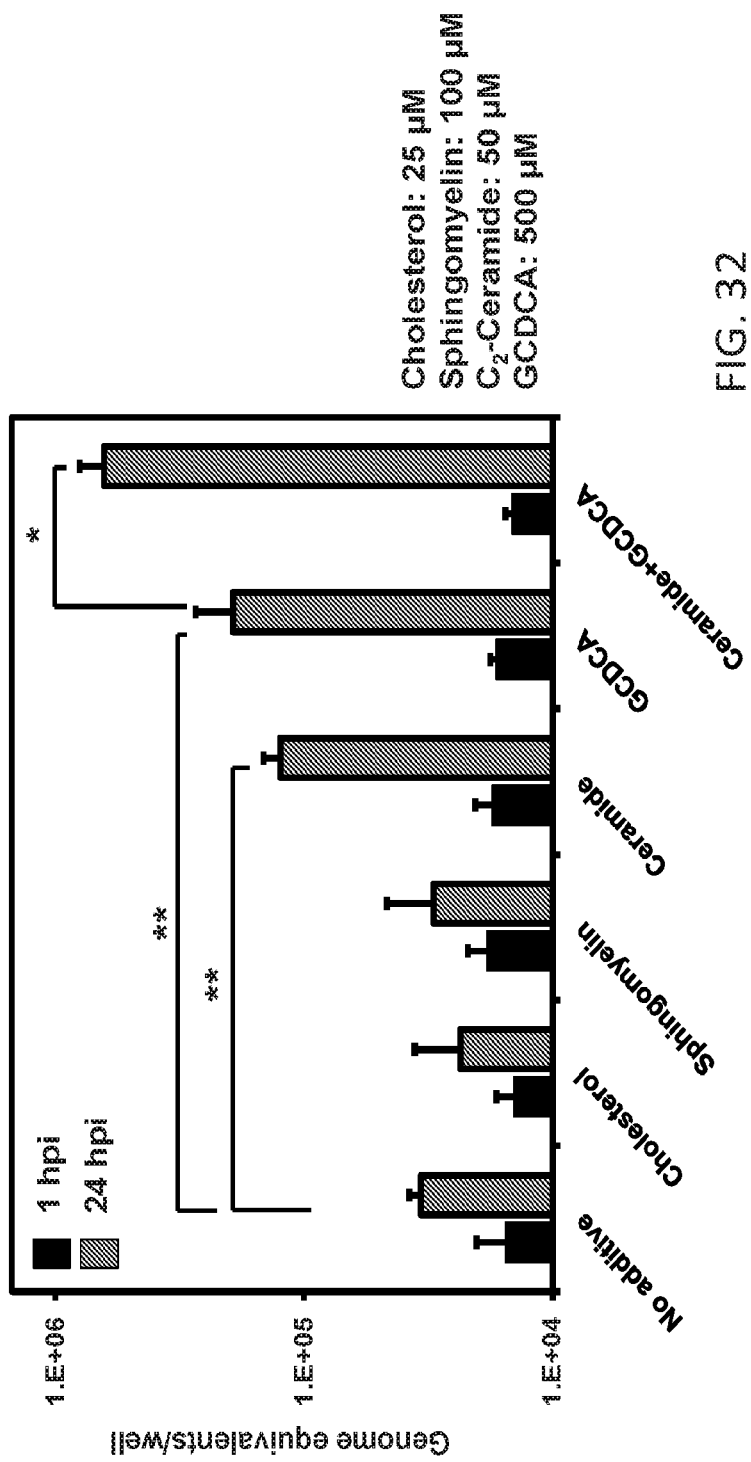
FIG. 32. At least one lipid, ceramide, enhances GII.3 HuNoV replication alone or in combination with the bile acid GCDCA. J2 jHIE monolayers (p.12) were inoculated with $4.3 \times 10^5$ genome equivalents of TCH04-577 for 1 hr, and after washing twice with CMGF(−) media to remove unbound virus, culture continued in differentiation medium for 24 hrs. The amount of infectious virus was quantified after the washing at 1 hpi (black bars) and at 24 hpi (gray bars). Additives were added to the medium during and post inoculation. Error bars denote standard deviation. *, $p<0.05$ comparing genome equivalents between GCDCA and ceramide+GCDCA at 24 hpi; **, $p<0.01$ comparing genome equivalents between ceramide and GCDCA, and no additive at 24 hpi.
Figure 33:
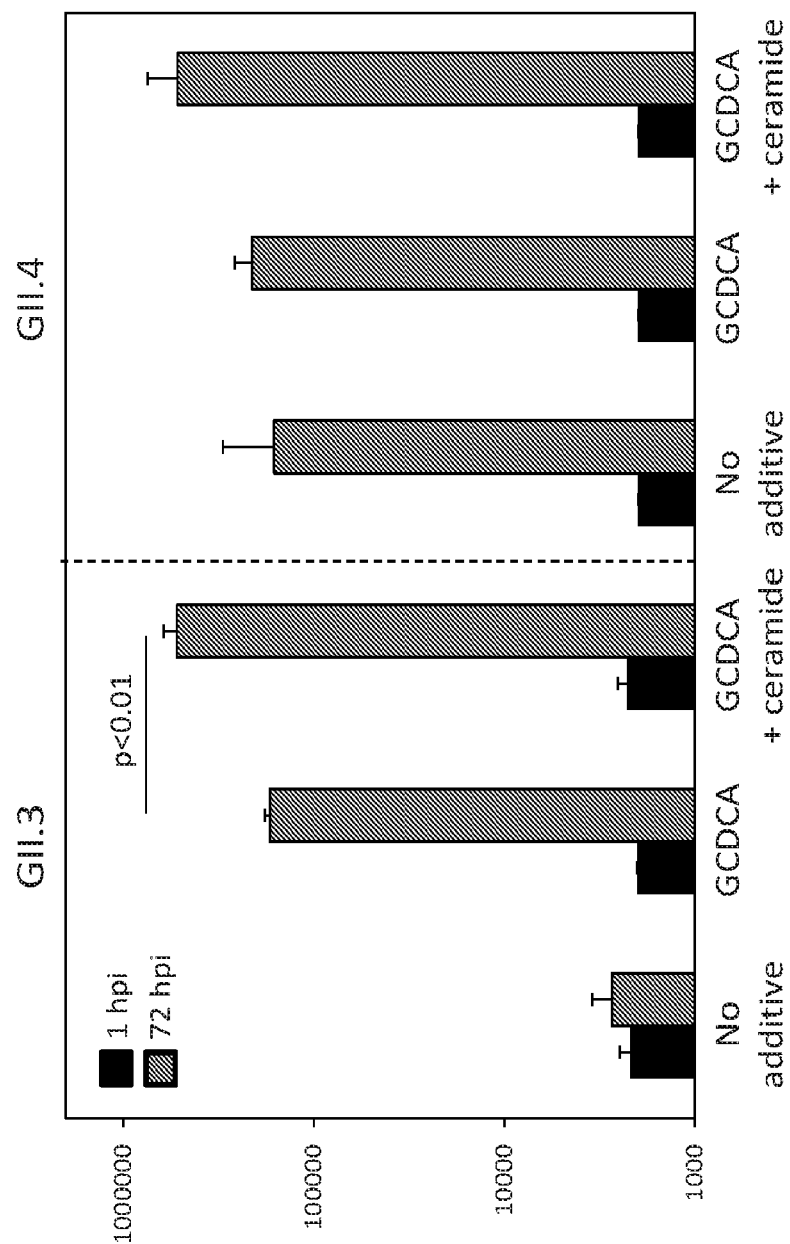
FIG. 33. Ceramide alone, or in combination with the bile acid GCDCA, enhances GII.3 but not GII.4 HuNoV replication. J2 jHIE monolayers (p.23) were inoculated with $4.3 \times 10^5$ or $9 \times 10^5$ genome equivalents of TCH04-577 or TCH12-580, respectively, for 1 hr and, and after washing twice with CMGF(−) media to remove unbound virus, culture continued in differentiation medium for 72 hrs. The amount of infectious virus was quantified after the washing at 1 hpi (black bars) and 72 hpi (gray bars). Additives (500 µM GCDCA or 500 µM GCDCA+50 µM C2-ceramide) were added to the medium during and post inoculation. Error bars denote standard deviation. $p<0.01$ comparing genome equivalents at 72 hpi between GCDCA and ceramide+ GCDCA.

Embodiments of Inclusion of Differentiation, Ceramide, Lipid Rafts and Host Receptors for Infection FIG. 31 demonstrates that human norovirus GII.4 preferentially infects differentiated enteroids. FIG. 32 shows Ceramide enhances GII.3 replication and further enhances replication when combined with the bile acid GCDCA. Addition of bile acid GCDCA and ceramide significantly enhances GII.3 replication but not GII.4 replication is demonstrated in FIG. 33. Thus, the lipid ceramide enhances infectivity when given either alone or with GCDCA indicates that at least in some embodiments that bile acids are not the sole component of bile that is active in allowing human norovirus to grow.

Figure 34:
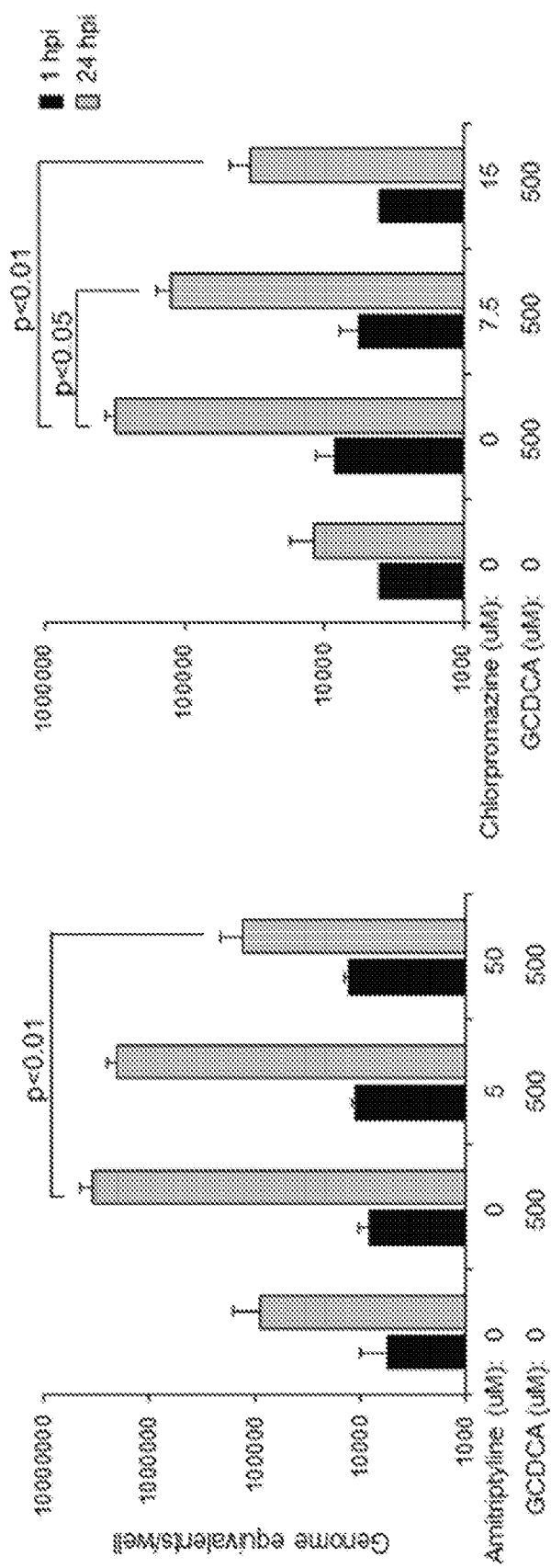
FIG. 34. Acid sphingomyelinase (ASM) inhibitors suppress GII.3 HuNoV replication. Jejunal enteroids were pretreated with inhibitors for 1 hr and inoculated with TCH04-577 for 1 hr, washed twice with CMGF(−) and cultured for 24 hrs in the presence of the inhibitors. RNA was extracted from cells and medium at 1 and 24 hpi and genome equivalents were analyzed by RT-qPCR.

Acid sphingomyelinase (ASM) that converts sphingomyelin into ceramide is involved in HuNoV infectivity, in at least certain embodiments. Incorporation of ceramide into lipid rafts by ASM clusters receptors and recruits intracellular signaling molecules to lipid rafts and has been shown to be involved in *P. aeruginosa, S. aureus, N. gonorrhoeae*, Sindbis Virus, and Rhinovirus infection. GII.3 replication was significantly reduced in the presence of two ASM inhibitors amitriptyline and chlorpromazine. A dose-dependent decrease in GII.3 replication was observed in the presence of amitriptyline and chlorpromazine (FIG. 34).

Figure 35:
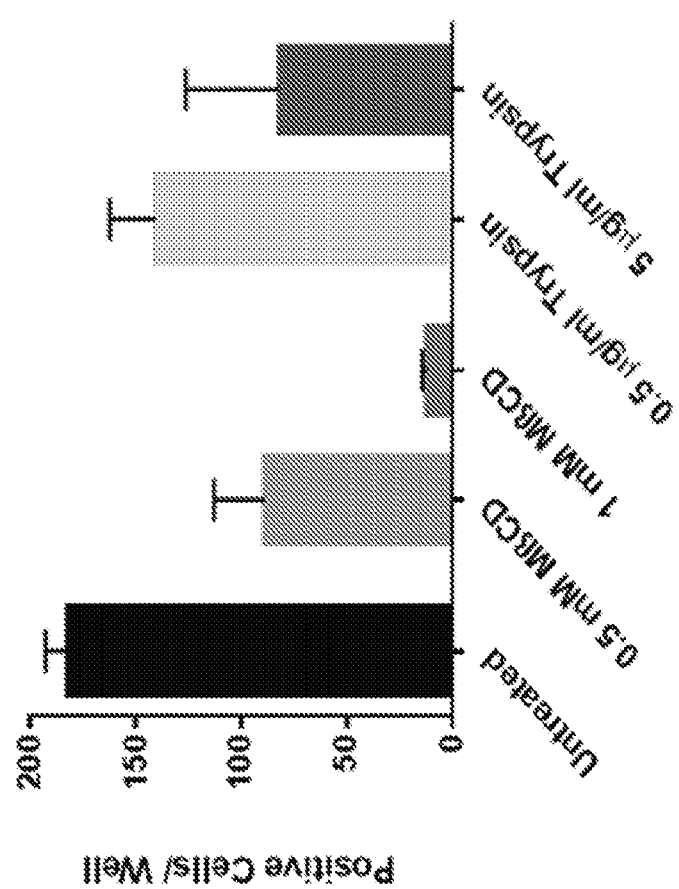
FIG. 35. Cholesterol extraction using methyl-β-cyclodextrin or treatment of cells with trypsin reduces HuNoV infection. Jejunal enteroids were untreated or treated for 45 min with methyl-β-cyclodextrin (MβCD) or 15 min with trypsin. Trypsin was inhibited with aprotinin and then the monolayer was washed prior to infection. MβCD was present during and after infection. Enteroids were infected with $3 \times 10^6$ genome equivalents of TCH11-64 GII.4 HuNoV. Enteroid monolayers were fixed at 24 hpi, VP1 detected by immunofluorescence and the number of VP1-positive cells counted per well.

In specific embodiments of the disclosure, HuNoV use a proteinaceous receptor in lipid rafts for infection. Lipid rafts are specialized domains of the cell membrane and are central for the spatial organization of receptors and signaling molecules. Extraction of cholesterol from lipid rafts using methyl-β-cyclodextrin significantly reduced GII.4 infection (FIG. 35) indicating that the integrity of lipid rafts are important for replication. Treatment of cells with trypsin that cleaves proteins reduced GII.4 infection (FIG. 35) indicating that a proteinaceous receptor in lipid rafts may be involved in HuNoV infection. Identification of the proteinaceous molecule(s) that function as the receptor for HuNoV replication will allow production of new, simple cell systems that express this receptor and that will support HuNoV replication.

Example 5

Embodiments of Inclusion of New Strains and Virus Neutralization

Figure 36:
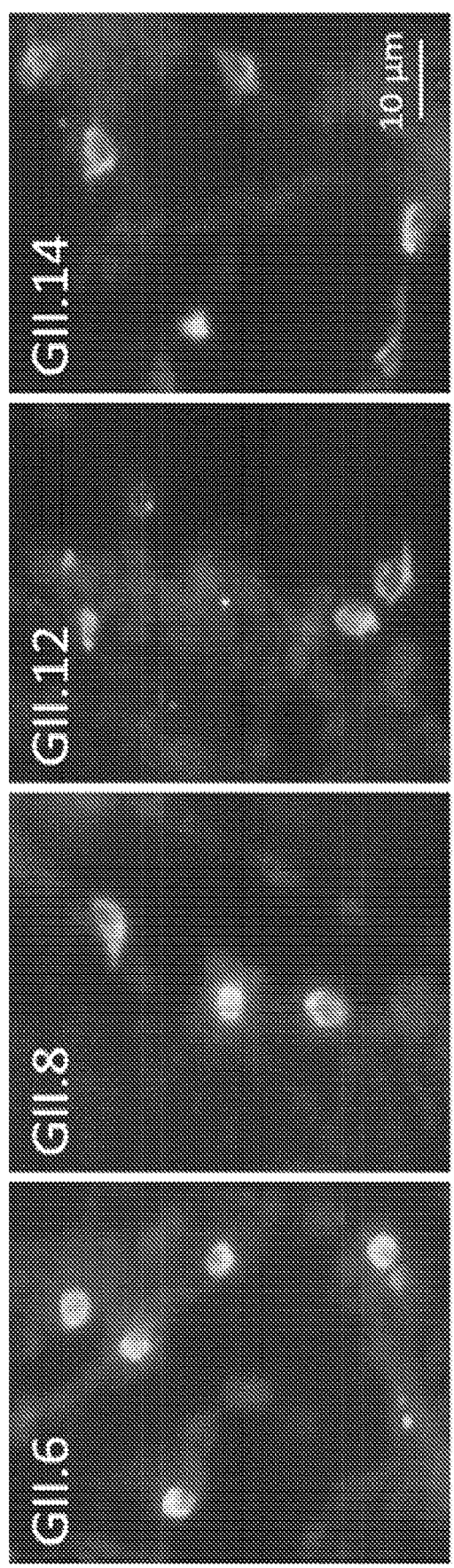
FIG. 36. Additional HuNoV strains replicate in HIEs. Jejunal HIE monolayers were inoculated with 10% stool filtrates. The monolayers were fixed with methanol 24 hpi and the VP1 capsid protein detected with a guinea pig anti-GII.4 Sydney VLP antibody by immunofluorescence. VP1-positive cells are shown in green.

HuNoV strains in addition to GII.3 and GII.4 are cultivated in the HIEs. In particular, GII.6, GII.8, GII.12 and GII.14 (FIG. 36) are cultivated in the HIEs. Thus far, 7 different GII strains, including 4 GII.4 variants and one GI strain, have been cultivated in the HIEs.

Figure 37:
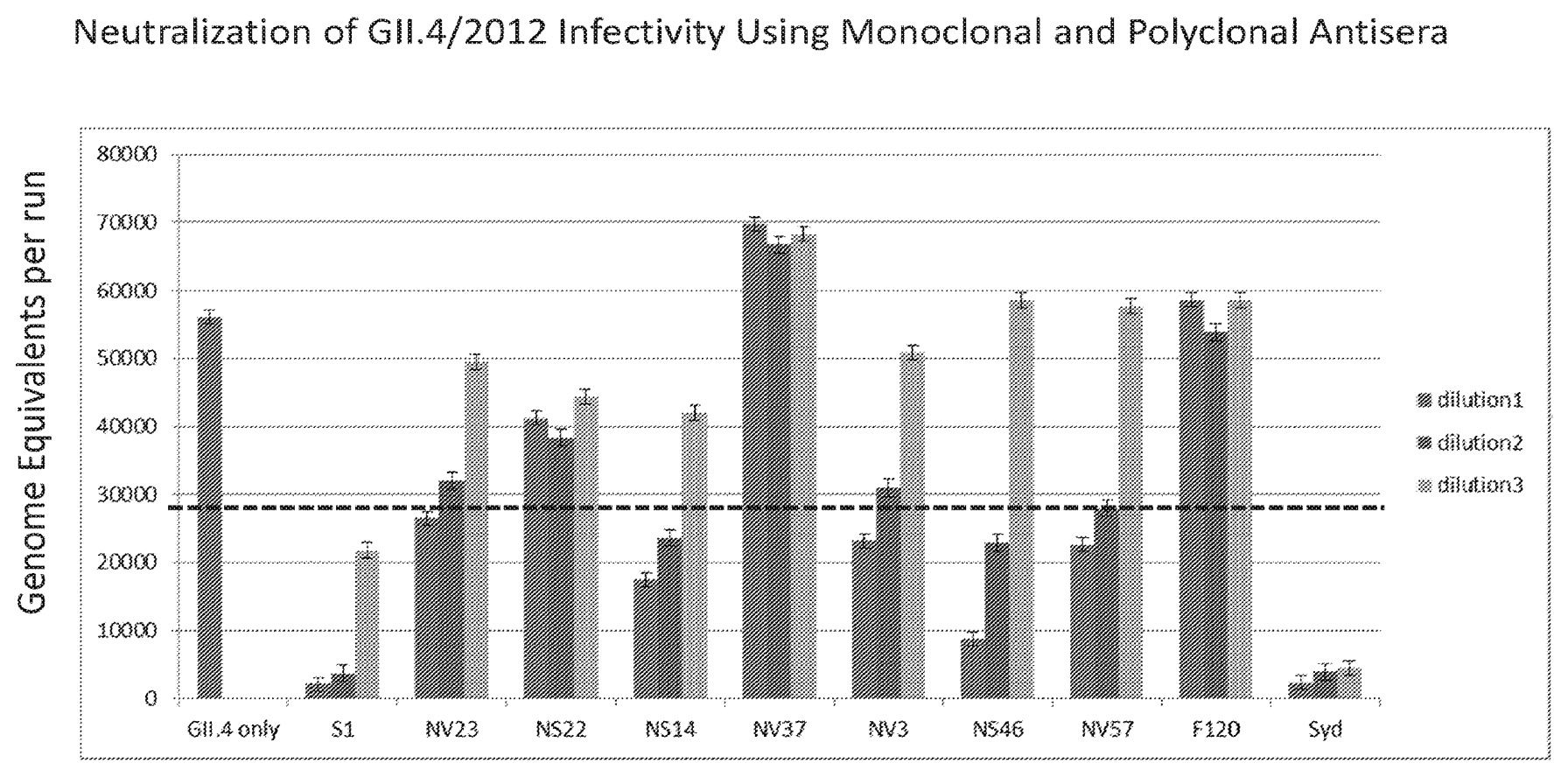

Neutralization of GII.4/2012 infectivity using monoclonal and polyclonal antisera is demonstrated in FIG. 37. The monoclonal antibodies tested bind the capsid but do not block virus binding to histoblood group antigens, but this data shows they have some neutralization activity. Monoclonal antibodies NV23, NS14 and NS46 bind to HuNoVs by enzyme-linked immunoassay and the regions that NS14 and NV23 bind have been mapped. This result indicates that additional neutralization epitopes exist on norovirus besides histoblood group antigen-blocking epitopes.

In particular embodiments, a neutralization assay is employed to screen antibodies (such as Intravenous Immunoglobulin; IVIG) to determine if these pools comprise neutralizing antibodies to human norovirus to choose pools to test and treat patients with chronic norovirus infection.

REFERENCES

All publications mentioned in this specification are indicative of the level of those skilled in the art to which the invention pertains. All publications herein are incorporated by reference to the same extent as if each individual publication was specifically and individually indicated to be incorporated by reference in their entirety.

1. Atmar, R. L. and M. K. Estes. 2012. Norovirus vaccine development: next steps. Expert. Rev Vaccines. 11:1023-1025.
2. Atmar, R. L., A. R. Opekun, M. A. Gilger, M. K. Estes, S. E. Crawford, F. H. Neill, S. Ramani, H. Hill, J. Ferreira, and D. Y. Graham. 2014. Determination of the 50% human infectious dose for Norwalk virus. J Infect Dis 209:1016-1022.
3. Duizer, E., K. J. Schwab, F. H. Neill, R. L. Atmar, M. P. Koopmans, and M. K. Estes. 2004. Laboratory efforts to cultivate Noroviruses. J Gen. Virol 85:79-87.
4. Green, K. Y. 2013. Caliciviridae: The Noroviruses, p. 582-608. In D. M. Knipe and P. M. Howley (eds.), Field's Virology. Lippincott Williams & Wilkins, Philadelphia.
5. Herbst-Kralovetz, M. M., A. L. Radtke, M. K. Lay, B. E. Hjelm, A. N. Bolick, S. S. Sarker, R. L. Atmar, D. H. Kingsley, C. J. Arntzen, M. K. Estes, and C. A. Nickerson. 2013. Lack of Norovirus replication and histo-blood group antigen expression in 3-dimensional intestinal epithelial cells. Emerg. Infect Dis 19:431-438.
6. Jiang, X., M. Wang, D. Y. Graham, and M. K. Estes. 1992. Expression, self-assembly, and antigenicity of the Norwalk virus capsid protein. J Virol 66:6527-6532.
7. Jiang, X., M. Wang, K. Wang, and M. K. Estes. 1993. Sequence and genomic organization of Norwalk virus. Virology 195:51-61.
8. Jones, M. K., M. Watanabe, S. Zhu, C. L. Graves, L. R. Keyes, K. R. Grau, M. B. Gonzalez-Hernandez, N. M. Iovine, C. E. Wobus, J. Vinje, S. A. Tibbetts, S. M. Wallet, and S. M. Karst. 2014. Enteric bacteria promote human and mouse Norovirus infection of B cells. Science 346:755-759.
9. Kapikian, A. Z., R. G. Wyatt, R. Dolin, T. S. Thornhill, A. R. Kalica, and R. M. Chanock. 1972. Visualization by immune electron microscopy of a 27-nm particle associated with acute infectious nonbacterial gastroenteritis. J Virol 10:1075-1081.
10. Moore, M. D., R. M. Goulter, and L. A. Jaykus. 2015. Human Norovirus as a foodborne pathogen: challenges and developments. Annu. Rev Food. Sci Technol. 6:411-433.
11. Papafragkou, E., J. Hewitt, G. W. Park, G. Greening, and J. Vinje. 2013. Challenges of culturing human Norovirus in three-dimensional organoid intestinal cell culture models. PLoS One 8:e63485.

12. Ramani, S., R. L. Atmar, and M. K. Estes. 2014. Epidemiology of human Noroviruses and updates on vaccine development. Curr Opin Gastroenterol 30:25-33.
13. Reeck, A., O. Kavanagh, M. K. Estes, A. R. Opekun, M. A. Gilger, D. Y. Graham, and R. L. Atmar. 2010. Serological correlate of protection against Norovirus-induced gastroenteritis. J Infect Dis 202:1212-1218.
14. Sato, T., D. E. Stange, M. Ferrante, R. G. Vries, J. H. Van Es, B. S. Van den, W. J. Van Houdt, A. Pronk, J. Van Gorp, P. D. Siersema, and H. Clevers. 2011. Long-term expansion of epithelial organoids from human colon, adenoma, adenocarcinoma, and Barrett's epithelium. Gastroenterology 141:1762-1772.
15. Schwab, K. J., M. K. Estes, F. H. Neill, and R. L. Atmar. 1997. Use of heat release and an internal RNA standard control in reverse transcription-PCR detection of Norwalk virus from stool samples. J Clin Microbiol 35:511-514.
16. Straub, T. M., R. A. Bartholomew, C. O. Valdez, N. B. Valentine, A. Dohnalkova, R. M. Ozanich, C. J. Bruckner-Lea, and D. R. Call. 2011. Human Norovirus infection of caco-2 cells grown as a three-dimensional tissue structure. J Water. Health. 9:225-240.
17. Straub, T. M., B. K. Honer zu, P. Orosz-Coghlan, A. Dohnalkova, B. K. Mayer, R. A. Bartholomew, C. O. Valdez, C. J. Bruckner-Lea, C. P. Gerba, M. Abbaszadegan, and C. A. Nickerson. 2007. In vitro cell culture infectivity assay for human Noroviruses. Emerg. Infect Dis 13:396-403.
18. Straub, T. M., J. R. Hutchison, R. A. Bartholomew, C. O. Valdez, N. B. Valentine, A. Dohnalkova, R. M. Ozanich, and C. J. Bruckner-Lea. 2013. Defining cell culture conditions to improve human Norovirus infectivity assays. Water. Sci Technol. 67:863-868.
19. Takanashi, S., L. J. Saif, J. H. Hughes, T. Meulia, K. Jung, K. A. Scheuer, and Q. Wang. 2014. Failure of propagation of human Norovirus in intestinal epithelial cells with microvilli grown in three-dimensional cultures. Arch. Virol 159:257-266.
20. Taube, S., A. O. Kolawole, M. Hohne, J. E. Wilkinson, S. A. Handley, J. W. Perry, L. B. Thackray, R. Akkina, and C. E. Wobus. 2013. A mouse model for human Norovirus. MBio 4:
21. Teunis, P. F., C. L. Moe, P. Liu, S. E. Miller, L. Lindesmith, R. S. Baric, J. Le Pendu, and R. L. Calderon. 2008. Norwalk virus: how infectious is it? J Med Virol 80:1468-1476
22. VanDussen, K. L., J. M. Marinshaw, N. Shaikh, H. Miyoshi, C. Moon, P. I. Tarr, M. A. Ciorba, T. S. Stappenbeck. 2015. Development of an enhanced human gastrointestinal epithelial culture system to facilitate patient-based assays. Gut 64:911-920

Ramani, R. L. Atmar, M. K. Estes. Epidemiology of human noroviruses and updates on vaccine development. Curr Opin Gastroenterol 30, 25 (2014).
Ahmed et al. Global prevalence of norovirus in cases of gastroenteritis: a systematic review and meta-analysis. Lancet Infect Dis 14, 725 (2014).
Hall et al. Norovirus disease in the United States. Emerg Infect Dis 19, 1198 (2013).
Payne et al. Norovirus and medically attended gastroenteritis in U.S. children. N Engl J Med 368, 1121 (2013).
Green. Norovirus infection in immunocompromised hosts. Clin Microbiol Infect 20, 717 (2014).
Belliot, B. A. Lopman, K. Ambert-Balay, P. Pothier. The burden of norovirus gastroenteritis: an important foodborne and healthcare-related infection. Clin Microbiol Infect 20, 724 (2014).
Straub et al. In vitro cell culture infectivity assay for human noroviruses. Emerg Infect Dis 13, 396 (2007).
Moore, R. M. Goulter, L. A. Jaykus. Human norovirus as a foodborne pathogen: challenges and developments. Annu Rev Food Sci Technol 6, 411 (2015).
Jones et al. Human norovirus culture in B cells. Nat Protoc 10, 1939 (2015).
Jones et al. Enteric bacteria promote human and mouse norovirus infection of B cells. Science 346, 755 (2014).
Duizer et al. Laboratory efforts to cultivate noroviruses. J Gen Virol 85, 79 (2004).
Lay et al. Norwalk virus does not replicate in human macrophages or dendritic cells derived from the peripheral blood of susceptible humans. Virology 406, 1 (2010).
Sato et al. Long-term expansion of epithelial organoids from human colon, adenoma, adenocarcinoma, and Barrett's epithelium. Gastroenterology 141, 1762 (2011).
Saxena et al. Human intestinal enteroids: a new model to study human rotavirus infection, host restriction, and pathophysiology. J Virol 90, 43 (2015).
VanDussen et al. Development of an enhanced human gastrointestinal epithelial culture system to facilitate patient-based assays. Gut 64, 911 (2015).
Zachos et al. Human enteroids/colonoids and intestinal organoids functionally recapitulate normal intestinal physiology and pathophysiology. J Biol Chem 291, 3759 (2016).
Kapikian et al. Visualization by immune electron microscopy of a 27-nm particle associated with acute infectious nonbacterial gastroenteritis. J Virol 10, 1075 (1972).
White, M. E. Hardy, M. K. Estes. Biochemical characterization of a smaller form of recombinant Norwalk virus capsids assembled in insect cells. J Virol 71, 8066 (1997).
Green, in Fields Virology, D. M. Knipe, P. M. Howley, Eds. (Lippincott Williams and Wilkins, Philadelphia, 2013), chap. 20, pp. 582-608.
Hofmann, in Physiology of the gastrointestinal tract, L. R. Johnson, Ed. (Raven Press, New York, 1994), chap. 44, pp. 1555-1576.
Reed, H. Muench. A simple method of estimating fifty percent endpoints. Am J Hyg 27, 493 (1938).
Atmar et al. Norwalk virus shedding after experimental human infection. Emerg Infect Dis 14, 1553 (2008).
Le Guyader et al. Detection and analysis of a small round-structured virus strain in oysters implicated in an outbreak of acute gastroenteritis. Appl Environ. Microbiol 62, 4268 (1996).
Agus, R. Dolin, R. G. Wyatt, A. J. Tousimis, R. S. Northrup. Acute infectious nonbacterial gastroenteritis: intestinal histopathology. Histologic and enzymatic alterations during illness produced by the Norwalk agent in man. Ann Intern Med 79, 18 (1973).
Cheetham et al. Pathogenesis of a genogroup II human norovirus in gnotobiotic pigs. J Virol 80, 10372 (2006).
Middendorp et al. Adult stem cells in the small intestine are intrinsically programmed with their location-specific function. Stem Cells 32, 1083 (2014).
Ruvoen-Clouet, G. Belliot, J. Le Pendu. Noroviruses and histo-blood groups: the impact of common host genetic polymorphisms on virus transmission and evolution. Rev Med Virol 23, 355 (2013).
Reeck et al. Serological correlate of protection against norovirus-induced gastroenteritis. J Infect Dis 202, 1212 (2010).

Richardson, R. F. Bargatze, R. Goodwin, P. M. Mendelman. Norovirus virus-like particle vaccines for the prevention of acute gastroenteritis. Expert Rev Vaccines 12, 155 (2013).

Atmar et al. Norovirus vaccine against experimental human Norwalk Virus illness. N Engl J Med 365, 2178 (2011).

Atmar, M. K. Estes. The epidemiologic and clinical importance of norovirus infection. Gastroenterol Clin North Am 35, 275 (2006).

Tan, X. Jiang. Norovirus and its histo-blood group antigen receptors: an answer to a historical puzzle. Trends Microbiol 13, 285 (2005).

Otto et al. Infection of calves with bovine norovirus GIII.1 strain Jena virus: an experimental model to study the pathogenesis of norovirus infection. J Virol 85, 12013 (2011).

Karandikar et al. Detection of human norovirus in intestinal biopsies from immunocompromised transplant patients. J Gen Virol (2016) July 12. doi: 10.1099/jgv.0.000545. [Epub ahead of print].

Taube et al. A mouse model for human norovirus. MBio. 4, e00450 (2013).

Bok et al. Chimpanzees as an animal model for human norovirus infection and vaccine development. Proc Natl Acad Sci USA 108, 325 (2011).

Green. Editorial Commentary: Noroviruses and B Cells. Clin Infect Dis 62, 1139 (2016).

Brown, K. Gilmour, J. Breuer. Norovirus infections occur in B-cell deficient patients. Clin Inect Dis 62, 1136 (2016).

Flynn, L. J. Saif. Serial propagation of porcine enteric calicivirus-like virus in primary porcine kidney cell cultures. J Clin Microbiol 26, 206 (1988).

Chang et al. Bile acids are essential for porcine enteric calicivirus replication in association with down-regulation of signal transducer and activator of transcription 1. Proc Natl Acad Sci USA 101, 8733 (2004).

Ramani et al. Mucosal and cellular immune responses to norwalk virus. J Infect Dis 212, 397 (2015).

Loisy et al. Real-time RT-PCR for norovirus screening in shellfish. J Virol Methods 123, 1 (2005).

Kageyama et al. Broadly reactive and highly sensitive assay for Norwalk-like viruses based on real-time quantitative reverse transcription-PCR. J Clin Microbiol 41, 1548 (2003).

Guix et al. Norwalk virus RNA is infectious in mammalian cells. J Virol 81, 12238 (2007).

Le Guyader et al. Aichi virus, norovirus, astrovirus, enterovirus, and rotavirus involved in clinical cases from a French oyster-related gastroenteritis outbreak. J Clin Microbiol 46, 4011 (2008).

Jiang, M. Wang, D. Y. Graham, M. K. Estes. Expression, self-assembly, and antigenicity of the Norwalk virus capsid protein. J Virol 66, 6527 (1992).

Katayama et al. Plasmid-based human norovirus reverse genetics system produces reporter-tagged progeny virus containing infectious genomic RNA. Proc Natl Acad Sci USA 111, E4043 (2014).

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A system for culturing a virus of the Caliciviridae family, comprising:
    a) mammalian small intestinal enteroid cultures; and
    b) bile or a functionally active fraction or component thereof.

2. The system of claim 1, further comprising the virus.

3. The system of claim 1, wherein the cultures are derived from human small intestines.

4. The system of claim 1, wherein the source of bile is primate, human, pig, bovine, or a combination thereof.

5. The system of claim 1, wherein the concentration of bile is in a range of 0.2-10% for human bile, 0.01-0.1% for bovine bile, or 1-2% for sow bile.

6. The system of claim 1, wherein the functionally active fraction or component thereof is not in a lipid micelle, is not a protein, is not a lipid or fatty acid, and/or is not cholesterol.

7. The system of claim 1, wherein the functionally active fraction or component thereof comprises one or more lipids, one or more fatty acids, one or more sterols, or a combination thereof.

8. The system of claim 1, wherein the functionally active fraction or component thereof comprises one or more bile acids.

9. The system of claim 8, wherein the bile acid is selected from the group consisting of glycochenodeoxycholic acid, taurochenodeoxycholic acid, taurodeoxycholic acid, glycocholic acid, taurocholic acid, tauroursodeoxycholic acid, cholic acid, deoxycholic acid, lithocholic acid, chenodeoxycholic acid, glycodeoxycholic acid, taurolithocholic acid, ursodeoxycholic acid, glycolithocholic acid, or a combination thereof.

10. The system of claim 1, wherein the system comprises one or more ceramides.

11. A system for culturing a noncultivatable human enteric virus, comprising:
    a) mammalian small intestinal enteroid cultures; and
    b) bile or a functionally active fraction or component thereof.

12. The system of claim 11, further comprising a virus.

13. The system of claim 12, wherein the virus is from the family Toroviridae, Picobirnaviridae, Picornaviridae, or Coronaviridae.

14. The system of claim 13, wherein the Picobirnaviridae virus is picobirnavirus.

15. The system of claim 13, wherein the Picornaviridae virus is poliovirus or coxsackie B virus.

16. The system of claim 13, wherein the Coronaviridae virus is from the genus Coronavirinae, the genus Torovirus, or the order Nidovirales.

17. The system of claim 16, wherein the genus Coronavirinae virus is human enteric coronavirus.

18. The system of claim 12, wherein the noncultivatable human enteric virus is an astrovirus, Breda virus, human rotavirus, enteric adenovirus, human enteric coronavirus, or human enterovirus.

19. The system of claim 12, further comprising one or more ceramides.

20. A system for culturing a virus of the Caliciviridae family, comprising:
   a) mammalian gastroid or colonoid cultures; and
   optionally b) bile or a functionally active fraction or component thereof.

21. The system of claim 20, further comprising one or more ceramides.

\* \* \* \* \*